US012807733B2

(12) United States Patent
Park et al.

(10) Patent No.: US 12,807,733 B2
(45) Date of Patent: *Nov. 24, 2026

(54) PHARMACEUTICAL COMPOSITION FOR SUBCUTANEOUS ADMINISTRATION CONTAINING HUMAN HYALURONIDASE PH20 VARIANT AND DRUG

(71) Applicant: ALTEOGEN INC., Daejeon (KR)

(72) Inventors: Soon Jae Park, Daejeon (KR); Hye-Shin Chung, Daejeon (KR); Seung Joo Lee, Daejeon (KR); Kyuwan Kim, Daejeon (KR); Minsoo Byun, Daejeon (KR); Ki Seok Nam, Daejeon (KR); Sun-Ah You, Daejeon (KR); Chang Woo Lee, Daegu (KR); Hyung-Nam Song, Daejeon (KR)

(73) Assignee: ALTEOGEN Inc., Daejeon (KR)

( * ) Notice: Subject to any disclaimer, the term of this patent is extended or adjusted under 35 U.S.C. 154(b) by 1150 days.

This patent is subject to a terminal disclaimer.

(21) Appl. No.: 17/744,575

(22) Filed: May 13, 2022

(65) Prior Publication Data

US 2022/0289864 A1 Sep. 15, 2022

Related U.S. Application Data

(63) Continuation of application No. 17/052,952, filed as application No. PCT/KR2020/003975 on Mar. 24, 2020, now Pat. No. 12,570,766.

(30) Foreign Application Priority Data

Mar. 25, 2019 (KR) ........................ 10-2019-0033880

(51) Int. Cl.

| | |
|---|---|
| ***C07K 16/32*** | (2006.01) |
| ***A61K 45/06*** | (2006.01) |
| ***A61K 47/26*** | (2006.01) |
| ***C12N 9/26*** | (2006.01) |

(52) U.S. Cl.

CPC .............. *C07K 16/32* (2013.01); *A61K 45/06* (2013.01); *A61K 47/26* (2013.01); *C12N 9/2474* (2013.01); *C07K 2317/94* (2013.01); *C12Y 302/01035* (2013.01)

(58) Field of Classification Search

CPC .. A61K 2300/00; A61K 45/06; A61K 9/0019; A61K 2039/505; A61K 47/6813; A61K 47/6849; A61K 47/6879; A61K 47/6851; C12N 9/2474

See application file for complete search history.

(56) References Cited

U.S. PATENT DOCUMENTS

| | | | |
|---|---|---|---|
| 5,721,348 | A | 2/1998 | Primakoff et al. |
| 5,854,046 | A | 12/1998 | Au-Young et al. |
| 7,767,429 | B2 | 8/2010 | Bookbinder et al. |
| 8,105,586 | B2 | 1/2012 | Bookbinder et al. |
| 8,202,517 | B2 | 6/2012 | Bookbinder et al. |
| 8,257,699 | B2 | 9/2012 | Bookbinder et al. |
| 8,288,142 | B2 | 10/2012 | Uvarkina et al. |
| 8,431,124 | B2 | 4/2013 | Bookbinder et al. |
| 8,431,380 | B2 | 4/2013 | Bookbinder et al. |
| 8,450,470 | B2 | 5/2013 | Bookbinder et al. |
| 8,580,252 | B2 | 11/2013 | Bookbinder et al. |
| 8,765,685 | B2 | 7/2014 | Bookbinder et al. |
| 8,772,246 | B2 | 7/2014 | Bookbinder et al. |
| 8,927,249 | B2 | 1/2015 | Wei et al. |
| 9,211,315 | B2 | 12/2015 | Bookbinder et al. |
| 9,284,543 | B2 | 3/2016 | Wei et al. |
| 9,447,401 | B2 | 9/2016 | Wei et al. |
| 9,562,223 | B2 | 2/2017 | Bookbinder et al. |
| 9,677,061 | B2 | 6/2017 | Bookbinder et al. |
| 9,677,062 | B2 | 6/2017 | Bookbinder et al. |
| 10,286,044 | B2 | 5/2019 | Bookbinder et al. |
| 10,328,130 | B2 | 6/2019 | Frost et al. |

(Continued)

FOREIGN PATENT DOCUMENTS

| | | | |
|---|---|---|---|
| AR | 027553 | A1 | 4/2003 |
| CN | 101970650 | A | 2/2011 |

(Continued)

OTHER PUBLICATIONS

Sandborn et al (Alimentary Pharmacology & Therapeutics, 2018, vol. 48, pp. 65-77) (Year: 2018).*

(Continued)

*Primary Examiner* — Karen A. Canella

(74) *Attorney, Agent, or Firm* — Sughrue Mion, PLLC

(57) ABSTRACT

The present invention relates to a pharmaceutical composition including (a) a drug and (b) a human PH20 variant. The human PH20 variant included in the pharmaceutical composition according to the present invention comprises amino acid residue substitution(s) in one or more regions selected from an alpha-helix 8 region (S347 to C381) and a linker region (A333 to R346) between alpha-helix 7 and alpha-helix 8 in wild-type human PH20 having the amino acid sequence of SEQ ID NO: 1, wherein amino acid residue(s) located at the N-terminus or the C-terminus is (are) selectively truncated. In addition, the pharmaceutical composition according to the present invention may further comprise a pharmaceutically acceptable additive, particularly a stabilizer. The pharmaceutical composition according to the present invention can maximize the therapeutic effect of a drug used in combination therewith, due to the effect of human PH20 variants.

31 Claims, 21 Drawing Sheets

Specification includes a Sequence Listing.

(56) References Cited

U.S. PATENT DOCUMENTS 10,865,400 B2 12/2020 Wei et al.
10,898,551 B2 1/2021 Bookbinder et al.
10,918,736 B2 2/2021 Kim et al.
11,041,149 B2 6/2021 Wei et al.
11,066,656 B2 7/2021 Wei et al.
11,633,476 B2 4/2023 Sharma et al.
11,723,959 B2 8/2023 Bookbinder et al.
11,952,600 B2 4/2024 Wei et al.
12,091,692 B2 9/2024 Wei et al.
12,104,185 B2 10/2024 Wei et al.
2006/0104968 A1 5/2006 Bookbinder et al.
2009/0123367 A1 5/2009 Bookbinder et al.
2010/0003238 A1 1/2010 Frost et al.
2010/0143457 A1 6/2010 Wei et al.
2010/0305500 A1 12/2010 Lambert et al.
2011/0044977 A1 2/2011 Adler et al.
2012/0148535 A1 6/2012 Carrio et al.
2012/0205311 A9 8/2012 Kopf et al.
2013/0101577 A9 4/2013 Wei et al.
2013/0302275 A1 11/2013 Wei et al.
2014/0037613 A1 2/2014 Bookbinder et al.
2014/0199282 A1 7/2014 Bookbinder et al.
2015/0001529 A1 1/2015 Kurokawa
2015/0010529 A1 1/2015 Wei
2015/0165059 A1 6/2015 Bookbinder et al.
2016/0362670 A1 12/2016 Wei et al.
2017/0089914 A1 3/2017 Loo et al.
2017/0218069 A1 8/2017 Rosengren et al.
2017/0218382 A1 8/2017 Kondo et al.
2018/0044419 A9 2/2018 Rosengren et al.
2018/0185506 A1 7/2018 Bookbinder et al.
2018/0250397 A1 9/2018 Benyunes et al.
2019/0030076 A1* 1/2019 Han .................... C12N 5/0667
2019/0046657 A1 2/2019 Kim et al.
2020/0157208 A1* 5/2020 Barrington ........... C07K 16/244
2020/0262922 A1 8/2020 Bhattacharya et al.
2021/0047408 A1 2/2021 Lala et al.
2021/0155913 A1 5/2021 Park et al.
2021/0346497 A1 11/2021 Huber
2021/0363270 A1 11/2021 Park et al.
2021/0380694 A1 12/2021 Forrest, Jr. et al.
2022/0089738 A1 3/2022 Krishnamachari et al.
2022/0289864 A1 9/2022 Park et al.
2023/0174963 A1 6/2023 Park et al.
2023/0250408 A1 8/2023 Park et al.
2023/0321203 A1 10/2023 Bookbinder et al.
2023/0365692 A1 11/2023 Krishnamachari et al.
2024/0150467 A1 5/2024 Akala et al.
2025/0074983 A1 3/2025 Lala et al.

FOREIGN PATENT DOCUMENTS

CN 102065886 A 5/2011
CN 102307993 A 1/2012
CN 103173474 A 6/2013
CN 104244968 A 12/2014
CN 104745553 A 7/2015
CN 105567606 A 5/2016
CN 110494450 A 11/2019
CN 111971387 A 11/2020
CO 2021011944 A2 9/2021
EA 22752 B1 2/2016
EP 2 405 015 A2 1/2012
EP 2662090 A1 11/2013
EP 2 674 487 A1 12/2013
EP 1858926 B1 10/2015
EP 3037529 A1 6/2016
EP 3 045 472 A1 7/2016
EP 2797622 B1 10/2016
EP 3 186 281 B1 4/2019
EP 3130347 B1 9/2019
EP 3636752 A1 4/2020
EP 3785701 A1 3/2021
ES 2573462 T3 6/2016
JP 2009515521 A 4/2009
JP 2011512844 A 4/2011
JP 2012511327 A 5/2012
JP 2015504666 A 2/2015
JP 2015095423 A 5/2015
JP 2018052818 A 4/2018
JP 2020500863 A 1/2020
JP 2021123202 A 8/2021
JP 2022066832 A 5/2022
JP 2022094567 A 6/2022
JP 7166478 B2 7/2022
JP 202425986 A 2/2024
JP 202425989 A 2/2024
JP 2024081274 A 6/2024
KR 20100135291 A 12/2010
KR 201200994493 A 8/2012
KR 1020120105426 A 9/2012
KR 101233457 B1 2/2013
KR 1020130116386 A 10/2013
KR 101363658 B1 2/2014
KR 20140021046 A 2/2014
KR WEI20140021046 A 2/2014
KR 101493644 B1 2/2015
KR 101546563 B1 8/2015
KR 1020160052812 A 5/2016
KR 101647932 B1 8/2016
KR 10-2017-0065032 A 6/2017
KR 101874401 B1 7/2018
KR 1020200017538 A 2/2020
KR 1020200130451 A 11/2020
KR 10-2021-0023798 A 3/2021
KR 10-2022-0069045 A 5/2022
TW 201534726 A 9/2015
TW 2021 40780 A 11/2021
WO 2004078140 A2 9/2004
WO 2007064437 A2 6/2007
WO 2009065507 A2 5/2009
WO 2009111066 A1 9/2009
WO 2009117085 A1 9/2009
WO 2009128917 A2 10/2009
WO 2010077297 A1 7/2010
WO 2011012637 A2 2/2011
WO 2011029892 A2 3/2011
WO 2011034604 A2 3/2011
WO 2012135408 A 4/2012
WO 2012174478 A2 12/2012
WO 2013202020 A1 4/2013
WO WO2013102144 A2 7/2013
WO 2015003167 A1 1/2015
WO 2015071366 A1 5/2015
WO 2015/095418 A1 6/2015
WO 2015095423 A2 6/2015
WO 2016033555 A1 3/2016
WO 2016061286 A2 4/2016
WO 2017004706 A1 1/2017
WO 2017079150 A1 5/2017
WO 2017131496 A1 8/2017
WO 2018052818 A1 3/2018
WO 2018102372 A1 6/2018
WO 2018204368 8/2018
WO 2018183928 A1 10/2018
WO 2018222722 A2 12/2018
WO 2019222435 A1 11/2019
WO 2020022791 A1 1/2020
WO 2020172621 A1 8/2020
WO 2020197230 A1 10/2020
WO 2021123202 A1 6/2021
WO 2021150079 A1 7/2021
WO 2022031093 A1 2/2022
WO 2022066832 A1 3/2022
WO 2022094567 A1 5/2022
WO 2023075506 A1 5/2023
WO 2024025986 A1 2/2024
WO 2024025989 A1 2/2024

(56) References Cited

FOREIGN PATENT DOCUMENTS

| | | |
|---|---|---|
| WO | 2024081274 A1 | 4/2024 |
| WO | 2024081276 A1 | 4/2024 |

OTHER PUBLICATIONS

Boekhout et al (The Oncologist, 2011, vol. 16, pp. 800-810) (Year: 2011).*
Cingo (mAbs, 2009, vol. 1, pp. 216-212) (Year: 2009).*
Hardy et al., "Assessment of contraceptive vaccines based on recombinant mouse sperm protein PH20," Reprod., 127:325-334 (2004).
Hayden, "Chemistry: Designer Debacle," Nature, 453:275-278 (2008).
Hayden, "Key Protein-Design Papers Challenged," Nature, 461:859 (2009).
Green, "Computer Graphics, Homology Modeling, and Bioinformatics," Protein Eng'g & Design, Ch. 10, 223-237 (2010).
EP20776465.5—Communication pursuant to 94(3) EPC mailed on Jul. 16, 2024, 7 pages.
File History of U.S. Pat. No. 11,952,600.
TW111136059—Second Office Action mailed on Sep. 5, 2024, 6 pages.
Yue et al., "Loss of Protein Structure Stability as a Major Causative Factor in Monogenic Disease," J. Mol. Biol., 353:459-473 (2005).
Zhang et al., "Hyaluronidase Activity of Human Hyal1 Requires Active Site Acidic and Tyrosine Residues," J. Biol. Chem., 284(14):9433-9442 (2009).
Collection of Swiss-Model Webpages from the Internet Archive, navigable from: https://web.archive.org/web/20110519141121/ http://swissmodel.expasy.org/?pid=smh01&uid=&token=, accessed Nov. 9, 2024.
Communication dated Dec. 5, 2024 issued by the European Patent Office in application No. 24185844.8.
"Highlights of prescribing information", Keytruda, pp. 1-16, 2014, www.fda.gov/drugsatfda.
Hecht et al., "De Novo Proteins from Designed Combinatorial Libraries," Protein Sci., 13:1711-1723 (2004).
Hom_pre2011 (Exhibit 1053 in PGR2025-00003).
Wang & Moult, "SNPs, Protein Structure, and Disease," Hum. Mutation, 17:263-270 (2001).
Xiong et al., "Periodicity of Polar and Nonpolar Amino Acids is the Major Determinant of Secondary Structure in Self-Assembling Oligomeric Peptides," PNAS, 92: 6349-6353 (1995).
"Negative Results," Nature: Editorials, 453:258 (2008).
Hom_pre2011.fasta (Exhibit 1056 in PGR2025-00003).
Hom_pre2011_header (Exhibit 1054 in PGR2025-00003).
TW110102662—Second Office Action mailed on Sep. 5, 2024, 6 pages.
U.S. Appl. No. 13/694,731.
U.S. Appl. No. 61/631,313.
U.S. Appl. No. 16/628,258—Notice of Allowance mailed on Aug. 16, 2024, 8 pages.
Alberts, "Molecular Biology of the Cell," Fifth Edition, Chapter 3 (2007).
Swiss Model Printout of PH20 Model with D320S Mutation, printed Nov. 9, 2024 (Exhibit 1073 in PGR2025-00003).
Table Associating Citations from the U.S. Pat. No. 11,952,600 Patent (Exhibit 1001 in PGR2025-00003) to Corresponding Citations in U.S. Appl. No. 13/694,731Application (Exhibit 1026 in PGR2025-00003).
Tung et al., "Mechanism of Infertility in Male Guinea Pigs Immunized with Sperm PH-20," Biol. Reprod., 56(5):1133-41 (1997).
Alexander et al., "A Minimal Sequence Code for Switching Protein Structure and Function," PNAS, 106:21149-21154 (2009).
Hom_pre2011_header_clean (Exhibit 1055 in PGR2025-00003).
Hossler et al., "Optimal and consistent protein glycosylation in mammalian cell culture", Glycobiology, vol. 19, No. 9, Jun. 3, 2009, pp. 936-949.
Stern et al., "The Hyaluronidases: Their Genomics, Structures, and Mechanisms of Action," Chem. Rev. 106:818-839 (2006).
Steipe, "Consensus-Based Engineering of Protein Stability: From Intrabodies to Thermostable Enzymes," Methods in Enzymology, 388:176-186 (2004).
Sills, "Retraction," Science, 319:569 (2008).
Jedzrejas et al., "Structures of Vertebrate Hyaluronidases and Their Unique Enzymatic Mechanism of Hydrolysis," Proteins: Structure, Function and Bioinformatics, 61:227-238 (2005).
Schwede et al., "Swiss-Model: An Automated Protein Homology-Modeling Server," Nucleic Acids Rsch., 31:3381-3385 (2003).
Ruan et al., "Design and Characterization of a Protein Fold Switching Network," Nature Comm., 14 (2023).
JP2021-567961—Decision to Grant a Patent mailed on Oct. 8, 2024, 7 pages.
AU2021320569—Notice of Acceptance mailed on Sep. 20, 2024, 4 pages.
Redline Comparison of U.S. Appl. No. 13/694,731 application (Exhibit 1026 in PGR2025-00003) and U.S. Pat. No. 11,952,600 Patent (Exhibit 1001 in PGR2025-00003) Specifications.
JP2023026863—Decision of Refusal mailed on Oct. 8, 2024, 4 pages.
Ph20_pre2011 Alignment html (Exhibit 1058 in PGR2025-00003).
Ph20_pre2011.aln-clustal_num (Exhibit 1057 in PGR2025-00003).
Primakoff et al., "Reversible Contraceptive Effect of PH-20 Immunization in Male Guinea Pigs," Biol Reprod., 56(5):1142-6 (1997).
R.D. Harvey, et al., "Early results of pegvorhyaluronidase alfa (PEGPH20; PVHA) + pembrolizumab therapy in patients (Pts) with relapsed/refractory gastric/gastroedophageal junction (GEJ) adenocarcinoma", Annals of Oncology, vol. 29, Supplement 9, Nov. 2018, 1 page.
AU2023200324—Examination Report No. 1 mailed on Aug. 22, 2024, 2 pages.
Kegg, Drug: Hyaluronidase (human recombinant), available at: https://www.genome.jp/entry/D06604, accessed Oct. 5, 2024.
KR20207024813—Request for the Submission of an Opinion mailed on Jul. 30, 2024, 14 pages.
Merck Sharp & Dohme, LLC, Relative Bioavailability Study of Subcutaneous Injection Versus Intravenous Infusion of Pembrolizumab (MK-3475) in participants with advanced melanoma (MK-3475-555/Keynote-555), National Library of Medicine: National Center for Biotechnology Information, 2023, pp. 1-20.
Mihel, "PSAIA—Protein Structure and Interaction Analyzer," BMC Structural Biology, 8:21 (2008).
Baba et al., "Mouse Sperm Lacking Cell Surface Hyaluronidase PH-20 Can Pass through the Layer of Cumulus Cells and Fertilize the Egg," J. Biol. Chem., 277(33):30310-4 (2002).
Beasley & Hecht, "Protein Design: The Choice of de Novo Sequences," J. Biological Chemistry, 272:2031-2034 (1997).
KR20240036308—Written Decision on Registration mailed on Sep. 2, 2024, 6 pages.
Leisola & Turunen, "Protein Engineering: Opportunities and Challenges," Appl. Microbiol. Biotechnol. 75:1225-1232 (2007).
Lins et al., "Analysis of Accessible Surface of Residues in Proteins," Protein Sci., 12:1406-1417 (2003).
Studies of Peptides and Proteins, Biophysical J. 75:422-427.
Bordoli et al., "Protein structure homology modeling using SwissModel workspace," Nature Protocols, 4(1):1-13 (2008).
BR1120200190411—Office Action mailed on Oct. 15, 2024, 8 pages.
Pace & Scholtz, A Helix Propensity Scale Based on Experimental.
Petition for Post Grant Review filed Nov. 12, 2024 in Case No. PGR2025-00003, U.S. Pat. No. 11,952,600.
Brandon & Tooze, "Introduction to Protein Structure," Second Ed., Chapters 1-6, 11-12, 17-18 (1999).
Butler M., "Optimisation of the Cellular Metabolism of Glycosylation for Recombinant Proteins Produced by Mammalian Cell Systems", Cytotechnology, vol. 50, No. 1-3, Jun. 9, 2006, pp. 57-76.
He, et al., "NMR Structures of Two Designed Proteins with High Sequence Identity but Different Fold and Function," PNAS, 105:14412-14417 (2008).

(56) References Cited

OTHER PUBLICATIONS

Pomering et al., "Restricted Entry of IgG into Male and Female Rabbit Reproductive Ducts Following Immunization with Recombinant Rabbit PH-20," Am. J. Reprod. Immunol., (3):174-82.
Rosengren et al., "Clinical Immunogenicity of rHuPH20, a Hyaluronidase Enabling Subcutaneous Drug Administration," AAPS J., 17:1144-1156 (2015).
Rosengren et al., "Recombinant Human PH20: Baseline Analysis of the Reactive Antibody Prevalence in the General Population Using Healthy Subjects," BioDrugs, 32(1):83-89 (2018).
Collection of Blast Webpages from the Internet Archive, navigable from: https://web.archive.org/web/20111022151531/http://www.clustal.o.
Gmachl et al., "The human sperm protein PH-20 has hyaluronidase activity," FEBS Letters, 3:545-548 (1993).
EP21853474.1—Extended European search report mailed on Jul. 31, 2024, 14 pages.
Sievers et al., "Fast, Scalable Generation of High-Quality Protein Multiple Sequence Alignments Using Clustal Omega," Molecular Sys. Biology, 7.1 (2011).
Declaration of Michael Hecht, Ph.D. Executed Nov. 12, 2024, Case No. PGR2025-00003, U.S. Pat. No. 11,952,600 (Exhibit 1003 in PGR2025-00003).
U.S. Appl. No. 61/796,208.
Declaration of Dr. Sheldon Park Executed Nov. 8, 2024, Case No. PGR2025-00003, U.S. Pat. No. 11,952,600 (Exhibit 1004 in PGR2025-00003).
Swiss Model Printout of PH20 Model, printed Nov. 10, 2024 (Exhibit 1069 in PGR2025-00003).
TW112123526—Second Office Action mailed on Sep. 6, 2024, 6 pages.
Swiss Model Printout of PH20 Model with D320R Mutation, printed Nov. 9, 2024 (Exhibit 1072 in PGR2025-00003).
Collection of Clustal Omega Webpages from the Internet Archive, navigable from: https://web.archive.org/web/20111022151531/http://www.clustal.o.
Collection of PyMol Webpages from the Internet Archive, navigable from: https://web.archive.org/web/20110701072314/http://pymol.org/, accessed Nov. 7, 2024.
Declaration of Jeffrey P. Kushan dated Nov. 12, 2024, Case No. PGR2025-00003 U.S. Pat. No. 11,952,600 (Exhibit 1068 in PGR2025-00003).
Merck Sharp & Dohme LLC, et al. "Phase II Study of PEGPH20 and Pembrolizumab (MK-3475) for Patients With Previously Treated Hyaluronan High (HA-High) Metastatic Pancreatic Ductal Adenocarcinoma," Clinical Trails NCT03634332, Protocol ID PCRT 16-001, Version 1 (Aug. 14, 2018).
Merck Sharp & Dohme LLC, et al. "Phase II Study of PEGPH20 and Pembrolizumab (MK-3475) for Patients With Previously Treated Hyaluronan High (HA-High) Metastatic Pancreatic Ductal Adenocarcinoma," Clinical Trails NCT03634332, Protocol ID PCRT 16-001, Version 2 (Aug. 16, 2018).
Merck Sharp & Dohme LLC, et al. "Phase II Study of PEGPH20 and Pembrolizumab (MK-3475) for Patients With Previously Treated Hyaluronan High (HA-High) Metastatic Pancreatic Ductal Adenocarcinoma," Clinical Trails NCT03634332, Protocol ID PCRT 16-001, Version 3 (May 3, 2019).
Bristol-Myers Squibb "A Phase 3, Open-label, Randomized, Noninferiority Trial of Subcutaneous Formulation of Nivolumab Versus Intravenous Nivolumab in Participants With Advanced or Metastatic Clear Cell Renal Cell Carcinoma Who Have Received Prior Systemic Therapy," Clinical Trails NCT04810078, Protocol ID CA209-67T, Version 1 (Mar. 19, 2021).
Kuhn et al., "Biopharmaceutical Composition ED", ip.com, ip.com Inc., West Henrietta, NY, US, Jul. 12, 2019, 723-726 (Jul. 12, 2019).
Humphrey J H et al, "International standard for hyaluronidase", Switzerland Jan. 1, 1957 (Jan. 1, 1957), p. 291-294.
Connor Robert J. et al, "A Preclinical Investigation into the Effects of Aging on Dermal Hyaluronan Properties and Reconstitution Following Recombinant Human Hyaluronidase PH20 Administration", May 2, 2020 (May 2, 2020), vol. 10, No. 3, p. 503-513.
Wang Wei Ed—Blanco-Prieto Maria J. et al, "Instability, stabilization, and formulation of liquid protein pharmaceuticals", International Journal of Pharmaceutics, Elsevier, NL,vol. 185, No. 2, Aug. 20, 1999 (Aug. 20, 1999), p. 129-188.
Falconer Robert J., "Advances in liquid formulations of parenteral therapeutic proteins", Biotechnology Advances., vol. 37, No. 7, Nov. 1, 2019 (Nov. 1, 2019), p. 1-29.
Patnaik et al., Phase I Study of Pembrolizumab (MK-3475; Anti-PD-1 Monoclonal Antibody) in Patients with Advanced Solid Tumors, Clinical Cancer Research, May 14, 2015 [retrieved Nov. 2, 2023]. Retrieved from the Internet <URL: https :1/aacrjournals.org/clincancerres/article/21/19/4286/125563/Phase-I-Study-of-Pembrolizumab-MK-3475-Anti-PD-1>.
Johnson et al., "Assessment of Subcutaneous vs Intravenous Administration of Anti-PD-1 Antibody PF-06801591 in Patients With Advanced Solid Tumors," JAMA Oncology 5(7):999-1007.
Bristol-Myers Squibb "Phase I/II Pharmacokinetic Multi-Tumor Study of Subcutaneous Formulation of Nivolumab Monotherapy," Clinical Trails NCT03656718, Protocol ID CA209-8KX, Version 1 (Aug. 31, 2018).
Thompson et al., "Enzymatic Depletion of Tumor Hyaluronan Induces Antitumor Responses in Preclinical Animal Models," Molecular Cancer Therapeutics 9(11):3052-3064 (2010).
Chan et al., "Therapeutic antibodies for autoimmunity and inflammation", Nature Reviews Immunology, vol. 10, May 2010, pp. 301-316.
Alley et al., "Long-Term Overall Survival for Patients with Malignant Pleural Mesothelioma on Pembrolizumab Enrolled in Keynote-028", Journal of Thoracic Oncology, Abstract No. OA13.03, 2018, vol. 12, No. 1S, p. 1 (S294).
Liming Liu, "Pharmacokinetics of monoclonal antibodies and Fc-fusion proteins", Protein Cell, 2018, vol. 9, No. 1, pp. 15-32.
Arming, S. et al., "In vitro mutagenesis of PH-20 hyaluronidase from human sperm", "European journal of Biochemistry", 1997, vol. 247, pp. 810-814.
Chen, K., et al., "Constitutive expression of recombinant human hyaluronidase PH20 by pichia pastoris", "Elsevier", 2016, vol. xx, pp. 1-6.
International Search Report and Written Opinion mailed Jul. 29, 2021 for International Patent Application No. PCT/KR2021/000943 filed Mar. 24, 2020 (21 pages).
International Search Report and Written Opinion mailed Jun. 30, 2020 for International Patent Application No. PCT/KR2020/003975 filed Mar. 24, 2020 (23 pages).
International Search Report and Written Opinion mailed Oct. 29, 2019 for PCT Application No. PCT/KR2019/009215 filed Jul. 25, 2019 (21 pages).
Lin et al. "Molecular cloning of the human and monkey sperm surface protein PH-20", Proc. Natl. Acad. Sci. Nov. 1993, vol. 90, pp. 10071-10075.
Mcatee, C., et al., "Emerging roles for hyaluronidase in cancer metastasis and therapy", "Advances in cancer research", 2014, vol. 123, pp. 1-34.
Muller et al., "Spliceosomal peptide P140 for immunotherapy of systemic lupus erythematosus", Arthritis & Rheumatism, Dec. 2008, vol. 58, Nb. 12, pp. 3873-3883.
Hyaluronidase PH-20 (Macaca nemestrina) NCBI Reference Sequence: XP011728213.1, Apr. 24, 2018, p. 2.
NCBI Reference Sequence: NP 001166492.1 , hyaluronidase PH-20 precursor [Cavia porcelius], Jun. 21, 2021, pp. 2.
NCBI Reference Sequence: NP 001166492.1 ,hyaluronidase PH-20 precursor [Cavia porcelius], Jun. 19, 2020, pp. 2.
"PH-20 (*Homo sapiens*)", NCBI Genbank Accession No. AAC60607.2, Jun. 5, 2000, p. 1.
Wang et al., "Antibody structure, instability, and formulation,"Journal of pharmaceutical sciences., Jan. 2007, vol. 96, Nb.1, pp. 1-26.
Frost and Stern, "A microtiter-based assay for hyaluronidase activity not requiring specialized reagents", "Analytical Biochemistry", 1997, vol. 251, pp. 263-269.

(56) References Cited

OTHER PUBLICATIONS

Markovic-Housley et al., "Crystal structure of hyaluronidase, a major allergen of bee venom", "Structure", Oct. 2000, vol. 8, , pp. 1025-1035.
Messina et al., "Identification and characterization of a bacterial hyaluronidase and its production in recombinant form", "FEBS Letters", 2016, vol. 590, Issue 14, pp. 2180-2189.
Schon, A., et al., "Denatured state aggregation parameters derived from concentration dependence of protein stability", Elsevier, 2015, vol. 488, pp. 45-50.
Stern and Csoka, "Mammalian Hyaluronidases", "Glycoforum", 2000, vol. 4, pp. 1-6.
Number, "The Hyaluronidases: Their Genomics, Structures, and Mechanisms of Action", "Chern Rev.", 2006, vol. 106, No. 3 with supplemental, pp. 818-839.
Lafaro et al., "The Paradoxical Web of Pancreatic Cancer Tumor Microenvironment", The American journal of pathology, vol. 189, No. 1, pp. 44-57.
Philo et al., "A Critical Review of Methods for Size Characterization of Non-Particulate Protein Aggregates," U.S. Cur. Pharm. Biotech., 2009, vol. 10, 359-372.
Takahashi, T. et al., "A fluorimetric Morgan-Elson assay method for hyaluronidase activity," Anal. Biochem., 2003, vol. 322, 257-263.
U.S. Appl. No. 17/052,952—Non-Final Office Action mailed on Dec. 12, 2023, 32 pages.
U.S. Appl. No. 17/907,538—Requirement for Restriction/Election mailed on May 12, 2023, 5 pages.
U.S. Appl. No. 17/907,538—Non-Final Office Action mailed on Aug. 3, 2023, 10 pages.
U.S. Appl. No. 17/907,538—Ex Parte Quayle Action mailed on Feb. 15, 2024, 4 pages.
U.S. Appl. No. 17/907,538—Notice of Allowance mailed on Apr. 24, 2024, 7 pages.
U.S. Appl. No. 16/628,258—Final Rejection mailed on Mar. 12, 2024, 9 pages.
U.S. Appl. No. 16/628,258—Non-Final Office Action mailed on Aug. 30, 2023, 13 pages.
U.S. Appl. No. 16/628,258—Requirement for Restriction/Election mailed on Mar. 23, 2023, 9 pages.
CA3137324—Office Action mailed on May 6, 2024, 6 pages.
AU2020248612—Examination Report No. 2 mailed on Oct. 25, 2023, 3 pages.
CA3,131,052—Office Action mailed on May 6, 2024, 5 pages.
EP20776465.5—Extended European search report mailed on Feb. 11, 2022, 15 pages.
KR20210103530—Request for the Submission of an Opinion mailed on Sep. 19, 2023, 7 pages.
RU2022125351—Office Action mailed on Nov. 2, 2023, 15 pages.
International Search Report and Written Opinion dated Nov. 18, 2021 in International Application No. PCT/KR2021/010368, pp. 17.
RU2021132331—Office Action mailed on Nov. 3, 2023, 16 pages.
AU2020248612—Notice of Acceptance mailed on Sep. 21, 2023, 4 pages.
Bazhenova et al., Cancer Research, vol. 77, No. 13, suppl. Abstract No. CT032.
U.S. Appl. No. 17/052,952—Non-Final Office Action mailed on Jun. 13, 2024, 20 pages.
Office Action dated Jul. 9, 2021 in Taiwanese Patent Application No. 109119328.
JP2021567961—Office Action mailed on Jul. 2, 2024, 6 pages.
CN202180003323.4—Office Action mailed on Jul. 10, 2024, 12 pages.
Tavares, A. et al., "Inhibition of the checkpoint protein PD-1 by the therapeutic antibody pembrolizumab outlined by quantum chemistry", Scientific Reports, vol. 8, Issue 1840, pp. 1-13.
CONC20210012380—Office Action mailed on Jan. 11, 2024, 16 pages.
EA202192588—Office Action mailed on Sep. 29, 2023, 8 pages.
IDP00202108509—Office Action mailed on Sep. 27, 2023, 4 pages.
PA93644-01—Search Report mailed on Mar. 29, 2022, 8 pages.
VN1-2021-06635—Office Action mailed on Feb. 26, 2024, 3 pages.
U.S. Appl. No. 16/628,258—Notice of Allowance mailed on Jul. 16, 2024, 8 pages.
U.S. Appl. No. 17/608,729—Requirement for Restriction/Election mailed on May 14, 2024, 5 pages.
Appendix A Sequence Alignment, 2024.
Office Action issued in Australian Patent Application No. 2020248612 on Nov. 8, 2022.
Office Action issued in Canadian Patent Application No. 3131052 on Oct. 19, 2022.
Office Action issued in Chile Patent Application No. 202102464 on May 4, 2023.
English Translation of Office Action issued in Chile Patent Application No. 202102464 on May 4, 2023.
Opposition filed Against Ecuador Patent Application No. SENADI-2021-70640 on Feb. 14, 2022.
English Translation of Opposition filed Against Ecuador Patent Application No. SENADI-2021-70640 on Feb. 14, 2022.
Office Action Issued in Georgian Patent Application No. AP202015767 on Apr. 3, 2023.
English Translation of Office Action issued in Japanese Patent Application No. 2020569741 on Aug. 23, 2022.
Office Action issued in Korean Patent Application No. 20227016935 on Aug. 28, 2022.
English Translation of Office Action issued in Korean Patent Application No. 20227016935 on Aug. 28, 2022.
Office Action issued in Saudia Arabia Patent Application No. 521430398 on Feb. 25, 2023.
English Translation of Office Action issued in Saudia Arabia Patent Application No. 521430398 on Feb. 25, 2023.
JP2023026863—Notice of Reasons for Refusal mailed on Mar. 12, 2024, 10 pages.
CN202080003052.8—First Office Action mailed on Jun. 27, 2023, 12 pages.
CN202080003052.8—Second Office Action mailed on Mar. 2, 2024, 11 pages.
CN202310416462.0—First Office Action mailed on Mar. 5, 2024, 8 pages.
EESR Issued in counterpart European Patent Application No. 21743774.8 on Jan. 4, 2023, 20 pages.
Seffernick, J.L., et al., "Melamine Deaminase and Atrazine Chlorohydrolase: 98 Percent Identical but Functionally Different", Journal of Bacteriology, 201, vol. 183, No. 8, Publisher: American Society for Microbiology, 2405-2410 pages.
Locke, K.W., et al., "Enhanze drug delivery technology: a novel approach to subcutaneous administration using recombinant human hyaluronidase PH20", Drug Delivery, 2019, DOI:10.1080/10717544.2018.1551442, vol. 26, No. 1, Publisher: Taylor & Francis, 98-106 pages.
Muchmore, D.B., et al., "Accelerating and Improving the Consistency of Rapid-Acting Analog Insulin Absorption and Action for Both Subcutaneous Injection and Continuous Subcutaneous Infusion Using Recombinant Human Hyaluronidase", Journal of Diabetes Sciene and Technology, 2012, vol. 6, No. 4, Publisher: Diabetes Technology Societ, 764-772 pages.
Restelli, V., et al., "The Effect of Dissolved Oxygen on the Production and the Glycosylation Profile of Recombinant Human Erythropoietin Produced From CHO Cells", Biotechnol Bioeng, 2006, vol. 9, 481-494 pages.
Schilling, S., et al., "Heterologous Expression and Characterization of Human Glutaminy Cyclase: Evidence for a Disulfide Bond with Importance for Catalytic Activity", Biochemistry, 2002, vol. 41, Publisher: American Chemical Society, 10849-10857 pages.
CA3173310—Office action mailed on Dec. 20, 2023, 5 pages.
CN202180030097.9—First Office Action mailed on Jan. 6, 2024, 19 pages.
JP2022559471—Final Notification of Reasons forRefusal mailed on Mar. 19, 2024, 8 pages.
KR1020210103530—Written Decision on Registration mailed on Dec. 15, 2023, 6 pages.
Zarrintaj et al.,"Poloxamer: A versatile tri-block copolymer for biomedical applications", Acta Biomaterialia, 2020, vol. 110, 37-67 pages.

(56) References Cited

OTHER PUBLICATIONS

Strickley et al.,"A review of formulations of commercially available antibodies", Journal of Pharmaceutical Sciences, 2021, vol. 110, 2590-2608 pages.
International Search Report dated Feb. 2, 2023 in International Application No. PCT/KR2022/016709, 14 pages.
CN201980023392.4—Second Office Action mailed on Feb. 8, 2024, 8 pages.
Office Action Issued in Japanese Patent Application No. 2022559471 on Oct. 11, 2023, 15 pages.
Chica et al., "Semi-rational approaches to engineering enzyme activity: combining the benefits of directed evolution and rational design" Current Opinion Biotechnology, vol. 16, Issue 4, 2005, 378-784 pages.
Wasserman, R.L., "Overview of recombinant human hyaluronidase-faciliated subcutaneous infusion of IgG in primary immunodeficiencies", Immunotherapy, 2014, vol. 6, No. 5, Publisher: Future Medicin, 553-567 pages.
Opposition filed Jan. 13, 2022 by Laboratorios Legrand S.A. against Columbian Patent Application No. NC2021/0012380, pp. 21.
Opposition dated Jul. 5, 2022 by Asociacion de Laboratorios Farmaceuticos (ALAFAR) Against Ecuadorian Application No. SENADI-2021-70640, pp. 3.
NCBI Reference Sequence, hyaluronidase PH-20 precursor [Cavia porcelius], NP_001166492.1, Jun. 21, 2021 pp. 2 (downloaded Aug. 24, 2023).
Broun, P., et al., "Catalytic Plasticity of Fatty Acid Modification Enzymes Underlying Chemical Diversity of Plant D Lipids", Science, 1998, pp. 1315-1317, vol. 282, No. 13, Publisher: www.sciencemag.org.
Hiromoto, Y., et al., "An Activity-Straining Method on Filtration Paper Enables High-Throughput Screening of Temperature-Sensitive and Inactive Mutations of Rice-Amylase for Improvement of Rice Grain Quality", Plant and Cell Physiology, 2017, pp. 658-667, vol. 58, No. 4, Publisher: Japanese Society of Plant Physiologists.
Office Action issued on Dec. 2, 2022 in counterpart Canadian Patent Application No. 2137324, pp. 4.
Office Action issued on Oct. 17, 2022 in counterpart Russian Patent Application No. 2021132331, pp. 18.
Whisstock, J.D., et al., "Prediction of protein function from protein sequence and structure", Quarterly Reviews of Biophysics, 2003, vol. 36, No. 3, Publisher: Cambridge University Press, pp. 307-340.
Pakula, A., et al., "Genetic Analysis of Protein Stability and Function", Annu. Rev. Genet., 1898, vol. 23, pp. 289-310.
Witkowski, A., et al., "Conversion of a Beta-Ketoacyl Synthase to a Malonyl Decarboxylase by Replacement of the Active-Site Cysteine with Glutamine", Biochemistry, 1999, vol. 38, Publisher: American Chemical Society, pp. 11643-11650.
"GenBank: AAC6067.2, PH-20 (*Homo sapiens*)", NCBI , Jun. 5, 2000, pp. 2.
Singh et al., "Protein Engineering Approaches in the Post-Genomic Era", Current Protein and Peptide Science, 2017 , vol. 18 , pp. 1-11.
Office Action issued on Sep. 5, 2022 in counterpart Taiwan Patent Application 110130965, pp. 6.
Borys, M.C., et al., "Culture pH Affects Expression Rates and Glycosylation of Recombinant Mouse Placental Lactogen Proteins by Chinese Hamster Ovary (CHO) Cells", Biotechnology, 1993, vol. 11, Publisher: Nature Publishing Group, pp. 720-724.
Borys, M.C., et al., "Ammonia Affects the Glycosylation Patterns of Recombinant Mouse Placental Lactogen-| by Chinese Hamster Overy Cells in a pH-Dependent Manner", Biotechnology and Bioengineering, 1994, vol. 43, Publisher: John Wiley & Sons, Inc, pp. 505-514.
Clark, K.J.R., et al., "Temperature Effects on Product-Quality-Related Enzymes in Batch CHO Cell Cultures Producing Recombinant tPA", Biotechnol. Prog., 2004, vol. 20, Publisher: American Chemical Society, pp. 1888-1892.
Clement, WA, et al., "The use of hyaluronidase in nasal infiltration: prospective randomized controlled pilot study", The Journal of Laryngology & Otology, 2003, vol. 117, pp. 614-618.
Harb, G., et al., "Safety and pharmakokinetics of subcutaneous ceftriaxone administered with or without recombinant human hyaluronidase (rHuPH20) versus intravenous ceftriaxone administration in adult volunteers", Current Medical Research & Opinion, 2010, vol. 26, No. 2, Publisher: CMRO, pp. 279-288.
Harris, R.J., et al., "Commercial Manufacturing Scale Formulation and Analytical Characterization of Therapeutic Recombinant Antibodies", Drug Development Research, 2004 , vol. 61, pp. 137-154.
Krantz, E.M., "Low-Dose Intramuscular Ketamine and Hyaluronidase for Induction of Anaesthesia in NonPemedicated Children", S.A. Med. J., 1980, vol. 58, No. 4, pp. 161-162.
Tachibana, H., et al., "Changes of monosacharide availability of human hybridoma lead to alteration of biological properties of human monoclonal antibody", Cytotechnology, 1994, vol. 16, Publisher: Kiuwer Academic Publishers, pp. 151-157.
Bittner, B., et al., "Subcutaneous Administration of Biotherapeutics—An Overview of Current Challenges and Opportunities", BioDrugs, 2018, pp. 425-440, vol. 32, Publisher: CrossMark.
Bookbinder, L.H., et al., "A Recombinant Human Enzyme for Enhanced Interstitial Transport of Therapeutics", Journal of Controlled Release, 2006, pp. 230-241, vol. 114.
Borders, C., et al., "Purification and Partial Characterization of Testicular Hyaluronidase", The Journal of Biological Chemistry, Jul. 10, 1968, pp. 3756-3762, vol. 243, No. 13.
Chao, K., et al., "Structure of Human Hyaluronidase-1, a Hyaluronan Hydrolyzing Enzyme Involved in Tumor Growth and Angiogenesis", Biochemistry, 2007, pp. 6911-6920, vol. 46.
Chen, K., et al., "Constitutive Expression of Recombinant Human Hyaluronidase PH20 by Pichia Pastoris", Journal of Bioscience and Bioengineering, 2016, pp. 1-6.
"Opposition Against Columbian Patent Application NC20210012380", Oct. 20, 2021.
"Opposition Against Columbian Patent Application NC20210012380", , Page(s) ENG.
Frost, G., "Recombinant Human Hyaluronidase (rHuPH20): An Enabling Platform for Subcutaneous Drug and Fluid Administration", Expert Opin Drug Deliv, 2007, pp. 427-440, vol. 4, No. 4.
Hofinger, E., et al., "Kinetics of Hyal-1 and PH-20 Hyaluronidases: Comparison of Minimal Substrates and Analysis of the Transglycosylation Reaction", Glycobiology, 2007, pp. 963-971, vol. 17, No. 9.
Kreidieh, F., et al., "Overview, Prevention and Management of Chemotherapy Extravasation", World Journal of Clinical Oncology, Feb. 10, 2016, pp. 87-97, vol. 7, No. 1.
Shpilberg, O., et al., "Subcutaneous administration of rituximab (MabThera) and trastuzumab (Herceptin) using hyaluronidase", Britich Journal of Cancer, 2013, pp. 1556-1561, vol. 109.
Thomas, J., et al., "The Infuse-Morphine IIB Study: Use of Recombinant Human Hyaluronidase (rHuPH20) to Enhance the Absorption of Subcutaneous Morphone in Healthy Volunteers", Journal of Pain and Symptom Management, Nov. 2009, pp. 673-682, vol. 38, No. 5.
CN201980023392.4—Decision of Final Rejection mailed on May 17, 2024, 10 pages.
CA3,093,885—Office Action mailed on Jun. 3, 2024, 4 pages.
JP2022-211105—Decision of Rejection mailed on May 14, 2024, 3 pages.
H. Johansen, et al., "High-level production of fully active human alpha 1-antitrypsin in *Escherichia coli.*" Mol. Biol. Med. (1987) vol. 4, pp. 291-305.
J.H. Dunham, et al., "GPR37 Surface Expression Enhancement via N-Terminal Truncation or Protein-Protein Interactions", Biochemistry (2009) 48, pp. 10286-10297.
M. Wei, et al., "N-terminal truncations on L1 proteins of human papillomaviruses promote their soluble expression in *Escherichia coli* and self-assembly in vitro", Emerging Microbes & Infections (2018) vol. 7, pp. 160.
M. F. Meyer, et al., "The soluble hyaluronidase from bull testes is a fragment of the membrane-bound PH-20 enzyme", FEBS letter (1997) vol. 413, pp. 385-388.

(56) References Cited

OTHER PUBLICATIONS

International Search Report and Written Opinion dated Sep. 21, 2023 in International Application No. PCT/KR2023/008621, pp. 15.
AU2021320569—Examination Report No. 1 mailed on Apr. 30, 2024, 3 pages.
CN2021800300979—First Office Action mailed on Jan. 6, 2024, 18 pages.
MX/a/2020/009824—Office Action mailed on Jun. 10, 2024, 16 pages.
TW111145281—First Office Action mailed on May 29, 2024, 16 pages.
TW111128188—First Office Action mailed on May 29, 2024, 24 pages.
TW110102662—Office Action mailed on May 3, 2024, 22 pages.
TW111136059—Office Action mailed on May 3, 2024, 20 pages.
JP2022211105—Notice of Reasons for Refusal mailed on Nov. 14, 2023, 17 pages.
CN201980023392.4—First Office Action mailed on Jun. 17, 2023, 9 pages.
KR20207002955—Written Decision on Registration mailed on Aug. 25, 2020, 16 pages.
JP2020500863—Notice of Reasons for Refusal mailed on Jan. 25, 2022, 7 pages.
JP2020500863—Notice of Reasons for Refusal mailed on May 24, 2022, 6 pages.
JP2020500863—Notice of Reasons for Refusal mailed on Jun. 15, 2021, 12 pages.
EP19827585—Supplementary European search report mailed on Mar. 31, 2021, 9 pages.
JP2022211105—Decision of Rejection mailed on May 14, 2024, 2 pages.
CA3,093,885—Examiner Requisition mailed on Sep. 1, 2021, 4 pages.
CA3,093,885—Examiner Requisition mailed on Oct. 3, 2022, 6 pages.
AU2019311658—Examination Report No. 1 mailed on Jun. 17, 2022, 3 pages.
AU2019311658—Notice of Acceptance mailed on Oct. 11, 2022, 3 pages.
KR20227013211—Request for the Submission of an Opinion mailed on Apr. 26, 2024, 7 pages.
CN202180003323.4—First Office Action mailed on Nov. 27, 2023, 14 pages.
EP21743774—Supplementary European search report mailed on Jan. 4, 2023, 20 pages.
JP2021567961—Decision of Rejection mailed on Nov. 14, 2023, 8 pages.
JP2021567961—Notice of Reasons for Refusal mailed on Apr. 11, 2023, 6 pages.
AU2021211348—Examination Report No. 1 mailed on Mar. 17, 2023, 3 pages.
AU2021211348—Examination Report No. 2 mailed on Jul. 11, 2023, 5 pages.
AU2021211348—Notice of Acceptance mailed on Sep. 21, 2023, 4 pages.
CA3,137,324—Examiner Requisition mailed on Dec. 2, 2022, 4 pages.
CA3,137,324—Examiner Requisition mailed on May 6, 2024, 6 pages.
KR20207030248—Written Decision on Registration mailed on Dec. 22, 2023, 5 pages.
KR20207030248—Notice of Final Rejection mailed on Jul. 27, 2023, 6 pages.
KR20207030248—Request for the Submission of an Opinion mailed on Aug. 28, 2022, 14 pages.
KR20227016935—Written Decision on Registration mailed on Dec. 21, 2022, 6 pages.
JP2022068166—Notice of Reasons for Refusal mailed on Jun. 21, 2022, 8 pages.
JP2022068166—Decision to Grant a Patent mailed on Oct. 4, 2022, 5 pages.
JP2020569741—Notice of Reasons for Refusal mailed on Nov. 16, 2021, 8 pages.
JP2020569741—Decision to Grant a Patent mailed on May 16, 2023, 5 pages.
CN202310416462.0—Notification of grant of patent right for invention mailed on May 16, 2024, 3 pages.
AU2020248612—Examination Report No. 3 mailed on Nov. 8, 2023, 2 pages.
Guan et al., "Efficient PD-L1 gene silence promoted by hyaluronidase for cancer immunotherapy", Journal of Controlled Release, 293, 2019, pp. 104-112.
U.S. Appl. No. 19/374,092, filed Oct. 30, 2025.
Gong et al., "Combination systemic therapies with immune checkpoint inhibitors in pancreatic cancer: overcoming resistance to single-agent checkpoint blockade," Clinical and Transitional Medicine 7(32):1-16 (2018).
Kumar et al., "Emerging Therapies in the Management of Advanced-Stage Gastric Cancer," Frontiers in Pharmacology Review 13(9):1-24 (2018).
Kang et al (BioProcess International, 2016, vol. 14, pp. 40-45) (Year: 2016).
Whitaker et al (Journal of Pharmaceutical Sciences, 2017, vol. 106, pp. 3230-3241) (Year: 2017).
Halozyme Therapeutics, "A Study of PEGylated Recombinant Human Hyaluronidase (PEGPH20) with Pembrolizumab in Participants with Selected Hyaluronan High Solid Tumors," National Library of Medicine—ClinicalTrials.govID—NCT02563548, pp. 1-25 (2020).
Merck Sharp & Dohme LLC, "A Phase 1 Randomized Clinical Study of Pembrolizumab (MK-3475) to Evaluate the Relative Bioavailability of Subcutaneous Injection Versus Intravenous Infusion in Participants With Advanced Melanoma (Keynote-555)," Clinical Trails NCT03665597, Protocol ID 3475-555, Version 5 (Nov. 30, 2018).
Merck Sharp & Dohme LLC, "A Phase 1 Randomized Clinical Study of Pembrolizumab (MK-3475) to Evaluate the Relative Bioavailability of Subcutaneous Injection Versus Intravenous Infusion in Participants With Advanced Melanoma (Keynote-555)," Clinical Trails NCT03665597, Protocol ID 3475-555, Version 6 (Dec. 27, 2018).
Merck Sharp & Dohme LLC, "A Phase 1 Randomized Clinical Study of Pembrolizumab (MK-3475) to Evaluate the Relative Bioavailability of Subcutaneous Injection Versus Intravenous Infusion in Participants With Advanced Melanoma (Keynote-555)," Clinical Trails NCT03665597, Protocol ID 3475-555, Version 7 (Jan. 28, 2019).
Merck Sharp & Dohme LLC, "A Phase 1 Randomized Clinical Study of Pembrolizumab (MK-3475) to Evaluate the Relative Bioavailability of Subcutaneous Injection Versus Intravenous Infusion in Participants With Advanced Melanoma (Keynote-555)," Clinical Trails NCT03665597, Protocol ID 3475-555, Version 8 (Mar. 8, 2019).
Merck Sharp & Dohme LLC, "A Phase 1 Randomized Clinical Study of Pembrolizumab (MK-3475) to Evaluate the Relative Bioavailability of Subcutaneous Injection Versus Intravenous Infusion in Participants With Advanced Melanoma (Keynote-555)," Clinical Trails NCT03665597, Protocol ID 3475-555, Version 9 (Mar. 14, 2019).
Merck Sharp & Dohme LLC, "A Phase 1 Randomized Clinical Study of Pembrolizumab (MK-3475) to Evaluate the Relative Bioavailability of Subcutaneous Injection Versus Intravenous Infusion in Participants With Advanced Melanoma (Keynote-555)," Clinical Trails NCT03665597, Protocol ID 3475-555, Version 10 (Mar. 22, 2019).
Merck Sharp & Dohme LLC, "A Phase 1 Randomized Clinical Study of Pembrolizumab (MK-3475) to Evaluate the Relative Bioavailability of Subcutaneous Injection Versus Intravenous Infusion in Participants With Advanced Melanoma (Keynote-555)," Clinical Trails NCT03665597, Protocol ID 3475-555, Version 11 (Apr. 11, 2019).

(56) References Cited

OTHER PUBLICATIONS

Merck Sharp & Dohme LLC, "A Phase 1 Randomized Clinical Study of Pembrolizumab (MK-3475) to Evaluate the Relative Bioavailability of Subcutaneous Injection Versus Intravenous Infusion in Participants With Advanced Melanoma (Keynote-555)," Clinical Trails NCT03665597, Protocol ID 3475-555, Version 12 (Jul. 24, 2019).

Merck Sharp & Dohme LLC, "A Phase 1 Randomized Clinical Study of Pembrolizumab (MK-3475) to Evaluate the Relative Bioavailability of Subcutaneous Injection Versus Intravenous Infusion in Participants With Advanced Melanoma (Keynote-555)," Clinical Trails NCT03665597, Protocol ID 3475-555, Version 13 (Aug. 8, 2019).

Merck Sharp & Dohme LLC, "A Phase 1 Randomized Clinical Study of Pembrolizumab (MK-3475) to Evaluate the Relative Bioavailability of Subcutaneous Injection Versus Intravenous Infusion in Participants With Advanced Melanoma (Keynote-555)," Clinical Trails NCT03665597, Protocol ID 3475-555, Version 14 (Aug. 23, 2019).

Merck Sharp & Dohme LLC, "A Phase 1 Randomized Clinical Study of Pembrolizumab (MK-3475) to Evaluate the Relative Bioavailability of Subcutaneous Injection Versus Intravenous Infusion in Participants With Advanced Melanoma (Keynote-555)," Clinical Trails NCT03665597, Protocol ID 3475-555, Version 15 (Sep. 4, 2019).

Merck Sharp & Dohme LLC, "A Phase 1 Randomized Clinical Study of Pembrolizumab (MK-3475) to Evaluate the Relative Bioavailability of Subcutaneous Injection Versus Intravenous Infusion in Participants With Advanced Melanoma (Keynote-555)," Clinical Trails NCT03665597, Protocol ID 3475-555, Version 16 (Oct. 10, 2019).

Merck Sharp & Dohme LLC, "A Phase 1 Randomized Clinical Study of Pembrolizumab (MK-3475) to Evaluate the Relative Bioavailability of Subcutaneous Injection Versus Intravenous Infusion in Participants With Advanced Melanoma (Keynote-555)," Clinical Trails NCT03665597, Protocol ID 3475-555, Version 17 (Oct. 18, 2019).

Merck Sharp & Dohme LLC, "A Phase 1 Randomized Clinical Study of Pembrolizumab (MK-3475) to Evaluate the Relative Bioavailability of Subcutaneous Injection Versus Intravenous Infusion in Participants With Advanced Melanoma (Keynote-555)," Clinical Trails NCT03665597, Protocol ID 3475-555, Version 18 (Jan. 31, 2020).

Merck Sharp & Dohme LLC, "A Phase 1 Randomized Clinical Study of Pembrolizumab (MK-3475) to Evaluate the Relative Bioavailability of Subcutaneous Injection Versus Intravenous Infusion in Participants With Advanced Melanoma (Keynote-555)," Clinical Trails NCT03665597, Protocol ID 3475-555, Version 19 (Feb. 25, 2020).

CN202180030097.9—Second Office Action mailed on Oct. 13, 2024.

Benkert et al., "Toward the Estimation of the Absolute Quality of Individual Protein Structure Models," Bioinfomatics, 27:343-350 (2010).

Swiss Model Printout of PH20 Model with D320K Mutation, printed Nov. 9, 2024 (Exhibit 1070 in PGR2025-00003).

Swiss Model Printout of PH20 Model with D320H Mutation, printed Nov. 9, 2024 (Exhibit 1071 in PGR2025-00003).

U.S. Appl. No. 19/532,992, filed Feb. 6, 2026.

* cited by examiner

| | Aggregation temperature (°C) |
|---|---|
| Formulation 1 | 74°C |
| Formulation 2 | 76°C |
| Formulation 3 | 76°C |
| Formulation 4 | 76°C |

[ Formulation 9 ]

Aggregation Point (°C): 77.0

[ Formulation 10 ]

Aggregation Point (°C): 78.0

| | 1 | 2 | 3 | Mean | STDEV | %RSD |
|---|---|---|---|---|---|---|
| **Formulation 8** | 78°C | 79°C | 78°C | **78.3**°C | 0.6 | 0.7 |
| **Formulation 9** | 78°C | 77°C | 77°C | **77.3**°C | 0.6 | 0.7 |
| **Formulation 10** | 77°C | 78°C | 78°C | **77.7**°C | 0.6 | 0.7 |

FIG. 8B

PHARMACEUTICAL COMPOSITION FOR SUBCUTANEOUS ADMINISTRATION CONTAINING HUMAN HYALURONIDASE PH20 VARIANT AND DRUG

CROSS-REFERENCE TO RELATED APPLICATIONS

This application is a continuation under 35 U.S.C. § 120 of U.S. Patent Application 17/052,952 filed Nov. 4, 2020, which in turn is a U.S. national phase under the provisions of 35 U.S.C. § 371 of International Patent Application No. PCT/KR2020/003975 filed Mar. 24, 2020, which in turn claims priority under 35 U.S.C. § 119 of Korean Patent Application No. 10-2019-0033880 filed Mar. 25, 2019. The disclosures of such international patent application and Korean priority patent application are hereby incorporated herein by reference in their respective entireties, for all purposes.

REFERENCE TO SEQUENCE LISTING SUBMITTED VIA PATENT CENTER

This application includes an electronically submitted sequence listing in .txt format. The .txt file contains a sequence listing entitled "Q303375SeqListingST25. txt" created on Oct. 12, 2025 and is 188,730 bytes in size. The sequence listing contained in this .txt file is part of the specification and is hereby incorporated by reference herein in its entirety.

TECHNICAL FIELD

The present invention relates to a pharmaceutical composition including a human hyaluronidase PH20 variant having enhanced enzymatic activity and thermal stability and one or more drugs, and a method of treating a disease using the same.

The pharmaceutical composition according to the present invention may preferably be used for subcutaneous administration (subcutaneous injection).

BACKGROUND ART

Drugs which should be administered in a high dose or in a large amount, especially antibody drugs and the like, are generally administered via intravenous injection, and such injection takes about 90 minutes or longer, an additional preparation procedure should be accompanied for intravenous injection, thus both a patient, doctors and medical staff are inconvenienced, and additional costs are incurred. In contrast, subcutaneous injections have the advantage of enabling immediate administration, but the absorption rate is relatively low compared to intravenous injections, and when the injection amount is 3 to 5 mL or more, it may cause swelling and pain at the injection site, as absorption occurs slowly. As for this reason, subcutaneous injections of protein therapeutic agents is usually limited to solution injection of a small amount of 2 mL or less. However, upon subcutaneous administration (subcutaneous administration or subcutaneous injection) of hyaluronidase along with a therapeutic drug, hyaluronic acid distributed in the extracellular matrix is hydrolyzed by the action of hyaluronidase, and thus the viscosity of the subcutaneous area decreases and the permeability of a substance increases, and therefore, a high dose and a large amount of medicine can easily be delivered into the body.

There are six types of hyaluronidase genes in humans: Hyal1, Hyal2, Hyal3, Hyal4, HyalPS1, and PH20/SPAM1. Hyal1 and Hyal2 are expressed in most tissues, and PH20/SPAM1 (hereinafter, referred to as PH20) is expressed in the sperm cell membrane and the acrosomal membrane. HyalPS1 is not expressed because it is a pseudogene. PH20 is an enzyme (EC 3.2.1.35) that cleaves β-1,4 bonds between N-acetylglucosamine and glucuronic acid, which are sugars constituting hyaluronic acid. Human hyaluronidase PH20 has an optimal pH of 5.5 but exhibits some activity even at a pH level of 7 to 8, whereas other human hyaluronidases, including Hyal1, have an optimal pH of 3 to 4 and have very weak activity at a pH level of 7 to 8. The pH of subcutaneous areas in a human is about 7.4, which is substantially neutral, and thus, among various types of hyaluronidases, PH20 is widely applied in clinical use. Examples of the clinical use of PH20 include subcutaneous injection of an antibody therapeutic agent, use as an eye relaxant and an anesthetic injection additive in ophthalmic surgery, use in increasing the access of an anticancer therapeutic agent to the tumor cells by hydrolyzing hyaluronic acid in the extracellular matrix of tumor cells, and use in promoting the resorption of body fluids and blood, which are excessively present in tissue, etc.

Meanwhile, currently commercially available PH20 is in a form extracted from the testes of cattle or sheep. Examples thereof include AMPHADASE® (bovine hyaluronidase) and VITRASE® (sheep hyaluronidase).

Bovine testicular hyaluronidase (BTH) is obtained by removing a signal peptide and 56 amino acids on the C-terminus from bovine wild-type PH20 during post-translational modification of proteins. BTH is also a glycoprotein and has a mannose content of 5% and a glucosamine content of 2.2%, based on the total constitution thereof including amino acids (Borders and Raftery, 1968). When animal-derived hyaluronidase is repeatedly administered to the human body at a high dose, a neutralizing antibody can be produced, and other animal-derived biomaterials contained as impurities in addition to PH20 may cause an allergic reaction. In particular, the use of PH20 extracted from cattle is limited due to concern over mad cow disease. In order to overcome these problems, studies on recombinant human PH20 proteins have been conducted.

Recombinant human PH20 proteins have been reported to be expressed in yeast (*P. pastoris*), DS-2 insect cells, animal cells, and the like (Chen et al., 2016, Hofinger et al., 2007). The recombinant PH20 proteins produced in insect cells and yeast differ from human PH20 in terms of the pattern of N-glycosylation during post-translational modification of proteins.

Among hyaluronidases, the protein structures of Hyal1 (PDB ID: 2PE4) (Chao et al., 2007) and bee venom hyaluronidase (PDB ID: 1FCQ, 1FCU, 1FCV) have been identified. Hyal1 is composed of two domains, a catalytic domain and an EGF-like domain, and the catalytic domain is in the form of (β/α) 8, in which an alpha helix and a beta-strand, which characterize the secondary structure of the protein, are each repeated eight times (Chao et al., 2007). The EGF-like domain is conserved in all variants in which the C-terminus of Hyal1 is spliced differently. The amino acid sequences of Hyal1 and PH20 are 35.1% identical, and the protein tertiary structure of PH20 has not yet been found.

In a structural/functional relationship study of human PH20, the C-terminal region of PH20 was found to be important for protein expression and enzymatic activity, and in particular, it has been reported that termination of the C-terminus with amino acids 477 to 483 is important for enzymatic expression and activity (Frost, 2007). The activity of full-length PH20 (amino acids 1 to 509) or a pH20 variant having a C-terminus truncated at amino acid position 467 or beyond was merely 10% or less of that of a pH20 variant having a C-terminus truncated at one site among positions 477 to 483 (Frost, 2007). Halozyme Therapeutics developed rHuPH20 (amino acids 36 to 482), which is a recombinant protein in the form in which the C-terminus of mature PH20 was truncated at Y482 (Bookbinder et al., 2006; Frost, 2007).

Meanwhile, although research is ongoing to develop various therapeutic drugs in the form of subcutaneous injection formulations using human PH20, the problem of low stability of human PH20 itself still remains unsolved.

Against this technical background, the inventors of the present invention found that human PH20 variants, including one or more amino acid substitutions in an alpha-helix 8 region (S347 to C381) and a linker region (A333 to R346) between alpha-helix 7 and alpha-helix 8 in the amino acid sequence of wild-type hyaluronidase PH20, and in which portion(s) of amino acids located at the N-terminus and/or the C-terminus of PH20 are truncated, had excellent enzymatic activity and thermal stability, and thus filed a patent application therefor (PCT/KR 2019/009215).

The inventors of the present application also found that the PH20 variants according to the present invention may be applied to pharmaceutical compositions or formulations including drugs, e.g., antibody drugs, particularly high-dose anti-HER2 antibodies or immune checkpoint antibodies, and accordingly, pharmaceutical compositions and formulations according to the present invention including a PH20 variant along with a drug such as anti-HER2 antibodies or immune checkpoint antibodies can be used for subcutaneous administration, and the activities of a drug such as antibody drugs and the PH20 variant are very stable and can be maintained for a long time, thus completing the present invention.

SUMMARY OF THE INVENTION

It is an object of the present invention to provide a novel pharmaceutical composition including a PH20 variant having enhanced enzymatic activity and thermal stability along with a drug, wherein the thermal stability and activity of the drug and the PH20 variant can be maintained for a long time, particularly a pharmaceutical composition that can be used for subcutaneous administration.

It is another object of the present invention to provide a method of treating a disease including administering the pharmaceutical composition according to the present invention to a subject in need of treatment.

In accordance with the present invention, the above and other objects can be accomplished by the provision of a pharmaceutical composition including (a) a drug and (b) a PH20 variant.

The PH20 variant included in the pharmaceutical composition according to the present invention is characterized by including one or more amino acid residue substitutions selected from the group consisting of S343E, M345T, K349E, L353A, L354I, N356E, and I361T in wild-type human PH20 having an amino acid sequence of SEQ ID NO: 1, and is characterized by further including amino acid substitution(s) in one or more regions selected from an alpha-helix 8 region (S347 to C381) and/or a linker region (A333 to R346) between alpha-helix 7 and alpha-helix 8, wherein portion(s) of amino acid residues located at an N-terminus and/or a C-terminus are selectively truncated.

The pharmaceutical composition according to the present invention may further include one or more selected from pharmaceutically acceptable additives, particularly a buffer, a stabilizer, and a surfactant.

The pharmaceutical composition according to the present invention may be used in the form of an injection formulation for subcutaneous administration.

BRIEF DESCRIPTION OF DRAWINGS

FIG. 8B illustrates the results of measuring protein aggregation temperatures.

DETAILED DESCRIPTION AND PREFERRED EMBODIMENTS OF THE INVENTION

Figure 1A:
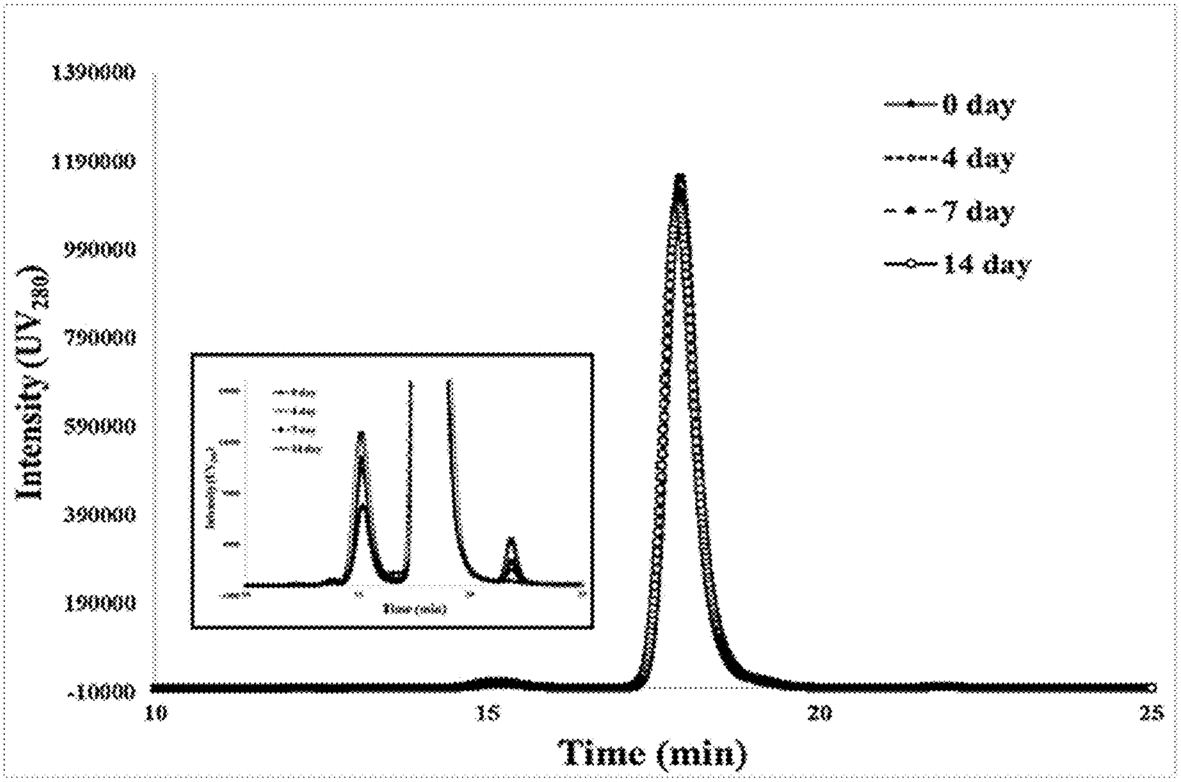
FIG. 1A illustrates size-exclusion chromatography chromatograms of trastuzumab in a stability test under harsh conditions at 45° C.

Unless defined otherwise, all technical and scientific terms used herein have the same meanings as those generally understood by a person having ordinary skill in the art to which the invention pertains. In general, the nomenclature used herein is well known and commonly used in the art.

A working example of the present invention relates to a pharmaceutical composition including (a) a drug and (b) a PH20 variant, and the pharmaceutical composition according to the present invention may be used for the prevention or treatment of a disease and is preferably used for subcutaneous administration.

The human PH20 variant included in the pharmaceutical composition according to the present invention is characterized by substitution(s) of portion(s) of amino acid residues in the region corresponding to an alpha-helix region and/or a linker region thereof, preferably an alpha-helix 8 region (S347 to C381) and/or a linker region (A333 to R346) between alpha-helix 7 and alpha-helix 8, more preferably an amino acid region among T341 to N363, and most preferably an amino acid region corresponding to T341 to 1361, L342 to 1361, S343 to I361, 1344 to 1361, M345 to 1361, or M345 to N363, in the amino acid sequence of wild-type PH20 (having the amino acid sequence of SEQ ID NO: 1), preferably mature wild-type PH20 (having the sequence consisting of L36 to S490 in the amino acid sequence of SEQ ID NO: 1).

In the present invention, "mature wild-type PH20" refers to a protein consisting of amino acid residues L36 to S490 of SEQ ID NO: 1, which lacks M1 to T35, which form a signal peptide, and A491 to L509, which are not related to the substantial function of PH20, in the amino acid sequence of wild-type PH20 having the sequence of SEQ ID NO: 1.

TABLE 1

| Amino acid sequence of wild-type PH20 (SEQ ID NO: 1) |
|---|
| MGVLKFKHIFFRSFVKSSGVSQIVFTFLLIPCCLTLNFRAPPVIPNVPFL |
| WAWNAPSEFCLGKFDEPLDMSLFSFIGSPRINATGQGVTIFYVDRLGYYP |
| YIDSITGVTVNGGIPQKISLQDHLDKAKKDITFYMPVDNLGMAVIDWEEW |
| RPTWARNWKPKDVYKNRSIELVQQQNVQLSLTEATEKAKQEFEKAGKDFL |
| VETIKLGKLLRPNHLWGYYLFPDCYNHHYKKPGYNGSCFNVEIKRNDDLS |
| WLWNESTALYPSIYLNTQQSPVAATLYVRNRVREAIRVSKIPDAKSPLPV |
| FAYTRIVFTDQVLKFLSQDELVYTFGETVALGASGIVIWGTLSIMRSMKS |
| CLLLDNYMETILNPYIINVTLAAKMCSQVLCQEQGVCIRKNWNSSDYLHL |
| NPDNFAIQLEKGGKFTVRGKPTLEDLEQFSEKFYCSCYSTLSCKEKADVK |
| DTDAVDVCIADGVCIDAFLKPPMETEEPQIFYNASPSTLSATMFIVSILF |
| LIISSVASL |

Specifically, the PH20 variant or fragment thereof included in the pharmaceutical composition according to the present invention includes one or more mutations, preferably amino acid residue substitutions, selected from the group consisting of S343E, M345T, K349E, L353A, L354I, N356E, and I361T, and most preferably one or more amino acid residue substitutions selected from the group consisting of L354I and N356E, in wild-type PH20 having the sequence of SEQ ID NO: 1.

In the present invention, the term "PH20 variant" is intended to include mutation of portion(s) of amino acid residues, preferably substitution of amino acid residues in the sequence of wild-type human PH20, as well as the deletion of portion(s) of amino acid residues at the N-terminus and/or the C-terminus together with such substitution of amino acid residues, and is used with substantially the same meaning as the expression PH20 variant or a fragment thereof.

The inventors of the present invention have verified novel PH20 variants or fragments thereof with increased enzymatic activity and thermal stability compared to wild-type PH20 can be provided through previous studies, based on experimental results in which, enzymatic activity and a protein aggregation temperature (Tagg.) at a neutral pH increase, when the amino acid sequences of an alpha-helix 8 region and a linker region between alpha-helix 7 and alpha-helix 8 of human PH20 are partially substituted with the amino acid sequences of an alpha-helix 8 region and a linker region between alpha-helix 7 and alpha-helix 8 of Hyal1 with high hydrophilicity.

Accordingly, the PH20 variant included in the pharmaceutical composition according to the present invention includes one or more amino acid residue substitutions selected from the group consisting of S343E, M345T, K349E, L353A, L354I, N356E, and I361T, preferably one or more amino acid residue substitutions selected from the group consisting of L354I and N356E, in the amino acid sequence of wild-type PH20 (having the amino acid sequence of SEQ ID NO: 1), preferably mature wild-type PH20 (having a sequence consisting of L36 to S490 in the amino acid sequence of SEQ ID NO: 1), in which one or more amino acid residues in the region corresponding to an alpha-helix region and/or a linker region thereof, preferably in an alpha-helix 8 region (S347 to C381) and/or a linker region (A333 to R346) between alpha-helix 7 and alpha-helix 8, more preferably in an amino acid region corresponding to T341 to N363, T341 to 1361, L342 to I361, S343 to I361, 1344 to 1361, M345 to 1361, or M345 to N363, are substituted.

Particularly, in the PH20 variant included in the pharmaceutical composition according to the present invention, the alpha-helix 8 region (S347 to C381) and/or the linker region (A333 to R346) between alpha-helix 7 and alpha-helix 8 of wild-type PH20, preferably mature wild-type PH20, may be substituted with portion(s) of amino acid residues in the amino acid sequence of a corresponding region of Hyal1 having the sequence of SEQ ID NO: 51 (see Tables 2 and 3), but not limited thereto.

TABLE 2

| Amino acid sequence of wild-type Hyal1 (SEQ ID NO: 51) |
|---|
| MAAHLLPICALFLTLLDMAQGFRGPLLPNRPFTTVWNANTQWCLERHGVD |
| VDVSVFDVVANPGQTFRGPDMTIFYSSQLGTYPYYTPTGEPVFGGLPQNA |
| SLIAHLARTFQDILAAIPAPDFSGLAVIDWEAWRPRWAFNWDTKDIYRQR |
| SRALVQAQHPDWPAPQVEAVAQDQFQGAARAWMAGTLQLGRALRPRGLWG |
| FYGFPDCYNYDFLSPNYTGQCPSGIRAQNDQLGWLWGQSRALYPSIYMPA |
| VLEGTGKSQMYVQHRVAEAFRVAVAAGDPNLPVLPYVQIFYDTTNHFLPL |
| DELEHSLGESAAQGAAGVVLWVSWENTRTKESCQAIKEYMDTTLGPFILN |
| VTSGALLCSQALCSGHGRCVRRTSHPKALLLLNPASFSIQLTPGGGPLSL |
| RGALSLEDQAQMAVEFKCRCYPGWQAPWCERKSMW |

TABLE 3

Comparison between alpha helixes and amino acid sequences of PH20 and Hyal1

| Alpha helix | Amino acid sequence of PH20 | Amino acid sequence of Hyal1 |
|---|---|---|
| Alpha-helix 1 | P56 to D65 | N39 to G48 |
| Alpha-helix 3 | S119 to M135 | S101 to I117 |
| Alpha-helix 4' | K161 to N176 | K144 to H159 |
| Alpha-helix 4 | S180 to R211 | P163 to R194 |
| Alpha-helix 5 | F239 to S256 | P222 to S239 |
| Alpha-helix 6 | A274 to D293 | K257 to G277 |
| Alpha-helix 7 | S317 to G332 | P299 to G314 |
| Alpha-helix 8 | S347 to C381 | T329 to C363 |

More specifically, the PH20 variant or fragment thereof included in the pharmaceutical composition according to the present invention includes an amino acid residue substitution of L354I and/or N356E in the amino acid sequence of wild-type PH20, preferably mature wild-type PH20, and preferably further includes an amino acid residue substitution at one or more positions selected from T341 to N363, particularly at one or more positions selected from the group consisting of T341, L342, S343, 1344, M345, S347, M348, K349, L352, L353, D355, E359, 1361, and N363, but is not limited thereto, and more preferably, further includes one or more amino acid residue substitutions selected from the group consisting of T341S, L342W, S343E, 1344N, M345T, S347T, M348K, K349E, L352Q, L353A, D355K, E359D, 1361T, and N363G, but is not limited thereto.

Preferably, the PH20 variant or fragment thereof included in the pharmaceutical composition according to the present invention may include amino acid residue substitutions of M345T, S347T, M348K, K349E, L352Q, L353A, L354I, D355K, N356E, E359D, and I361T, and may further include one or more amino acid residue substitutions selected from the group consisting of T341S, L342W, S343E, 1344N, and N363G, but is not limited thereto.

More preferably, the PH20 variant or fragment thereof included in the pharmaceutical composition according to the present invention may include, but is not limited to, any one substitution selected from the group consisting of the following:

(a) T341S, L342W, S343E, 1344N, M345T, S347T, M348K, K349E, L352Q, L353A, L354I, D355K, N356E, E359D, and I361T;
(b) L342W, S343E, 1344N, M345T, S347T, M348K, K349E, L352Q, L353A, L354I, D355K, N356E, E359D, and I361T;
(c) M345T, S347T, M348K, K349E, L352Q, L353A, L354I, D355K, N356E, E359D, and I361T;
(d) M345T, S347T, M348K, K349E, L352Q, L353A, L354I, D355K, N356E, E359D, I361T, and N363G;
(e) I344N, M345T, S347T, M348K, K349E, L352Q, L353A, L354I, D355K, N356E, E359D, and I361T; and
(f) S343E, 1344N, M345T, S347T, M348K, K349E, L352Q, L353A, L354I, D355K, N356E, E359D, and I361T.

In the present invention, an expression, which is described by one-letter amino acid residue code together with numbers, such as "S347", means the amino acid residue at the corresponding position in the amino acid sequence of SEQ ID NO: 1.

For example, "S347" means that the amino acid residue at position 347 in the amino acid sequence of SEQ ID NO: 1 is serine. In addition, "S347T" means that serine at position 347 of SEQ ID NO: 1 is substituted with threonine.

The PH20 variant included in the pharmaceutical composition according to the present invention is interpreted as including variants in which the amino acid residue at a specific amino acid residue position is conservatively substituted.

As used herein, the term "conservative substitution" refers to modifications of a PH20 variant that involves the substitution of one or more amino acids with amino acids having similar biochemical properties that do not cause loss of the biological or biochemical function of the corresponding PH20 variant.

A "conservative amino acid substitution" is one in which the amino acid residue is replaced with an amino acid residue having a similar side chain. Families of amino acid residues having similar side chains have been defined and are well known in the art. These families include amino acids with basic side chains (e.g., lysine, arginine, and histidine), amino acids with acidic side chains (e.g., aspartic acid and glutamic acid), amino acids with uncharged polar side chains (e.g., glycine, asparagine, glutamine, serine, threonine, tyrosine, and cysteine), amino acids with nonpolar side chains (e.g., alanine, valine, leucine, isoleucine, proline, phenylalanine, methionine, and tryptophan), amino acids with beta-branched side chains (e.g., threonine, valine, and isoleucine), and amino acids with aromatic side chains (e.g., tyrosine, phenylalanine, tryptophan, and histidine).

It is anticipated that the PH20 variant included in the pharmaceutical composition according to the present invention will still retain the activity thereof despite having conservative amino acid substitutions.

In addition, the PH20 variant or fragment thereof included in the pharmaceutical composition according to the present invention is interpreted as including PH20 variants or fragments thereof having substantially the same function and/or effect as those/that of the PH20 variant or the fragment thereof according to the present invention, and having an amino acid sequence homology of at least 80% or 85%, preferably at least 90%, more preferably at least 95%, and most preferably at least 99% with the PH20 variant or fragment thereof according to the present invention.

The PH20 variants according to the present invention have increased expression levels and an increased protein refolding rate, thereby having increased thermal stability in animal cells compared to mature wild-type PH20. Furthermore, the enzymatic activity of the PH20 variants exceeded or was similar to that of mature wild-type PH20 despite the increase in thermal stability.

Meanwhile, it is known that, when portion(s) of amino acids at the C-terminus, such as S490, of the mature wild-type PH20 are additionally truncated, the enzymatic activity is reduced. However, the PH20 variants according to the present invention exhibited increased thermal stability and increased or similar enzymatic activities compared to the mature wild-type PH20 despite the C-terminus sequences being additionally truncated compared to the mature wild-type PH20. In addition, the PH20 variants maintained enzymatic activities thereof despite the mature wild-type PH20 having sequences that up to five amino acids were truncated from the N-terminus, which indicates that residues starting from P41 of the N-terminus played an important role in protein expression and enzymatic activity.

Accordingly, the PH20 variant included in the pharmaceutical composition according to the present invention includes portion(s) of amino acid residue substitutions in the alpha-helix 8 region (S347 to C381) and/or the linker region (A333 to R346) between alpha-helix 7 and alpha-helix 8 of wild-type PH20, and further includes portion(s) of amino acid residue deletions at the C-terminus and/or the N-terminus, but is not limited thereto.

In one embodiment, the PH20 variant included in the pharmaceutical composition according to the present invention may include portion(s) of amino acid residue deletions at the N-terminus resulting from truncation before an amino acid residue selected from the group consisting of M1 to P42 at the N-terminus of the amino acid sequence of SEQ ID NO: 1, preferably before an amino acid residue L36, N37, F38, R39, A40, P41, or P42, and/or portion(s) of amino acid residue deletions at the C-terminus resulting from truncation after an amino acid residue selected from the group consisting of V455 to W509 at the C-terminus, preferably after an amino acid residue selected from the group consisting of V455 to S490, and most preferably, after an amino acid reside V455, C458, D461, C464, 1465, D466, A467, F468, K470, P471, P472, M473, E474, T475, E476, P478, 1480, Y482, A484, P486, T488, or S490.

The expression "truncation before L36, N37, F38, R39, A40, P41, or P42 at the N-terminus" means, respectively, that amino acid residues from M1 to T35 immediately before L36, amino acid residues from M1 to L36 immediately before N37, amino acid residues from M1 to N37 immediately before F38, amino acid residues from M1 to F38 immediately before R39, amino acid residues from M1 to R39 immediately before A40, amino acid residues from M1 to A40 immediately before P41, or amino acid residues from M1 to P41 immediately before P42 in the amino acid sequence of SEQ ID NO: 1 are removed by truncation. The expression "truncation before M1 at the N-terminus of SEQ ID NO: 1" means that no truncation occurs at the N-terminus.

In addition, the expression "truncation after V455, C458, D461, C464, 1465, D466, A467, F468, K470, P471, P472, M473, E474, T475, E476, P478, 1480, Y482, A484, P486, T488, or S490 of the C-terminus" means truncation and removal of the amino acid residues starting with the amino acid residue which immediately follows V455, C458, D461, C464, 1465, D466, A467, F468, K470, P472, M473, E474, T475, E476, P478, 1480, Y482, A484, P486, T488, or S490, respectively, in the sequence of SEQ ID NO: 1. For example, occurrence of truncation after S490 means occurrence of truncation between S490 and A491.

Preferably, the human PH20 variant included in the pharmaceutical composition according to the present invention may have an amino acid sequence selected from the group consisting of the amino acid sequences of SEQ ID NOS: 5 to 50, more preferably the amino acid sequence of SEQ ID NO: 44, but is not limited thereto. In PH20 variants constructed in specific working examples according to the present invention, the sequences of substituted or truncated amino acids are shown in Table 4 below.

TABLE 4

Amino acid sequences of PH20 variants according to the present disclosure and the substitution/cleavage properties thereof

| Name | Sequence Number | Substitution | Sequence |
|---|---|---|---|
| HM1 | 5 | 12 amino acid substitutions of M345T, S347T, M348K, K349E, L352Q, L353A, L354I, D355K, N356E, E359D, I361T, and N363G. | LNFRAPPVIPNVPFLWAWNAPSEFCLGKFDEPLDM<br>SLFSFIGSPRINATGQGVTIFYVDRLGYYPYIDSI<br>TGVTVNGGIPQKISLQDHLDKAKKDITFYMPVDNL<br>GMAVIDWEEWRPTWARNWKPKDVYKNRSIELVQQQ<br>NVQLSLTEATEKAKQEFEKAGKDFLVETIKLGKLL<br>RPNHLWGYYLFPDCYNHHYKKPGYNGSCFNVEIKR<br>NDDLSWLWNESTALYPSIYLNTQQSPVAATLYVRN<br>RVREAIRVSKIPDAKSPLPVFAYTRIVFTDQVLKF<br>LSQDELVYTFGETVALGASGIVIWGTLSITRTKES<br>CQAIKEYMDTTLGPYIINVTLAAKMCSQVLCQEQG<br>VCIRKNWNSSDYLHLNPDNFAIQLEKGGKFTVRGK<br>PTLEDLEQFSEKFYCSCYSTLSCKEKADVKDTDAV<br>DVCIADGVCIDAFLKPPMETEEPQIFYNASPSTLS |
| HM2 | 6 | 7 amino acid substitutions of Y365F, I367L, L371S, A372G, K374L, M375L, and V379A. | LNFRAPPVIPNVPFLWAWNAPSEFCLGKFDEPLDM<br>SLFSFIGSPRINATGQGVTIFYVDRLGYYPYIDSI<br>TGVTVNGGIPQKISLQDHLDKAKKDITFYMPVDNL<br>GMAVIDWEEWRPTWARNWKPKDVYKNRSIELVQQQ<br>NVQLSLTEATEKAKQEFEKAGKDFLVETIKLGKLL<br>RPNHLWGYYLFPDCYNHHYKKPGYNGSCFNVEIKR<br>NDDLSWLWNESTALYPSIYLNTQQSPVAATLYVRN<br>RVREAIRVSKIPDAKSPLPVFAYTRIVFTDQVLKF<br>LSQDELVYTFGETVALGASGIVIWGILSITRTKES<br>CQAIKEYMDTTLNPFILNVTSGALLCSQALCQEQG<br>VCIRKNWNSSDYLHLNPDNFAIQLEKGGKFTVRGK<br>PTLEDLEQFSEKEYCSCYSTLSCKEKADVKDTDAV<br>DVCIADGVCIDAFLKPPMETEEPQIFYNASPSTLS |
| HM3 | 7 | 19 amino acid substitutions of M345T, S347T, M348K, K349E, L352Q, L353A, L354I, D355K, N356E, E359D I361T, N363G Y365F, I367L L371S, A372G, K374L, M375L, and V379A. | LNFRAPPVIPNVPFLWAWNAPSEFCLGKFDEPLDM<br>SLFSFIGSPRINATGQGVTIFYVDRLGYYPYIDSI<br>TGVTVNGGIPQKISLQDHLDKAKKDITFYMPVDNL<br>GMAVIDWEEWRPTWARNWKPKDVYKNRSIELVQQQ<br>NVQLSLTEATEKAKQEFEKAGKDFLVETIKLGKLL<br>RPNHLWGYYLFPDCYNHHYKKPGYNGSCFNVEIKR<br>NDDLSWLWNESTALYPSIYLNTQQSPVAATLYVRN<br>RVREAIRVSKIPDAKSPLPVFAYTRIVFTDQVLKF<br>LSQDELVYTFGETVALGASGIVIWGTLSITRTKES<br>CQAIKEYMDTTLGPFILNVTSGALLCSQALCQEQG<br>VCIRKNWNSSDYLHLNPDNFAIQLEKGGKFTVRGK<br>PTLEDLEQFSEKFYCSCYSTLSCKEKADVKDTDAV<br>DVCIADGVCIDAFLKPPMETEEPQIFYNASPSTLS |
| HM4 | 8 | 17 amino acid substitutions of G340V, T341S, L342W, S343E, I344N, M345T, S347T, M348K, K349E, L352Q, L353A, L354I, D355K, N356E, E359D, I361T, and N363G. | LNFRAPPVIPNVPFLWAWNAPSEFCLGKFDEPLDM<br>SLFSFIGSPRINATGQGVTIFYVDRLGYYPYIDSI<br>TGVTVNGGIPQKISLQDHLDKAKKDITFYMPVDNL<br>GMAVIDWEEWRPTWARNWKPKDVYKNRSIELVQQQ<br>NVQLSLTEATEKAKQEFEKAGKDFLVETIKLGKLL<br>RPNHLWGYYLFPDCYNHHYKKPGYNGSCFNVEIKR<br>NDDLSWLWNESTALYPSIYLNTQQSPVAATLYVRN<br>RVREAIRVSKIPDAKSPLPVFAYTRIVFTDQVLKF<br>LSQDELVYTFGETVALGASGIVIWVSWENTRTKES<br>CQAIKEYMDTTLGPYIINVTLAAKMCSQVLCQEQG<br>VCIRKNWNSSDYLHLNPDNFAIQLEKGGKFTVRGK<br>PTLEDLEQFSEKFYCSCYSTLSCKEKADVKDTDAV<br>DVCIADGVCIDAFLKPPMETEEPQIFYNASPSTLS |
| HM6 | 9 | 11 amino acid residue substitutions of M345T, S347T, M348K, K349E, L352Q, L353A, L354I, D355K, N356E, E359D, and I361T. | LNFRAPPVIPNVPFLWAWNAPSEFCLGKFDEPLDM<br>SLFSFIGSPRINATGQGVTIFYVDRLGYYPYIDSI<br>TGVTVNGGIPQKISLQDHLDKAKKDITFYMPVDNL<br>GMAVIDWEEWRPTWARNWKPKDVYKNRSIELVQQQ<br>NVQLSLTEATEKAKQEFEKAGKDFLVETIKLGKLL<br>RPNHLWGYYLFPDCYNHHYKKPGYNGSCFNVEIKR<br>NDDLSWLWNESTALYPSIYLNTQQSPVAATLYVRN<br>RVREAIRVSKIPDAKSPLPVFAYTRIVFTDQVLKF<br>LSQDELVYTFGETVALGASGIVIWGILSITRTKES<br>CQAIKEYMDTTLNPYIINVTLAAKMCSQVLCQEQG<br>VCIRKNWNSSDYLHLNPDNFAIQLEKGGKFTVRGK<br>PTLEDLEQFSEKEYCSCYSTLSCKEKADVKDTDAV<br>DVCIADGVCIDAFLKPPMETEEPQIFYNASPSTLS |
| HM7 | 10 | 16 amino acid substitutions of G340V, T341S, L342W, | LNFRAPPVIPNVPFLWAWNAPSEFCLGKFDEPLDM<br>SLFSFIGSPRINATGQGVTIFYVDRLGYYPYIDSI<br>TGVTVNGGIPQKISLQDHLDKAKKDITFYMPVDNL |

TABLE 4-continued

Amino acid sequences of PH20 variants according to the present disclosure and the substitution/cleavage properties thereof

| Name | Sequence Number | Substitution | Sequence |
|---|---|---|---|
| | | S343E, I344N, M345T, S347T, M348K, K349E, L352Q, L353A, L354I, D355K, N356E, E359D, and I361T. | GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTFGETVALGASGIVIWVSWENTRTKES CQAIKEYMDTTLNPYIINVTLAAKMCSQVLCQEQG VCIRKNWNSSDYLHLNPDNFAIQLEKGGKFTVRGK PTLEDLEQFSEKFYCSCYSTLSCKEKADVKDTDAV DVCIADGVCIDAFLKPPMETEEPQIFYNASPSTLS |
| HM8 | 11 | 12 amino acids substitutions of I344N, M345T, S347T, M348K, K349E, L352Q, L353A, L354I, D355K, N356E, E359D, and I361T. | LNFRAPPVIPNVPFLWAWNAPSEFCLGKFDEPLDM SLFSFIGSPRINATGQGVTIFYVDRLGYYPYIDSI TGVTVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTFGETVALGASGIVIWGTLSNTRTKES CQAIKEYMDTTLNPYIINVTLAAKMCSQVLCQEQG VCIRKNWNSSDYLHLNPDNFAIQLEKGGKFTVRGK PTLEDLEQFSEKEYCSCYSTLSCKEKADVKDTDAV DVCIADGVCIDAFLKPPMETEEPQIFYNASPSTLS |
| HM9 | 12 | 13 amino acids substitutions of S343E, I344N, M345T, S347T, M348K, K349E, L352Q, L353A, L354I, D355K, N356E, E359D, and I361T. | LNFRAPPVIPNVPFLWAWNAPSEFCLGKFDEPLDM SLFSFIGSPRINATGQGVTIFYVDRLGYYPYIDSI TGVTVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTFGETVALGASGIVIWGTLENTRTKES CQAIKEYMDTTLNPYIINVTLAAKMCSQVLCQEQG VCIRKNWNSSDYLHLNPDNFAIQLEKGGKFTVRGK PTLEDLEQFSEKEYCSCYSTLSCKEKADVKDTDAV DVCIADGVCIDAFLKPPMETEEPQIFYNASPSTLS |
| HM10 | 13 | 14 amino acid residue substitutions of L342W, S343E, I344N, M345T, S347T, M348K, K349E, L352Q, L353A, L354I, D355K, N356E, E359D, and I361T. | LNFRAPPVIPNVPFLWAWNAPSEFCLGKFDEPLDM SLFSFIGSPRINATGQGVTIFYVDRLGYYPYIDSI TGVTVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTFGETVALGASGIVIWGTWENTRTKES CQAIKEYMDTTLNPYIINVTLAAKMCSQVLCQEQG VCIRKNWNSSDYLHLNPDNFAIQLEKGGKFTVRGK PTLEDLEQFSEKEYCSCYSTLSCKEKADVKDTDAV DVCIADGVCIDAFLKPPMETEEPQIFYNASPSTLS |
| HM11 | 14 | 13 amino acid residue substitutions of M345T, S347T, M348K, K349E, L352Q, L353A, L354I, D355K, N356E, E359D, I361T, Y365F, and I367L. | LNFRAPPVIPNVPFLWAWNAPSEFCLGKFDEPLDM SLFSFIGSPRINATGQGVTIFYVDRLGYYPYIDSI TGVTVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTFGETVALGASGIVIWGTLSITRTKES CQAIKEYMDTTLNPFILNVTLAAKMCSQVLCQEQG VCIRKNWNSSDYLHTNTDNFAIQLEKGGKFTVRGK PTLEDLEQFSEKEYCSCYSTLSCKEKADVKDTDAV DVCIADGVCIDAFLKPPMETEEPQIFYNASPSTLS |
| HM12 | 15 | 15 amino acid residue substitutions of M345T, S347T, M348K, K349E, L352Q, L353A, | LNFRAPPVIPNVPFLWAWNAPSEFCLGKFDEPLDM SLFSFIGSPRINATGQGVTIFYVDRLGYYPYIDSI TGVTVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR |

TABLE 4-continued

Amino acid sequences of PH20 variants according to the present disclosure and the substitution/cleavage properties thereof

| Name | Sequence Number | Substitution | Sequence |
|---|---|---|---|
| | | L354I, D355K,<br>N356E, E359D,<br>I361T, Y365F,<br>I367L, L371S, and<br>A372G. | NDDLSWLWNESTALYPSIYLNTQQSPVAATLYVRN<br>RVREAIRVSKIPDAKSPLPVFAYTRIVFTDQVLKF<br>LSQDELVYTFGETVALGASGIVIWGTLSI**T**R**TKE**S<br>C**QAIKE**YM**D**T**T**LNP**F**I**L**NVT**SG**AKMCSQVLCQEQG<br>VCIRKNWNSSDYLHLNPDNFAIQLEKGGKFTVRGK<br>PTLEDLEQFSEKFYCSCYSTLSCKEKADVKDTDAV<br>DVCIADGVCIDAFLKPPMETEEPQIFYNASPSTLS |
| HM13 | 16 | 11 amino acid<br>residue<br>substitutions of<br>M345T, S347T,<br>M348K, K349E,<br>L352Q, L353A,<br>L354I, D355K,<br>N356E, E359D, and<br>I361T, and<br>truncation before<br>residue F38 at the<br>N-terminus. | FRAPPVIPNVPFLWAWNAPSEFCLGKFDEPLDMSL<br>FSFIGSPRINATGQGVTIFYVDRLGYYPYIDSITG<br>VTVNGGIPQKISLQDHLDKAKKDITFYMPVDNLGM<br>AVIDWEEWRPTWARNWKPKDVYKNRSIELVQQQNV<br>QLSLTEATEKAKQEFEKAGKDFLVETIKLGKLLRP<br>NHLWGYYLFPDCYNHHYKKPGYNGSCFNVEIKRND<br>DLSWLWNESTALYPSIYLNTQQSPVAATLYVRNRV<br>REAIRVSKIPDAKSPLPVFAYTRIVFTDQVLKFLS<br>QDELVYTFGETVALGASGIVIWGTLSI**T**R**TKE**SC**Q**<br>**AIKE**YM**D**T**T**LNPYIINVTLAAKMCSQVLCQEQGVC<br>IRKNWNSSDYLHLNPDNFAIQLEKGGKFTVRGKPT<br>LEDLEQFSEKFYCSCYSTLSCKEKADVKDTDAVDV<br>CIADGVCIDAFLKPPMETEEPQIFYNASPSTLS |
| HM14 | 17 | 11 amino acids<br>substitutions of<br>M345T, S347T,<br>M348K, K349E,<br>L352Q, L353A,<br>L354I, D355K,<br>N356E, E359D, and<br>I361T, and<br>truncation after<br>the carboxyl group<br>of I465. | LNFRAPPVIPNVPFLWAWNAPSEFCLGKFDEPLDM<br>SLFSFIGSPRINATGQGVTIFYVDRLGYYPYIDSI<br>TGVTVNGGIPQKISLQDHLDKAKKDITFYMPVDNL<br>GMAVIDWEEWRPTWARNWKPKDVYKNRSIELVQQQ<br>NVQLSLTEATEKAKQEFEKAGKDFLVETIKLGKLL<br>RPNHLWGYYLFPDCYNHHYKKPGYNGSCFNVEIKR<br>NDDLSWLWNESTALYPSIYLNTQQSPVAATLYVRN<br>RVREAIRVSKIPDAKSPLPVFAYTRIVFTDQVLKF<br>LSQDELVYTFGETVALGASGIVIWGTLSI**T**R**TKE**S<br>C**QAIKE**YM**D**T**T**LNPYIINVTLAAKMCSQVLCQEQG<br>VCIRKNWNSSDYLHLNPDNFAIQLEKGGKFTVRGK<br>PTLEDLEQFSEKFYCSCYSTLSCKEKADVKDTDAV<br>DVCIADGVCI |
| HM15 | 18 | 11 amino acids ae<br>substitutions of<br>M345T, S347T,<br>M348K, K349E,<br>L352Q, L353A,<br>L354I, D355K,<br>N356E, E359D, and<br>I361T, and<br>truncation after<br>the carboxyl group<br>of F468. | LNFRAPPVIPNVPFLWAWNAPSEFCLGKFDEPLDM<br>SLFSFIGSPRINATGQGVTIFYVDRLGYYPYIDSI<br>TGVTVNGGIPQKISLQDHLDKAKKDITFYMPVDNL<br>GMAVIDWEEWRPTWARNWKPKDVYKNRSIELVQQQ<br>NVQLSLTEATEKAKQEFEKAGKDFLVETIKLGKLL<br>RPNHLWGYYLFPDCYNHHYKKPGYNGSCFNVEIKR<br>NDDLSWLWNESTALYPSIYLNTQQSPVAATLYVRN<br>RVREAIRVSKIPDAKSPLPVFAYTRIVFTDQVLKF<br>LSQDELVYTFGETVALGASGIVIWGTLSI**T**R**TKE**S<br>C**QAIKE**YM**D**T**T**LNPYIINVTLAAKMCSQVLCQEQG<br>VCIRKNWNSSDYLHLNPDNFAIQLEKGGKFTVRGK<br>PTLEDLEQFSEKFYCSCYSTLSCKEKADVKDTDAV<br>DVCIADGVCIDAF |
| HM16 | 19 | 11 amino acids<br>substitutions of<br>M345T, S347T,<br>M348K, K349E,<br>L352Q, L353A,<br>L354I, D355K,<br>N356E, E359D, and<br>I361T, and<br>truncation after<br>the carboxyl group<br>of P471. | LNFRAPPVIPNVPFLWAWNAPSEFCLGKFDEPLDM<br>SLFSFIGSPRINATGQGVTIFYVDRLGYYPYIDSI<br>TGVTVNGGIPQKISLQDHLDKAKKDITFYMPVDNL<br>GMAVIDWEEWRPTWARNWKPKDVYKNRSIELVQQQ<br>NVQLSLTEATEKAKQEFEKAGKDFLVETIKLGKLL<br>RPNHLWGYYLFPDCYNHHYKKPGYNGSCFNVEIKR<br>NDDLSWLWNESTALYPSIYLNTQQSPVAATLYVRN<br>RVREAIRVSKIPDAKSPLPVFAYTRIVFTDQVLKF<br>LSQDELVYTFGETVALGASGIVIWGTLSI**T**R**TKE**S<br>C**QAIKE**YM**D**T**T**LNPYIINVTLAAKMCSQVLCQEQG<br>VCIRKNWNSSDYLHLNPDNFAIQLEKGGKFTVRGK<br>PTLEDLEQFSEKFYCSCYSTLSCKEKADVKDTDAV<br>DVCIADGVCIDAFLKP |
| HM17 | 20 | Substitution of<br>amino acids L36 to<br>V47 with FRGPLLPNR<br>(SEQ ID NO: 52),<br>and<br>11 amino acid<br>substitutions of<br>M345T, S347T,<br>M348K, K349E, | **FRGPLLPNR**PFLWAWNAPSEFCLGKFDEPLDMSLF<br>SFIGSPRINATGQGVTIFYVDRLGYYPYIDSITGV<br>TVNGGIPQKISLQDHLDKAKKDITFYMPVDNLGMA<br>VIDWEEWRPTWARNWKPKDVYKNRSIELVQQQNVQ<br>LSLTEATEKAKQEFEKAGKDFLVETIKLGKLLRPN<br>HLWGYYLFPDCYNHHYKKPGYNGSCFNVEIKRNDD<br>LSWLWNESTALYPSIYLNTQQSPVAATLYVRNRVR<br>EAIRVSKIPDAKSPLPVFAYTRIVFTDQVLKFLSQ<br>DELVYTFGETVALGASGIVIWGTLSI**T**R**TKE**SC**QA** |

TABLE 4-continued

Amino acid sequences of PH20 variants according to the present disclosure and the substitution/cleavage properties thereof

| Name | Sequence Number | Substitution | Sequence |
|---|---|---|---|
| | | L352Q, L353A, L354I, D355K, N356E, E359D, and I361T. | **IKE**YM**D**T**T**LNPYIINVTLAAKMCSQVLCQEQGVCI<br>RKNWNSSDYLHLNPDNFAIQLEKGGKFTVRGKPTL<br>EDLEQFSEKFYCSCYSTLSCKEKADVKDTDAVDVC<br>IADGVCIDAFLKPPMETEEPQIFYNASPSTLS |
| HM18 | 21 | Substitution of amino acids L36 to A52 with FRGPLLPNRPFTTV (SEQ ID NO: 53), and 11 amino acid substitutions of M345T, S347T, M348K, K349E, L352Q, L353A, L354I, D355K, N356E, E359D, and I361T. | **FRGPLLPNRPFTTV**WNAPSEFCLGKFDEPLDMSLF<br>SFIGSPRINATGQGVTIFYVDRLGYYPYIDSITGV<br>TVNGGIPQKISLQDHLDKAKKDITFYMPVDNLGMA<br>VIDWEEWRPTWARNWKPKDVYKNRSIELVQQQNVQ<br>LSLTEATEKAKQEFEKAGKDFLVETIKLGKLLRPN<br>HLWGYYLFPDCYNHHYKKPGYNGSCFNVEIKRNDD<br>LSWLWNESTALYPSIYLNTQQSPVAATLYVRNRVR<br>EAIRVSKIPDAKSPLPVFAYTRIVFTDQVLKFLSQ<br>DELVYTFGETVALGASGIVIWGTLSI**T**R**TKE**SC**QA**<br>**IKE**YM**D**T**T**LNPYIINVTLAAKMCSQVLCQEQGVCI<br>RKNWNSSDYLHLNPDNFAIQLEKGGKFTVRGKPTL<br>EDLEQFSEKFYCSCYSTLSCKEKADVKDTDAVDVC<br>IADGVCIDAFLKPPMETEEPQIFYNASPSTLS |
| HM19 | 22 | 14 amino acid residue substitutions of L342W, S343E, I344N, M345T, S347T, M348K, K349E, L352Q, L353A, L354I, D355K, N356E, E359D, and I361T, and truncations before residue F38 at the N-terminus and after residue K470 at the C-terminus. | FRAPPVIPNVPFLWAWNAPSEFCLGKFDEPLDMSL<br>FSFIGSPRINATGQGVTIFYVDRLGYYPYIDSITG<br>VTVNGGIPQKISLQDHLDKAKKDITFYMPVDNLGM<br>AVIDWEEWRPTWARNWKPKDVYKNRSIELVQQQNV<br>QLSLTEATEKAKQEFEKAGKDFLVETIKLGKLLRP<br>NHLWGYYLFPDCYNHHYKKPGYNGSCFNVEIKRND<br>DLSWLWNESTALYPSIYLNTQQSPVAATLYVRNRV<br>REAIRVSKIPDAKSPLPVFAYTRIVFTDQVLKFLS<br>QDELVYTFGETVALGASGIVIWGT**WENT**R**TKE**SC**Q**<br>**AIKE**YM**D**T**T**LNPYIINVTLAAKMCSQVLCQEQGVC<br>IRKNWNSSDYLHLNPDNFAIQLEKGGKFTVRGKPT<br>LEDLEQFSEKFYCSCYSTLSCKEKADVKDTDAVDV<br>CIADGVCIDAFLK |
| HM20 | 23 | 14 amino acid residue substitutions of L342W, S343E, I344N, M345T, S347T, M348K, K349E, L352Q, L353A, L354I, D355K, N356E, E359D, and I361T, and truncations before residue F38 at the N-terminus and after residue F468 at the C-terminus. | FRAPPVIPNVPFLWAWNAPSEFCLGKFDEPLDMSL<br>FSFIGSPRINATGQGVTIFYVDRLGYYPYIDSITG<br>VTVNGGIPQKISLQDHLDKAKKDITFYMPVDNLGM<br>AVIDWEEWRPTWARNWKPKDVYKNRSIELVQQQNV<br>QLSLTEATEKAKQEFEKAGKDFLVETIKLGKLLRP<br>NHLWGYYLFPDCYNHHYKKPGYNGSCFNVEIKRND<br>DLSWLWNESTALYPSIYLNTQQSPVAATLYVRNRV<br>REAIRVSKIPDAKSPLPVFAYTRIVFTDQVLKFLS<br>QDELVYTEGETVALGASGIVIWGT**WENT**R**TKE**SC**Q**<br>**AIKE**YM**D**T**T**LNPYIINVTLAAKMCSQVLCQEQGVC<br>IRKNWNSSDYLHLNPDNFAIQLEKGGKFTVRGKPT<br>LEDLEQFSEKFYCSCYSTLSCKEKADVKDTDAVDV<br>CIADGVCIDAF |
| HM21 | 24 | 15 amino acid residue substitutions of T341S, L342W, S343E, I344N, M345T, S347T, M348K, K349E, L352Q, L353A, L354I, D355K, N356E, E359D, and I361T. | LNFRAPPVIPNVPFLWAWNAPSEFCLGKFDEPLDM<br>SLFSFIGSPRINATGQGVTIFYVDRLGYYPYIDSI<br>TGVTVNGGIPQKISLQDHLDKAKKDITFYMPVDNL<br>GMAVIDWEEWRPTWARNWKPKDVYKNRSIELVQQQ<br>NVQLSLTEATEKAKQEFEKAGKDFLVETIKLGKLL<br>RPNHLWGYYLFPDCYNHHYKKPGYNGSCFNVEIKR<br>NDDLSWLWNESTALYPSIYLNTQQSPVAATLYVRN<br>RVREAIRVSKIPDAKSPLPVFAYTRIVFTDQVLKF<br>LSQDELVYTFGETVALGASGIVIWG**SWENT**R**TKE**S<br>C**QAIKE**YM**D**T**T**LNPYIINVTLAAKMCSQVLCQEQG<br>VCIRKNWNSSDYLHLNPDNFAIQLEKGGKFTVRGK<br>PTLEDLEQFSEKEYCSCYSTLSCKEKADVKDTDAV<br>DVCIADGVCIDAFLKPPMETEEPQIFYNASPSTLS |
| HM24 | 25 | 11 amino acid residue substitutions of M345T, S347T, M348K, K349E, | APPVIPNVPFLWAWNAPSEFCLGKFDEPLDMSLFS<br>FIGSPRINATGQGVTIFYVDRLGYYPYIDSITGVT<br>VNGGIPQKISLQDHLDKAKKDITFYMPVDNLGMAV<br>IDWEEWRPTWARNWKPKDVYKNRSIELVQQQNVQL<br>SLTEATEKAKQEFEKAGKDFLVETIKLGKLLRPNH |

TABLE 4-continued

Amino acid sequences of PH20 variants according to the present disclosure and the substitution/cleavage properties thereof

| Name | Sequence Number | Substitution | Sequence |
| --- | --- | --- | --- |
| | | L352Q, L353A, L354I, D355K, N356E, E359D, and I361T, and truncation before residue A40 at the N-terminus. | LWGYYLFPDCYNHHYKKPGYNGSCFNVEIKRNDDL<br>SWLWNESTALYPSIYLNTQQSPVAATLYVRNRVRE<br>AIRVSKIPDAKSPLPVFAYTRIVFTDQVLKFLSQD<br>ELVYTEGETVALGASGIVIWGTLSITRTKESCQAI<br>KEYMDTTLNPYIINVTLAAKMCSQVLCQEQGVCIR<br>KNWNSSDYLHLNPDNFAIQLEKGGKFTVRGKPTLE<br>DLEQFSEKFYCSCYSTLSCKEKADVKDTDAVDVCI<br>ADGVCIDAFLKPPMETEEPQIFYNASPSTLS |
| HM25 | 26 | 11 amino acid are substitutions of M345T, S347T, M348K, K349E, L352Q, L353A, L354I, D355K, N356E, E359D, and I361T, and truncation before residue P42 at the N-terminus. | PVIPNVPFLWAWNAPSEFCLGKFDEPLDMSLFSFI<br>GSPRINATGQGVTIFYVDRLGYYPYIDSITGVTVN<br>GGIPQKISLQDHLDKAKKDITFYMPVDNLGMAVID<br>WEEWRPTWARNWKPKDVYKNRSIELVQQQNVQLSL<br>TEATEKAKQEFEKAGKDFLVETIKLGKLLRPNHLW<br>GYYLFPDCYNHHYKKPGYNGSCFNVEIKRNDDLSW<br>LWNESTALYPSIYLNTQQSPVAATLYVRNRVREAI<br>RVSKIPDAKSPLPVFAYTRIVFTDQVLKFLSQDEL<br>VYTFGETVALGASGIVIWGTLSITRTKESCQAIKE<br>YMDTTLNPYIINVTLAAKMCSQVLCQEQGVCIRKN<br>WNSSDYLHLNPDNFAIQLEKGGKFTVRGKPTLEDL<br>EQFSEKFYCSCYSTLSCKEKADVKDTDAVDVCIAD<br>GVCIDAFLKPPMETEEPQIFYNASPSTLS |
| HM29 | 27 | 14 amino acid residue substitutions of L342W, S343E, I344N, M345T, S347T, M348K, K349E, L352Q, L353A, L354I, D355K, N356E, E359D, and I361T, and truncations before residue L36 at the N-terminus and after residue A467 at the C-terminus. | LNFRAPPVIPNVPFLWAWNAPSEFCLGKFDEPLDM<br>SLFSFIGSPRINATGQGVTIFYVDRLGYYPYIDSI<br>TGVTVNGGIPQKISLQDHLDKAKKDITFYMPVDNL<br>GMAVIDWEEWRPTWARNWKPKDVYKNRSIELVQQQ<br>NVQLSLTEATEKAKQEFEKAGKDFLVETIKLGKLL<br>RPNHLWGYYLFPDCYNHHYKKPGYNGSCFNVEIKR<br>NDDLSWLWNESTALYPSIYLNTQQSPVAATLYVRN<br>RVREAIRVSKIPDAKSPLPVFAYTRIVFTDQVLKF<br>LSQDELVYTEGETVALGASGIVIWGTWENTRTKES<br>CQAIKEYMDTTLNPYIINVTLAAKMCSQVLCQEQG<br>VCIRKNWNSSDYLHLNPDNFAIQLEKGGKFTVRGK<br>PTLEDLEQFSEKEYCSCYSTLSCKEKADVKDTDAV<br>DVCIADGVCIDA |
| HM30 | 28 | 14 amino acid reside substitutions of L342W, S343E, I344N, M345T, S347T, M348K, K349E, L352Q, L353A, L354I, D355K, N356E, E359D, and I361T, and truncations-before residue L36 at the N-terminal and after residue C464 at the C-terminus. | LNFRAPPVIPNVPFLWAWNAPSEFCLGKFDEPLDM<br>SLFSFIGSPRINATGQGVTIFYVDRLGYYPYIDSI<br>TGVTVNGGIPQKISLQDHLDKAKKDITFYMPVDNL<br>GMAVIDWEEWRPTWARNWKPKDVYKNRSIELVQQQ<br>NVQLSLTEATEKAKQEFEKAGKDFLVETIKLGKLL<br>RPNHLWGYYLFPDCYNHHYKKPGYNGSCFNVEIKR<br>NDDLSWLWNESTALYPSIYLNTQQSPVAATLYVRN<br>RVREAIRVSKIPDAKSPLPVFAYTRIVFTDQVLKF<br>LSQDELVYTFGETVALGASGIVIWGTWENTRTKES<br>CQAIKEYMDTTLNPYIINVTLAAKMCSQVLCQEQG<br>VCIRKNWNSSDYLHLNPDNFAIQLEKGGKFTVRGK<br>PTLEDLEQFSEKEYCSCYSTLSCKEKADVKDTDAV<br>DVCIADGVC |
| HM31 | 29 | 14 amino acid residue substitutions of L342W, S343E, I344N, M345T, S347T, M348K, K349E, L352Q, L353A, L354I, D355K, N356E, E359D, and I361T, and truncations before residue L36 at the N-terminus and after residue D461 at the C-terminus. | LNFRAPPVIPNVPFLWAWNAPSEFCLGKFDEPLDM<br>SLFSFIGSPRINATGQGVTIFYVDRLGYYPYIDSI<br>TGVTVNGGIPQKISLQDHLDKAKKDITFYMPVDNL<br>GMAVIDWEEWRPTWARNWKPKDVYKNRSIELVQQQ<br>NVQLSLTEATEKAKQEFEKAGKDFLVETIKLGKLL<br>RPNHLWGYYLFPDCYNHHYKKPGYNGSCFNVEIKR<br>NDDLSWLWNESTALYPSIYLNTQQSPVAATLYVRN<br>RVREAIRVSKIPDAKSPLPVFAYTRIVFTDQVLKF<br>LSQDELVYTFGETVALGASGIVIWGTWENTRTKES<br>CQAIKEYMDTTLNPYIINVTLAAKMCSQVLCQEQG<br>VCIRKNWNSSDYLHLNPDNFAIQLEKGGKFTVRGK<br>PTLEDLEQFSEKFYCSCYSTLSCKEKADVKDTDAV<br>DVCIAD |

TABLE 4-continued

Amino acid sequences of PH20 variants according to the present disclosure and the substitution/cleavage properties thereof

| Name | Sequence Number | Substitution | Sequence |
|---|---|---|---|
| HM32 | 30 | 14 amino acid residue substitutions of L342W, S343E, I344N, M345T, S347T, M348K, K349E, L352Q, L353A, L354I, D355K, N356E, E359D, and I361T, and truncations before residue L36 at the N-terminus and after residue C458 at the C-terminus. | LNFRAPPVIPNVPFLWAWNAPSEFCLGKFDEPLDMSLFSFIGSPRINATGQGVTIFYVDRLGYYPYIDSITGVTVNGGIPQKISLQDHLDKAKKDITFYMPVDNLGMAVIDWEEWRPTWARNWKPKDVYKNRSIELVQQQNVQLSLTEATEKAKQEFEKAGKDFLVETIKLGKLLRPNHLWGYYLFPDCYNHHYKKPGYNGSCFNVEIKRNDDLSWLWNESTALYPSIYLNTQQSPVAATLYVRNRVREAIRVSKIPDAKSPLPVFAYTRIVFTDQVLKFLSQDELVYTFGETVALGASGIVIWGT**WENT**R**TKE**SC**QAIKE**YM**D**T**T**LNPYIINVTLAAKMCSQVLCQEQGVCIRKNWNSSDYLHLNPDNFAIQLEKGGKFTVRGKPTLEDLEQFSEKFYCSCYSTLSCKEKADVKDTDAVDVC |
| HM33 | 31 | 14 amino acid residue substitutions of L342W, S343E, I344N, M345T, S347T, M348K, K349E, L352Q, L353A, L354I, D355K, N356E, E359D, and I361T, and truncations before residue L36 at the N-terminus and after residue V455 at the C-terminus. | LNFRAPPVIPNVPFLWAWNAPSEFCLGKFDEPLDMSLFSFIGSPRINATGQGVTIFYVDRLGYYPYIDSITGVTVNGGIPQKISLQDHLDKAKKDITFYMPVDNLGMAVIDWEEWRPTWARNWKPKDVYKNRSIELVQQQNVQLSLTEATEKAKQEFEKAGKDFLVETIKLGKLLRPNHLWGYYLFPDCYNHHYKKPGYNGSCFNVEIKRNDDLSWLWNESTALYPSIYLNTQQSPVAATLYVRNRVREAIRVSKIPDAKSPLPVFAYTRIVFTDQVLKFLSQDELVYTFGETVALGASGIVIWGT**WENT**R**TKE**SC**QAIKE**YM**D**T**T**LNPYIINVTLAAKMCSQVLCQEQGVCIRKNWNSSDYLHLNPDNFAIQLEKGGKFTVRGKPTLEDLEQFSEKEYCSCYSTLSCKEKADVKDTDAV |
| HP34 | 32 | 15 amino acid residue substitutions of T341S, L342W, S343E, I344N, M345T, S347T, M348K, K349E, L352Q, L353A, L354I, D355K, N356E, E359D, and I361T, and truncations before residue F38 at the N-terminus and after residue K470 at the C-terminus. | FRAPPVIPNVPFLWAWNAPSEFCLGKFDEPLDMSLFSFIGSPRINATGQGVTIFYVDRLGYYPYIDSITGVTVNGGIPQKISLQDHLDKAKKDITFYMPVDNLGMAVIDWEEWRPTWARNWKPKDVYKNRSIELVQQQNVQLSLTEATEKAKQEFEKAGKDFLVETIKLGKLLRPNHLWGYYLFPDCYNHHYKKPGYNGSCFNVEIKRNDDLSWLWNESTALYPSIYLNTQQSPVAATLYVRNRVREAIRVSKIPDAKSPLPVFAYTRIVFTDQVLKFLSQDELVYTFGETVALGASGIVIWG**SWENT**R**TKE**SC**QAIKE**YM**D**T**T**LNPYIINVTLAAKMCSQVLCQEQGVCIRKNWNSSDYLHLNPDNFAIQLEKGGKFTVRGKPTLEDLEQFSEKFYCSCYSTLSCKEKADVKDTDAVDVCIADGVCIDAFLK |
| HM35 | 33 | 14 amino acid residue substitutions of L342W, S343E, I344N, M345T, S347T, M348K, K349E, L352Q, L353A, L354I, D355K, N356E, E359D, and I361T, and truncations before residue F38 at the N-terminus and after residue P472 at the C-terminus. | FRAPPVIPNVPFLWAWNAPSEFCLGKFDEPLDMSLFSFIGSPRINATGQGVTIFYVDRLGYYPYIDSITGVTVNGGIPQKISLQDHLDKAKKDITFYMPVDNLGMAVIDWEEWRPTWARNWKPKDVYKNRSIELVQQQNVQLSLTEATEKAKQEFEKAGKDFLVETIKLGKLLRPNHLWGYYLFPDCYNHHYKKPGYNGSCFNVEIKRNDDLSWLWNESTALYPSIYLNTQQSPVAATLYVRNRVREAIRVSKIPDAKSPLPVFAYTRIVFTDQVLKFLSQDELVYTFGETVALGASGIVIWGT**WENT**R**TKE**SC**QAIKE**YM**D**T**T**LNPYIINVTLAAKMCSQVLCQEQGVCIRKNWNSSDYLHLNPDNFAIQLEKGGKFTVRGKPTLEDLEQFSEKFYCSCYSTLSCKEKADVKDTDAVDVCIADGVCIDAFLKPP |
| HM36 | 34 | 14 amino acid residue substitutions of L342W, S343E, | FRAPPVIPNVPFLWAWNAPSEFCLGKFDEPLDMSLFSFIGSPRINATGQGVTIFYVDRLGYYPYIDSITGVTVNGGIPQKISLQDHLDKAKKDITFYMPVDNLGMAVIDWEEWRPTWARNWKPKDVYKNRSIELVQQQNV |

TABLE 4-continued

Amino acid sequences of PH20 variants according to the present disclosure and the substitution/cleavage properties thereof

| Name | Sequence Number | Substitution | Sequence |
|---|---|---|---|
| | | I344N, M345T, S347T, M348K, K349E, L352Q, L353A, L354I, D355K, N356E, E359D, and I361T, and truncations before residue F38 at the N-terminus and after residue M473 at the C-terminus. | QLSLTEATEKAKQEFEKAGKDFLVETIKLGKLLRP<br>NHLWGYYLFPDCYNHHYKKPGYNGSCFNVEIKRND<br>DLSWLWNESTALYPSIYLNTQQSPVAATLYVRNRV<br>REAIRVSKIPDAKSPLPVFAYTRIVFTDQVLKFLS<br>QDELVYTFGETVALGASGIVIWGTWENTRTKESCQ<br>AIKEYMDTTLNPYIINVTLAAKMCSQVLCQEQGVC<br>IRKNWNSSDYLHLNPDNFAIQLEKGGKFTVRGKPT<br>LEDLEQFSEKFYCSCYSTLSCKEKADVKDTDAVDV<br>CIADGVCIDAFLKPPM |
| HM37 | 35 | 14 amino acid residue substitutions of L342W, S343E, I344N, M345T, S347T, M348K, K349E, L352Q, L353A, L354I, D355K, N356E, E359D, and I361T, and truncations before residue F38 at the N-terminus and after residue E474 at the C-terminus. | FRAPPVIPNVPFLWAWNAPSEFCLGKFDEPLDMSL<br>FSFIGSPRINATGQGVTIFYVDRLGYYPYIDSITG<br>VTVNGGIPQKISLQDHLDKAKKDITFYMPVDNLGM<br>AVIDWEEWRPTWARNWKPKDVYKNRSIELVQQQNV<br>QLSLTEATEKAKQEFEKAGKDFLVETIKLGKLLRP<br>NHLWGYYLFPDCYNHHYKKPGYNGSCFNVEIKRND<br>DLSWLWNESTALYPSIYLNTQQSPVAATLYVRNRV<br>REAIRVSKIPDAKSPLPVFAYTRIVFTDQVLKFLS<br>QDELVYTFGETVALGASGIVIWGTWENTRTKESCQ<br>AIKEYMDTTLNPYIINVTLAAKMCSQVLCQEQGVC<br>IRKNWNSSDYLHLNPDNFAIQLEKGGKFTVRGKPT<br>LEDLEQFSEKFYCSCYSTLSCKEKADVKDTDAVDV<br>CIADGVCIDAFLKPPME |
| HM38 | 36 | 14 amino acid residue substitutions of L342W, S343E, I344N, M345T, S347T, M348K, K349E, L352Q, L353A, L354I, D355K, N356E, E359D, and I361T, and truncations before residue F38 at the N-terminus and after residue T475 at the C-terminus. | FRAPPVIPNVPFLWAWNAPSEFCLGKFDEPLDMSL<br>FSFIGSPRINATGQGVTIFYVDRLGYYPYIDSITG<br>VTVNGGIPQKISLQDHLDKAKKDITFYMPVDNLGM<br>AVIDWEEWRPTWARNWKPKDVYKNRSIELVQQQNV<br>QLSLTEATEKAKQEFEKAGKDFLVETIKLGKLLRP<br>NHLWGYYLFPDCYNHHYKKPGYNGSCFNVEIKRND<br>DLSWLWNESTALYPSIYLNTQQSPVAATLYVRNRV<br>REAIRVSKIPDAKSPLPVFAYTRIVFTDQVLKFLS<br>QDELVYTFGETVALGASGIVIWGTWENTRTKESCQ<br>AIKEYMDTTLNPYIINVTLAAKMCSQVLCQEQGVC<br>IRKNWNSSDYLHLNPDNFAIQLEKGGKFTVRGKPT<br>LEDLEQFSEKFYCSCYSTLSCKEKADVKDTDAVDV<br>CIADGVCIDAFLKPPMET |
| HM39 | 37 | 14 amino acid residue substitutions of L342W, S343E, I344N, M345T, S347T, M348K, K349E, L352Q, L353A, L354I, D355K, N356E, E359D, and I361T, and truncations before residue F38 at the N-terminus and after residue E476 at the C-terminus. | FRAPPVIPNVPFLWAWNAPSEFCLGKFDEPLDMSL<br>FSFIGSPRINATGQGVTIFYVDRLGYYPYIDSITG<br>VTVNGGIPQKISLQDHLDKAKKDITFYMPVDNLGM<br>AVIDWEEWRPTWARNWKPKDVYKNRSIELVQQQNV<br>QLSLTEATEKAKQEFEKAGKDFLVETIKLGKLLRP<br>NHLWGYYLFPDCYNHHYKKPGYNGSCFNVEIKRND<br>DLSWLWNESTALYPSIYLNTQQSPVAATLYVRNRV<br>REAIRVSKIPDAKSPLPVFAYTRIVFTDQVLKFLS<br>QDELVYTFGETVALGASGIVIWGTWENTRTKESCQ<br>AIKEYMDTTLNPYIINVTLAAKMCSQVLCQEQGVC<br>IRKNWNSSDYLHLNPDNFAIQLEKGGKFTVRGKPT<br>LEDLEQFSEKFYCSCYSTLSCKEKADVKDTDAVDV<br>CIADGVCIDAFLKPPMETE |
| HM40 | 38 | 11 amino acid residue substitutions of M345T, S347T, M348K, K349E, L352Q, L353A, L354I, D355K, N356E, E359D, and I361T, and | NFRAPPVIPNVPFLWAWNAPSEFCLGKFDEPLDMS<br>LFSFIGSPRINATGQGVTIFYVDRLGYYPYIDSIT<br>GVTVNGGIPQKISLQDHLDKAKKDITFYMPVDNLG<br>MAVIDWEEWRPTWARNWKPKDVYKNRSIELVQQQN<br>VQLSLTEATEKAKQEFEKAGKDFLVETIKLGKLLR<br>PNHLWGYYLFPDCYNHHYKKPGYNGSCFNVEIKRN<br>DDLSWLWNESTALYPSIYLNTQQSPVAATLYVRNR<br>VREAIRVSKIPDAKSPLPVFAYTRIVFTDQVLKFL<br>SQDELVYTFGETVALGASGIVIWGTLSITRTKESC |

TABLE 4-continued

Amino acid sequences of PH20 variants according to the present disclosure and the substitution/cleavage properties thereof

| Name | Sequence Number | Substitution | Sequence |
|---|---|---|---|
| | | truncation before residue N37 at the N-terminus. | **QAIKE**YM**D**T**T**LNPYIINVTLAAKMCSQVLCQEQGV<br>CIRKNWNSSDYLHLNPDNFAIQLEKGGKFTVRGKP<br>TLEDLEQFSEKEYCSCYSTLSCKEKADVKDTDAVD<br>VCIADGVCIDAFLKPPMETEEPQIFYNASPSTLS |
| HM41 | 39 | 11 amino acid residue substitutions of M345T, S347T, M348K, K349E, L352Q, L353A, L354I, D355K, N356E, E359D, and I361T, and truncation before residue R39 at the N-terminus. | RAPPVIPNVPFLWAWNAPSEFCLGKFDEPLDMSLF<br>SFIGSPRINATGQGVTIFYVDRLGYYPYIDSITGV<br>TVNGGIPQKISLQDHLDKAKKDITFYMPVDNLGMA<br>VIDWEEWRPTWARNWKPKDVYKNRSIELVQQQNVQ<br>LSLTEATEKAKQEFEKAGKDFLVETIKLGKLLRPN<br>HLWGYYLFPDCYNHHYKKPGYNGSCFNVEIKRNDD<br>LSWLWNESTALYPSIYLNTQQSPVAATLYVRNRVR<br>EAIRVSKIPDAKSPLPVFAYTRIVFTDQVLKFLSQ<br>DELVYTFGETVALGASGIVIWGTLSI**TR**T**KE**SC**QA**<br>**IKE**YM**D**T**T**LNPYIINVTLAAKMCSQVLCQEQGVCI<br>RKNWNSSDYLHLNPDNFAIQLEKGGKFTVRGKPTL<br>EDLEQFSEKEYCSCYSTLSCKEKADVKDTDAVDVC<br>IADGVCIDAFLKPPMETEEPQIFYNASPSTLS |
| HM42 | 40 | 11 amino acid residue substitutions of M345T, S347T, M348K, K349E, L352Q, L353A, L354I, D355K, N356E, E359D, and I361T, and truncation before residue P41 at the N-terminus. | PPVIPNVPFLWAWNAPSEFCLGKFDEPLDMSLFSF<br>IGSPRINATGQGVTIFYVDRLGYYPYIDSITGVTV<br>NGGIPQKISLQDHLDKAKKDITFYMPVDNLGMAVI<br>DWEEWRPTWARNWKPKDVYKNRSIELVQQQNVQLS<br>LTEATEKAKQEFEKAGKDFLVETIKLGKLLRPNHL<br>WGYYLFPDCYNHHYKKPGYNGSCFNVEIKRNDDLS<br>WLWNESTALYPSIYLNTQQSPVAATLYVRNRVREA<br>IRVSKIPDAKSPLPVFAYTRIVFTDQVLKFLSQDE<br>LVYTFGETVALGASGIVIWGTLSI**TR**T**KE**SC**QAIK**<br>**E**YM**D**T**T**LNPYIINVTLAAKMCSQVLCQEQGVCIRK<br>NWNSSDYLHLNPDNFAIQLEKGGKFTVRGKPTLED<br>LEQFSEKFYCSCYSTLSCKEKADVKDTDAVDVCIA<br>DGVCIDAFLKPPMETEEPQIFYNASPSTLS |
| HM43 | 41 | 14 amino acid residue substitutions of L342W, S343E, I344N, M345T, S347T, M348K, K349E, L352Q, L353A, L354I, D355K, N356E, E359D, and I361T, and truncations before residue F38 at the N-terminus and after residue I465 at the C-terminus. | FRAPPVIPNVPFLWAWNAPSEFCLGKFDEPLDMSL<br>FSFIGSPRINATGQGVTIFYVDRLGYYPYIDSITG<br>VTVNGGIPQKISLQDHLDKAKKDITFYMPVDNLGM<br>AVIDWEEWRPTWARNWKPKDVYKNRSIELVQQQNV<br>QLSLTEATEKAKQEFEKAGKDFLVETIKLGKLLRP<br>NHLWGYYLFPDCYNHHYKKPGYNGSCFNVEIKRND<br>DLSWLWNESTALYPSIYLNTQQSPVAATLYVRNRV<br>REAIRVSKIPDAKSPLPVFAYTRIVFTDQVLKFLS<br>QDELVYTFGETVALGASGIVIWGS**WENT**R**TKE**SC**Q**<br>**AIKE**YM**D**T**T**LNPYIINVTLAAKMCSQVLCQEQGVC<br>IRKNWNSSDYLHLNPDNFAIQLEKGGKFTVRGKPT<br>LEDLEQFSEKFYCSCYSTLSCKEKADVKDTDAVDV<br>CIADGVCI |
| HM44 | 42 | 14 amino acid residue substitutions of L342W, S343E, I344N, M345T, S347T, M348K, K349E, L352Q, L353A, L354I, D355K, N356E, E359D, and I361T, and truncations before residue F38 at the N-terminus and after residue D466 at the C-terminus. | FRAPPVIPNVPFLWAWNAPSEFCLGKFDEPLDMSL<br>FSFIGSPRINATGQGVTIFYVDRLGYYPYIDSITG<br>VTVNGGIPQKISLQDHLDKAKKDITFYMPVDNLGM<br>AVIDWEEWRPTWARNWKPKDVYKNRSIELVQQQNV<br>QLSLTEATEKAKQEFEKAGKDFLVETIKLGKLLRP<br>NHLWGYYLFPDCYNHHYKKPGYNGSCFNVEIKRND<br>DLSWLWNESTALYPSIYLNTQQSPVAATLYVRNRV<br>REAIRVSKIPDAKSPLPVFAYTRIVFTDQVLKFLS<br>QDELVYTFGETVALGASGIVIWGS**WENT**R**TKE**SC**Q**<br>**AIKE**YM**D**T**T**LNPYIINVTLAAKMCSQVLCQEQGVC<br>IRKNWNSSDYLHLNPDNFAIQLEKGGKFTVRGKPT<br>LEDLEQFSEKFYCSCYSTLSCKEKADVKDTDAVDV<br>CIADGVCID |
| HM45 | 43 | 14 amino acid residue substitutions of L342W, S343E, I344N, M345T, S347T, M348K, | FRAPPVIPNVPFLWAWNAPSEFCLGKFDEPLDMSL<br>FSFIGSPRINATGQGVTIFYVDRLGYYPYIDSITG<br>VTVNGGIPQKISLQDHLDKAKKDITFYMPVDNLGM<br>AVIDWEEWRPTWARNWKPKDVYKNRSIELVQQQNV<br>QLSLTEATEKAKQEFEKAGKDFLVETIKLGKLLRP<br>NHLWGYYLFPDCYNHHYKKPGYNGSCFNVEIKRND |

TABLE 4-continued

Amino acid sequences of PH20 variants according to the present disclosure and the substitution/cleavage properties thereof

| Name | Sequence Number | Substitution | Sequence |
|---|---|---|---|
| | | K349E, L352Q, L353A, L354I, D355K, N356E, E359D, and I361T, and truncations before residue F38 at the N-terminus and after residue A467 at the C-terminus. | DLSWLWNESTALYPSIYLNTQQSPVAATLYVRNRV<br>REAIRVSKIPDAKSPLPVFAYTRIVFTDQVLKFLS<br>QDELVYTFGETVALGASGIVIWGSWENTRTKESCQ<br>AIKEYMDTTLNPYIINVTLAAKMCSQVLCQEQGVC<br>IRKNWNSSDYLHLNPDNFAIQLEKGGKFTVRGKPT<br>LEDLEQFSEKFYCSCYSTLSCKEKADVKDTDAVDV<br>CIADGVCIDA |
| HP46 | 44 | 15 amino acid residue substitutions of T341S, L342W, S343E, I344N, M345T, S347T, M348K, K349E, L352Q, L353A, L354I, D355K, N356E, E359D, and I361T, and truncations before residue F38 at the N-terminus and after residue F468 at the C-terminus. | FRAPPVIPNVPFLWAWNAPSEFCLGKFDEPLDMSL<br>FSFIGSPRINATGQGVTIFYVDRLGYYPYIDSITG<br>VTVNGGIPQKISLQDHLDKAKKDITFYMPVDNLGM<br>AVIDWEEWRPTWARNWKPKDVYKNRSIELVQQQNV<br>QLSLTEATEKAKQEFEKAGKDFLVETIKLGKLLRP<br>NHLWGYYLFPDCYNHHYKKPGYNGSCFNVEIKRND<br>DLSWLWNESTALYPSIYLNTQQSPVAATLYVRNRV<br>REAIRVSKIPDAKSPLPVFAYTRIVFTDQVLKFLS<br>QDELVYTFGETVALGASGIVIWGSWENTRTKESCQ<br>AIKEYMDTTLNPYIINVTLAAKMCSQVLCQEQGVC<br>IRKNWNSSDYLHLNPDNFAIQLEKGGKFTVRGKPT<br>LEDLEQFSEKFYCSCYSTLSCKEKADVKDTDAVDV<br>CIADGVCIDAF |
| HM47 | 45 | 14 amino acid residue substitutions of L342W, S343E, I344N, M345T, S347T, M348K, K349E, L352Q, L353A, L354I, D355K, N356E, E359D, and I361T, and truncations before residue F38 at the N-terminus and after residue P478 at the C-terminus. | FRAPPVIPNVPFLWAWNAPSEFCLGKFDEPLDMSL<br>FSFIGSPRINATGQGVTIFYVDRLGYYPYIDSITG<br>VTVNGGIPQKISLQDHLDKAKKDITFYMPVDNLGM<br>AVIDWEEWRPTWARNWKPKDVYKNRSIELVQQQNV<br>QLSLTEATEKAKQEFEKAGKDFLVETIKLGKLLRP<br>NHLWGYYLFPDCYNHHYKKPGYNGSCFNVEIKRND<br>DLSWLWNESTALYPSIYLNTQQSPVAATLYVRNRV<br>REAIRVSKIPDAKSPLPVFAYTRIVFTDQVLKFLS<br>QDELVYTFGETVALGASGIVIWGTWENTRTKESCQ<br>AIKEYMDTTLNPYIINVTLAAKMCSQVLCQEQGVC<br>IRKNWNSSDYLHLNPDNFAIQLEKGGKFTVRGKPT<br>LEDLEQFSEKFYCSCYSTLSCKEKADVKDTDAVDV<br>CIADGVCIDAFLKPPMETEEP |
| HM48 | 46 | 14 amino acid residue substitutions of L342W, S343E, I344N, M345T, S347T, M348K, K349E, L352Q, L353A, L354I, D355K, N356E, E359D, and I361T, and truncations before residue F38 at the N-terminal and after residue 1480 at the C-terminus. | FRAPPVIPNVPFLWAWNAPSEFCLGKFDEPLDMSL<br>FSFIGSPRINATGQGVTIFYVDRLGYYPYIDSITG<br>VTVNGGIPQKISLQDHLDKAKKDITFYMPVDNLGM<br>AVIDWEEWRPTWARNWKPKDVYKNRSIELVQQQNV<br>QLSLTEATEKAKQEFEKAGKDFLVETIKLGKLLRP<br>NHLWGYYLFPDCYNHHYKKPGYNGSCFNVEIKRND<br>DLSWLWNESTALYPSIYLNTQQSPVAATLYVRNRV<br>REAIRVSKIPDAKSPLPVFAYTRIVFTDQVLKFLS<br>QDELVYTFGETVALGASGIVIWGTWENTRTKESCQ<br>AIKEYMDTTLNPYIINVTLAAKMCSQVLCQEQGVC<br>IRKNWNSSDYLHLNPDNFAIQLEKGGKFTVRGKPT<br>LEDLEQFSEKFYCSCYSTLSCKEKADVKDTDAVDV<br>CIADGVCIDAFLKPPMETEEPQI |
| HM49 | 47 | 14 amino acid residue substitutions of L342W, S343E, I344N, M345T, S347T, M348K, K349E, L352Q, L353A, L354I, D355K, N356E, E359D, and I361T, and | FRAPPVIPNVPFLWAWNAPSEFCLGKFDEPLDMSL<br>FSFIGSPRINATGQGVTIFYVDRLGYYPYIDSITG<br>VTVNGGIPQKISLQDHLDKAKKDITFYMPVDNLGM<br>AVIDWEEWRPTWARNWKPKDVYKNRSIELVQQQNV<br>QLSLTEATEKAKQEFEKAGKDFLVETIKLGKLLRP<br>NHLWGYYLFPDCYNHHYKKPGYNGSCFNVEIKRND<br>DLSWLWNESTALYPSIYLNTQQSPVAATLYVRNRV<br>REAIRVSKIPDAKSPLPVFAYTRIVFTDQVLKFLS<br>QDELVYTFGETVALGASGIVIWGTWENTRTKESCQ<br>AIKEYMDTTLNPYIINVTLAAKMCSQVLCQEQGVC<br>IRKNWNSSDYLHLNPDNFAIQLEKGGKFTVRGKPT |

TABLE 4-continued

Amino acid sequences of PH20 variants according to the present disclosure and the substitution/cleavage properties thereof

| Name | Sequence Number | Substitution | Sequence |
|---|---|---|---|
| | | truncations before residue F38 at the N-terminus and after residue Y482 at the C-terminus. | LEDLEQFSEKFYCSCYSTLSCKEKADVKDTDAVDV CIADGVCIDAFLKPPMETEEPQIFY |
| HM50 | 48 | 14 amino acid residue substitutions of L342W, S343E, I344N, M345T, S347T, M348K, K349E, L352Q, L353A, L354I, D355K, N356E, E359D, and I361T, and truncations before residue F38 at the N-terminus and after residue A484 at the C-terminus. | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTFGETVALGASGIVIWGTWENTRTKESCQ AIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCIDAFLKPPMETEEPQIFYNA |
| HM51 | 49 | 14 amino acid residue substitutions of L342W, S343E, I344N, M345T, S347T, M348K, K349E, L352Q, L353A, L354I, D355K, N356E, E359D, and I361T, and truncations before residue F38 at the N-terminus and after residue P486 at the C-terminus. | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTFGETVALGASGIVIWGTWENTRTKESCQ AIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCIDAFLKPPMETEEPQIFYNASP |
| HM52 | 50 | 14 amino acid residue substitutions of L342W, S343E, I344N, M345T, S347T, M348K, K349E, L352Q, L353A, L354I, D355K, N356E, E359D, and I361T, and truncations before residue F38 at the N-terminus and after residue T488 at the C-terminus. | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTFGETVALGASGIVIWGTWENTRTKESCQ AIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCIDAFLKPPMETEEPQIFYNASPST |

Meanwhile, previous studies reported that the enzymatic activity of wild-type human PH20 changes depending on the truncation positions of amino acid residues located at the C-terminus. In the present invention, however, a specific alpha helix forming the secondary structure of human PH20 was substituted with the alpha helix of other human hyaluronidase, thereby constructing human PH20 variants having higher stability than wild-type human PH20, and in these variants, the interaction between the substituted alpha-helix domain and other secondary structures of PH20 shows a pattern different from that of wild-type PH20, so that the variants are characterized by having a certain level of enzymatic activity or higher, regardless of the truncation position at the C-terminus.

In addition, in the present invention, attempts were made to increase the expression of a recombinant PH20 protein by using the signal peptide of other proteins exhibiting high protein expression levels in animal cells, instead of the original signal peptide of human PH20.

Therefore, in another aspect, the PH20 variant included in the pharmaceutical composition according to the present invention is characterized by including, at the N-terminus thereof, a signal peptide derived from human hyaluronidase-1 (Hyal1), a human growth hormone, or human serum albumin, instead of a signal peptide of wild-type PH20 of M1 to T35, and preferably including, as shown in Table 5, a human-growth-hormone-derived signal peptide having the amino acid sequence of MATGSRTSLL-LAFGLLCLPWLQEGSA according to SEQ ID NO: 2, a human serum albumin-derived signal peptide having the amino acid sequence of MKWVTFISLLFLESSAYS according to SEQ ID NO: 3, or a human-Hyal1-derived signal peptide having the amino acid sequence of MAAHL-LPICALFLTLLDMAQG according to SEQ ID NO: 4, but is not limited thereto.

TABLE 5

Amino acid sequence of signal peptide of human growth hormone, human serum albumin, or human Hyal1

| Origin of signal peptide | Amino acid sequence | SEQ ID NO: |
|---|---|---|
| Human growth hormone | MATGSRTSLLLAFGLLCLPWLQEGSA | 2 |
| Human serum albumin | MKWVTFISLLFLFSSAYS | 3 |
| Human Hyal1 | MAAHLLPICALFLTLLDMAQG | 4 |

Among the PH20 variants included in the pharmaceutical composition according to the present invention, a variant having a 6xHis-tag attached to the C-terminus was named HM, and a variant without the 6xHis-tag was named HP. In addition, mature wild-type PH20 (L36 to S490) with a 6xHis-tag attached to the C-terminus thereof was named WT, and mature wild-type PH20 (L36 to Y482) without the 6xHis-tag and in which the C-terminus is truncated after Y482 was named HW2.

HP46 (SEQ ID NO: 44) is a human PH20 variant obtained by modeling a protein structure using Hyal1 (PDB ID: 2PE4) (Chao et al., 2007), which is human hyaluronidase, with a known protein tertiary structure, and then substituting the amino acid sequence of amino acids of alpha-helix 8 and the linker region between alpha-helix 7 and alpha-helix 8 of human PH20 with the amino acid sequence of Hyal1, and subjecting the N-terminus to truncation at F38 and subjecting the C-terminus to truncation after F468. In particular, alpha-helix 8 is located outside the protein tertiary structure of PH20 and has less interaction with neighboring alpha helices or beta-strands than other alpha helices. In general, enzymatic activity and thermal stability have a trade-off relationship therebetween, and thus the higher the thermal stability of a protein, the lower the enzymatic activity, whereas, when enzymatic activity increases due to an improvement in the flexibility of the protein structure, the thermal stability tends to be reduced. However, the specific activity of HP46, measured by Turbidimetric assay under conditions at pH 7.0, was about 46 units/μg, which was evaluated to be about two times that of wild-type PH20, which was about 23 units/μg.

The thermal stability of a protein may be evaluated based on a melting temperature (Tm), at which 50% of the protein tertiary structure is denatured, and on an aggregation temperature (Tagg), at which aggregation between proteins occurs. In general, the aggregation temperature of a protein tends to be lower than the melting temperature thereof. The alpha-helix 8 of Hyal1 exhibits greater hydrophilicity than the alpha-helix 8 of PH20. The substituted alpha-helix 8 of Hyal1 increases the protein surface hydrophilicity of HP46, thereby causing the effect of delaying aggregation between proteins that occurs due to hydrophobic interactions, and thus the aggregation temperature is 51° C., which is observed to be an increase of 4.5° C. compared to the aggregation temperature of wild-type PH20, which is 46.5° C.

HP46 is a variant in which amino acids in the alpha-helix 8 and the linker region between alpha-helix 7 and alpha-helix 8 of PH20 are substituted, wherein T341 is substituted with serine. When amino acid residue 341 is threonine, the enzyme activity is similar to that of wild-type PH20, but upon substitution with serine, the enzyme activity increases about 2-fold, and it was found that, even in a substrate gel assay, the resultant variant hydrolyzed hyaluronic acid 5 to 6 times more than wild-type PH20. Substrate gel assay involves protein denaturation and refolding processes, which means that the protein tertiary structure refolding and restoration force of HP46 are enhanced compared to wild-type PH20.

The amount of the PH20 variant in the pharmaceutical composition according to the present invention is at least 50 units/mL, preferably in the range of 100 to 20,000 units/mL, more preferably in the range of about 150 to about 18,000 units/mL, still more preferably in the range of 1,000 to 16,000 units/mL, and most preferably in the range of 1,500 to 12,000 units/mL.

Illustrative examples of the drug included in the pharmaceutical composition according to the present invention include, but are not limited to, protein drugs, antibody drugs, small molecules, aptamers, RNAi, antisenses, and cellular therapeutic agents such as chimeric antigen receptor (CAR)-T or CAR-natural killer (NK), and it is possible to use not only currently commercially available drugs but also drugs in clinical trials or under development.

As the drug, a protein drug or an antibody drug may preferably be used.

The "protein drug" included in the pharmaceutical composition according to the present invention is a drug that consists of amino acids, and thus exhibits the effect of treating or preventing a disease through the activity of a protein, is a drug consisting of a protein other than the antibody drug, and may be selected from the group consisting of a cytokine, a therapeutic enzyme, a hormone, a soluble receptor and a fusion protein thereof, insulin or an analogue thereof, bone morphogenetic protein (BMP), erythropoietin (EPO), and a serum-derived protein, but is not limited thereto.

The cytokine included in the pharmaceutical composition according to the present invention may be selected from the group consisting of interferon, interleukin, colony-stimulating factor (CSF), tumor necrosis factor (TNF), and tissue growth factor (TGF), but is not limited thereto.

The illustrative examples of the therapeutic enzyme may include, but are not limited to, β-glucocerebrosidase and agalsidase β.

The soluble receptor included in the pharmaceutical composition according to the present invention means an extracellular domain of the receptor, and the fusion protein thereof means a protein in which the Fc region or the like of an antibody is fused to the soluble receptor. The soluble receptor is a soluble form of a receptor to which a disease-related ligand binds, and illustrative examples thereof include a form in which an Fc region is fused to the TNF-α soluble receptor (e.g., a product containing the ingredient etanercept and forms similar thereto), a form in which an Fc region is fused to the VEGF soluble receptor (a product containing the ingredient aflibercept and forms similar thereto), a form in which an Fc region is fused to CTLA-4 (e.g., a product containing the ingredient abatacept or belatacept and forms similar thereto), a form in which an Fc region is fused to the interleukin 1 soluble receptor (e.g., a product containing the ingredient rilonacept and forms similar thereto), and a form in which an Fc region is fused to the LFA3 soluble receptor (e.g., a product containing the ingredient alefacept and forms similar thereto), but are not limited thereto.

The hormone included in the pharmaceutical composition according to the present invention refers to a hormone injected into the body or an analog thereof for the treatment or prevention of diseases caused by hormone deficiency and the like, and illustrative examples thereof include, but are not limited to, human growth hormone, estrogen, progesterone, etc.

The serum-derived protein included in the pharmaceutical composition according to the present invention is a protein present in plasma, and means both proteins extracted from plasma and produced recombinant proteins, and illustrative examples thereof may include are not limited to, fibrinogen, von Willebrand factor, albumin, thrombin, factor II (FII), factor V (FV), factor VII (FVII), factor VIII (FVIII), factor IX (FIX), factor X (FX), and factor XI (FXI).

The antibody drug included in the pharmaceutical composition according to the present invention may be a monoclonal antibody drug or a polyclonal antibody drug.

The monoclonal antibody drug according to the present invention means a protein containing a monoclonal antibody and a monoclonal antibody fragment that are capable of specifically binding to an antigen related to a specific disease. The monoclonal antibody also includes a bispecific antibody, and the protein containing a monoclonal antibody or fragment thereof conceptually includes an antibody-drug conjugate (ADC).

Examples of the antigen related to a specific disease include 4-1BB, integrin, amyloid beta, angiopoietin (angiopoietin 1 or 2), angiopoietin analog 3, B-cell-activating factor (BAFF), B7-H3, complement 5, CCR4, CD3, CD4, CD6, CD11a, CD19, CD20, CD22, CD30, CD33, CD38, CD52, CD62, CD79b, CD80, CGRP, Claudin-18, complement factor D, CTLA4, DLL3, EGF receptor, hemophilia factor, Fc receptor, FGF23, folate receptor, GD2, GM-CSF, HER2, HER3, interferon receptor, interferon gamma, IgE, IGF-1 receptor, interleukin 1, interleukin 2 receptor, interleukin 4 receptor, interleukin 5, interleukin 5 receptor, interleukin 6, interleukin 6 receptor, interleukin 7, interleukin 12/23, interleukin 13, interleukin 17A, interleukin 17 receptor A, interleukin 31 receptor, interleukin 36 receptor, LAG3, LFA3, NGF, PVSK9, PD-1, PD-L1, RANK-L, SLAMF7, tissue factor, TNF, VEGF, VEGF receptor, and von Willebrand factor (vWF), but are not limited thereto.

The following are examples of proteins, including but not limited to monoclonal antibodies or monoclonal antibody fragments, that target antigens related to a specific disease:

utomilumab as an anti 4-1BB antibody;
natalizumab, etrolizumab, vedolizumab, and bimagrumab as antibodies against integrin;
bapineuzumab, crenezumab, solanezumab, aducanumab, and gantenerumab as antibodies against amyloid beta;
AMG780 against angiopoietin 1 and 2, MEDI 3617 and nesvacumab against angiopoietin 2, and vanucizumab which is a bispecific antibody against angiopoietin 2 and VEGF, as antibodies against angiopoietin;
evinacumab as an antibody against angiopoietin analog 3;
tabalumab, lanalumab, and belimumab as antibodies against B-cell-activating factor (BAFF);
omburtamab as an antibody against B7-H3;
ravulizumab and eculizumab as antibodies against complement 5;
mogamulizumab as an antibody against CCR4;
otelixizumab, teplizumab, and muromonab as antibodies against CD3, tebentafusp as a bispecific antibody against GP100 and CD3, blinatumomab as a bispecific antibody against CD19 and CD3, and REGN1979 as a bispecific antibody against CD20 and CD3;
ibalizumab and zanolimumab as antibodies against CD4;
itolizumab as an antibody against CD6;
efalizumab as an antibody against CD11a;
inebilizumab, tafasitamab, and loncastuximab tesirine which is an ADC, as antibodies against CD19;
ocrelizumab, ublituximab, obinutuzumab, ofatumumab, rituximab, tositumomab, and ibritumomab tiuxetan which is an ADC, as antibodies against CD20;
epratuzumab, inotuzumab ozogamicin which is an ADC, and moxetumomab pasudotox as antibodies against CD22;
brentuximab vedotin as an ADC against CD30;
vadastuximab talirine and gemtuzumab ozogamicin as ADCs against CD33;
daratumumab and isatuximab as antibodies against CD38;
alemtuzumab as an antibody against CD52;
crizanlizumab as an antibody against CD62;
polaruzumab vedotin as an ADC against CD79b;
galiximab as an antibody against CD80;
eptinezumab, fremanezumab, galcanezumab, and erenumab as antibodies against CGRP;
zolbetuximab as an antibody against Claudin-18;
lampalizumab as an antibody against complement factor D;
tremelimumab, zalifrelimab, and ipilimumab as antibodies against CTLA4;
rovalpituzumab tesirine as an ADC against DLL3;
cetuximab, depatuxizumab, zalutumumab, necitumumab, and panitumumab as antibodies against the EGF receptor;
emicizumab as a bispecific antibody against coagulation factor IX and factor X, which are hemophilia factors;
nipocalimab and rozanolixizumab as antibodies against the Fc receptor;
burosumab as an antibody against FGF23;
farletuzumab as an antibody against the folate receptor and mirvetuximab soravtansine as an ADC against the folate receptor;
dinutuximab and naxitamab as antibodies against GD2;
otilimab as an antibody against GM-CSF;
margetuximab, pertuzumab, and trastuzumab as antibodies against HER2, and trastuzumab deruxtecan, trastuzumab emtansine, and trastuzumab duocarmazine as ADCs against HER2;
patritumab as an antibody against HER3;
anifrolumab as an antibody against interferon receptor;
emapalumab as an antibody against interferon gamma;
ligelizumab and omalizumab as antibodies against IgE;
dalotuzumab, figitumumab, and teprotumumab as antibodies against the IGF-1 receptor;
gebokizumab and canakinumab as antibodies against interleukin 1;
daclizumab and basiliximab as antibodies against the interleukin 2 receptor;
dupilumab as an antibody against the interleukin 4 receptor;

mepolizumab and reslizumab as antibodies against interleukin 5;

benralizumab as an antibody against the interleukin 5 receptor;

clazakizumab, olokizumab, sirukumab, and siltuximab as antibodies against interleukin 6;

sarilumab, satralizumab, tocilizumab, and REGN88 as antibodies against the interleukin 6 receptor;

secukinumab as an antibody against interleukin 7;

ustekinumab and briakinumab as antibodies against interleukin 12/23;

lebrikizumab and tralokinumab as antibodies against interleukin 13;

ixekizumab and bimekizumab as antibodies against interleukin 17A;

brodalumab as an antibody against interleukin 17 receptor A;

brazikumab, guselkumab, risankizumab, tildrakizumab, and mirikizumab as antibodies against interleukin 23;

nemolizumab as an antibody against the interleukin 31 receptor;

spesolimab as an antibody against the interleukin 36 receptor;

relatlimab as an antibody against LAG3;

narsoplimab as an antibody against NASP2;

fasinumab and tanezumab as antibodies against NGF;

alirocumab, evolocumab, and bococizumab as antibodies against PVSK9;

lambrolizumab, balstilimab, camrelizumab, cemiplimab, dostarlimab, prolgolimab, sintilimab, spartalizumab, tislelizumab, pembrolizumab, and nivolumab as antibodies against PD-1;

atezolizumab, avelumab, envafolimab, and durvalumab as antibodies against PD-L1, and bintrafusp alpha as a bispecific antibody against TGF beta and PD-L1;

denosumab as an antibody against RANK-L;

elotuzumab as an antibody against SLAMF7;

concizumab and marstacimab as antibodies against tissue factor;

infliximab, adalimumab, and golimumab as antibodies against TNF, particularly TNFα, certolizumab pegol as an antibody fragment, and ozoralizumab as a bispecific antibody against TNF and albumin;

brolucizumab, ranibizumab, and bevacizumab as antibodies against VEGF, and faricimab as a bispecific antibody against VEGF and Ang2;

ramucirumab as an antibody against the VEGF receptor; and caplacizumab as an antibody against vWF.

Meanwhile, the overexpression of human epidermal growth factor receptor 2 (HER2), which promotes cell division, is observed in about 20 to 25% of breast cancer patients, and HER2-overexpressing breast cancer progresses quickly, is aggressive, and has a low response to chemotherapy compared to HER2-low-expressed breast cancer, and thus the prognosis thereof is not good. Trastuzumab, which is a monoclonal antibody drug targeting HER2, specifically binds to HER2 on the surfaces of HER2-overexpressing cancer cells to inhibit the signal transduction of cell replication and proliferation, thereby slowing tumor progression. Trastuzumab was approved by the United States Food and Drug Administration (FDA) in 1998 for the treatment of breast cancer in the United States, and in 2003 by the Korea Food and Drug Administration (KFDA) in South Korea. Since then, the efficacy of trastuzumab was also recognized in HER2-overexpressing gastric cancer, and thus has been used as a therapeutic agent for gastric cancer.

A Roche's Herceptin intravenous injection formulation (commercial name: Herceptin) comprises 440 mg of trastuzumab as a main ingredient, and lyophilized trastuzumab is mixed with physiological saline and injected into a vein. On the other hand, a subcutaneous injection formulation of trastuzumab (commercial name: Herceptin SC) is a 5 mL liquid formulation, and contains 600 mg (120 mg/mL) of trastuzumab as a main ingredient, and includes, as additives, 20 mM histidine (pH 5.5), 210 mM trehalose, 10 mM methionine, 0.04% polysorbate 20, and 10,000 units of rHuPH20 (2,000 Units/mL, 0.004%, 40 μg/mL).

The use-by period of Herceptin subcutaneous injection formulations is 21 months. The intravenous injection formulation of trastuzumab is in a lyophilized form and has a use-by period of 30 months, but the subcutaneous injection formulation of trastuzumab is in a liquid state and has a short use-by period of 21 months. For this reason, it can be presumed that the stability of one or more of trastuzumab and recombinant human hyaluronidase PH20 in liquid formulations is limited.

In this context, in the present invention, in view of the characteristics of the PH20 variant according to the present invention, in which, compared to wild-type human hyaluronidase PH20 and recombinant human PH20 available from Halozyme, the PH20 variant not only has increased enzymatic activity, but also has a high measured protein aggregation temperature, thus exhibiting enhanced thermal stability, the use-by period of the subcutaneous injection formulation is set to a long-term period, preferably 21 months or longer.

The content of the antibody drug in the pharmaceutical composition according to the present invention may be in the range of 5 to 500 mg/mL, preferably 20 to 200 mg/mL, more preferably 100 to 150 mg/mL, and most preferably 120±18 mg/mL, for example, about 110 mg/mL, about 120 mg/mL, or about 130 mg/mL.

The polyclonal antibody included in the pharmaceutical composition according to the present invention is preferably a serum antibody, etc., extracted from serum such as immune globulin, but is not limited thereto.

In the case of a small-molecule compound, any drug that requires a rapid effect for prevention or treatment may be used without limitation. For example, morphine-based painkillers may be used (Thomas et al., 2009). In addition, when used as a therapeutic agent for tissue necrosis caused by anticancer drugs, the small-molecule compound may be used alone or in combination with antidote drugs such as Vinca alkaloids and Taxanes (Kreidieh et al., 2016).

The pharmaceutical composition according to the present invention may further include one or more selected from the group consisting of a buffer, a stabilizer, and a surfactant.

The buffer included in the composition according to the present invention may be used without limitation, as long as it enables realization of a pH of 4 to 8, preferably 5 to 7, and the buffer is preferably one or more selected from the group consisting of malate, formate, citrate, acetate, propionate, pyridine, piperazine, cacodylate, succinate, 2-(N-morpholino) ethanesulfonic acid (MES), histidine, Tris, bis-Tris, phosphate, ethanolamine, carbonate, piperazine-N,N'-bis(2-ethanesulfonic acid) (PIPES), imidazole, BIS-TRIS propane, N, N-bis(2-hydroxyethyl)-2-aminoethanesulfonic acid (BES), 3-(N-morpholino) propanesulfonic acid) (MOPS), hydroxyethyl piperazine ethane sulfonic acid (HEPES), pyrophosphate, and triethanolamine, more preferably a histidine buffer, e.g., L-histidine/HCl, but is not limited thereto.

The concentration of the buffer may be in the range of 0.001 to 200 mM, preferably 1 to 50 mM, more preferably 5 to 40 mM, and most preferably 10 to 30 mM.

Stabilizers in the composition according to the present invention may be used without limitation, as long as they are commonly used in the art for the purpose of stabilizing proteins, and preferably, the stabilizers may be, for example, one or more selected from the group consisting of carbohydrates, sugars or hydrates thereof, sugar alcohols or hydrates thereof, and amino acids.

Carbohydrates, sugars, or sugar alcohols used as the stabilizer may be one or more selected from the group consisting of trehalose or hydrates thereof, sucrose, saccharin, glycerol, erythritol, threitol, xylitol, arabitol, ribitol, mannitol, sorbitol, galactitol, fucitol, iditol, inositol, volemitol, isomalt, maltitol, polyglycitol, cyclodextrin, hydroxylpropyl cyclodextrin (Hydroxypropyl Beta-cyclodextrin), and glucose;

and the amino acids may be one or more selected from the group consisting of glutamine, glutamic acid, glycine, lysine, lysilysine, leucine, methionine, valine, serine, selenomethionine, citrulline, arginine, asparagine, aspartic acid, ornithine, isoleucine, taurine, theanine, threonine, tryptophan, tyrosine, phenylalanine, proline, pyrrolysine, histidine, and alanine, but is not limited thereto.

The concentration of the sugars or sugar alcohols used as a stabilizer in the pharmaceutical composition according to the present invention may be in the range of 0.001 to 500 mM, preferably 100 to 300 mM, more preferably 150 to 250 mM, and most preferably 180 to 230 mM, and particularly, may be about 210 mM.

In addition, the concentration of amino acids used as a stabilizer in the pharmaceutical composition according to the present invention may be in the range of 1 to 100 mM, preferably 3 to 30 mM, more preferably 5 to 25 mM, and most preferably 7 to 20 mM, and specifically, may be in the range of about 8 to 15 mM.

The composition according to the invention may further include a surfactant.

Preferably, the surfactant may be a nonionic surfactant such as polyoxyethylene-sorbitan fatty acid ester (polysorbate or Tween), polyethylene-polypropylene glycol, polyoxyethylene-stearate, polyoxyethylene alkyl ethers, e.g., polyoxyethylene monolauryl ether, alkylphenyl polyoxyethylene ether [Triton-X], and a polyoxyethylene-polyoxypropylene copolymer [Poloxamer and Pluronic], and sodium dodecyl sulfate (SDS), but is not limited thereto.

More preferably, polysorbate may be used. The polysorbate may be polysorbate 20 or polysorbate 80, but is not limited thereto.

The concentration of the nonionic surfactant in the pharmaceutical composition according to the present invention may be in the range of 0.0000001% to 0.5% (w/v), preferably 0.000001% to 0.4% (w/v), more preferably 0.00001% to 0.3% (w/v), and most preferably 0.001% to 0.2% (w/v).

In one specific working example, the pharmaceutical composition according to the present invention may include 50 to 350 mg/mL of an antibody, for example, an anti-HER2 antibody or an immune checkpoint antibody, histidine buffer providing a pH of 5.5±2.0, 10 to 400 mM α,α-trehalose, 1 to 50 mM methionine, and 0.0000001% to 0.5% (w/v) of polysorbate.

In a more specific working example, the pharmaceutical composition according to the present invention may include 120 mg/mL of an anti-HER2 antibody or an immune checkpoint antibody, 20 mM histidine buffer that provides a pH of 5.5±2.0, 210 mM α, α-trehalose, 10 mM methionine, and 2,000 units/mL of a PH20 variant, and may further include 0.005% to 0.1% (w/v) polysorbate.

The pharmaceutical composition according to the present invention may be administered via intravenous injection, subcutaneous injection, intramuscular injection, intraperitoneal injection, endothelial administration, topical administration, intranasal administration, intrapulmonary administration, intrarectal administration, and the like, and subcutaneous administration is preferably performed via subcutaneous injection, and it is more preferable to use the pharmaceutical composition as an injection formulation for subcutaneous injection administration.

Therefore, another embodiment of the present invention provides a formulation including the pharmaceutical composition according to the present invention, preferably an injection formulation for subcutaneous administration.

The injection formulation for subcutaneous administration may be provided in a ready-to-inject form without an additional dilution process, and may be provided after being contained in a pre-filled syringe, a glass ampoule, or a plastic container.

The present invention also relates to a method of treating a disease using the pharmaceutical composition or formulation according to the present invention.

The disease that can be treated using the pharmaceutical composition or formulation according to the present invention is not particularly limited, and there is no limitation thereto, as long as it is a disease that can be treated with a drug used in combination with the PH20 variant according to the present invention.

The disease that can be treated using the pharmaceutical composition or formulation according to the present invention may be cancer or an autoimmune disease, but is not limited thereto.

The cancer or carcinoma treatable with the pharmaceutical composition or formulation according to the present invention is not particularly limited, and includes both solid cancers and blood cancers. Examples of such cancers may be selected from the group consisting of skin cancer such as melanoma, liver cancer, hepatocellular carcinoma, gastric cancer, breast cancer, lung cancer, ovarian cancer, bronchial cancer, nasopharyngeal cancer, laryngeal cancer, pancreatic cancer, bladder cancer, colorectal cancer, colon cancer, cervical cancer, brain cancer, prostate cancer, bone cancer, thyroid cancer, parathyroid cancer, kidney cancer, esophageal cancer, biliary tract cancer, testicular cancer, rectal cancer, head and neck cancer, spinal cancer, ureteral cancer, osteosarcoma, neuroblastoma, fibrosarcoma, rhabdomyosarcoma, astrocytoma, neuroblastoma, and glioma, but are not limited thereto. Preferably, the cancer that can be treated using the pharmaceutical composition or formulation of the present invention may be selected from the group consisting of gastric cancer, colorectal cancer, breast cancer, lung cancer, and kidney cancer, but is not limited thereto.

Autoimmune diseases treatable with the pharmaceutical composition or formulation according to the present invention may be selected from the group consisting of rheumatoid arthritis, asthma, psoriasis, multiple sclerosis, allergic rhinitis, Crohn's disease, ulcerative colitis, systemic erythematous lupus, type I diabetes, inflammatory bowel disease (IBD), and atopic dermatitis, but are not limited thereto.

The present invention also provides a method of treating a disease characterized by administering the pharmaceutical composition or formulation according to the present invention to a subject in need of treatment, and the present invention further provides the use of the pharmaceutical composition or formulation according to the present invention for preparing a medicament for the treatment of a disease.

Unless otherwise defined herein, the technical terms and scientific terms used in the present invention have meanings generally understood by those of ordinary skill in the art. In addition, repeated descriptions of the same technical configuration and operation as those of the related art will be omitted.

Hereinafter, the present invention will be described in further detail with reference to the working examples. These working examples are provided for illustrative purposes only, and it will be obvious to those of ordinary skill in the art that these working examples should not be construed as limiting the scope of the present invention.

WORKING EXAMPLES

Working Example 1. Formulation Development

Four types of trastuzumab subcutaneous injection formulations were prepared as shown in Table 6. Formulations 1 to 4 commonly contain 120 mg/mL of trastuzumab, 20 mM histidine/histidine-HCl (pH 5.5), 210 mM trehalose, 10 mM methionine, and a PH20 variant. The difference among formulations 1 to 4 is the concentration of a nonionic surfactant, wherein formulation 1:0% polysorbate 20, formulation 2:0.005% polysorbate 20, formulation 3:0.04% polysorbate 20, and formulation 4:0.1% polysorbate 20.

TABLE 6

Composition of formulations

| | Formulation 1 | Formulation 2 | Formulation 3 | Formulation 4 |
|---|---|---|---|---|
| Antibody | Trastuzumab (120 mg/mL) | | | |
| Buffer | 20 mM histidine/histidine-HCl | | | |
| Stabilizer 1 | 210 mM trehalose | | | |
| Stabilizer 2 | 10 mM methionine | | | |
| Polysorbate 20 | 0% | 0.005% | 0.04% | 0.1% |
| Hyaluronidase | HP46 of SEQ ID NO: 44 (2,000 units/mL) | | | |

Working Example 2. Measurement Using Spectrophotometer

Figure 6A:
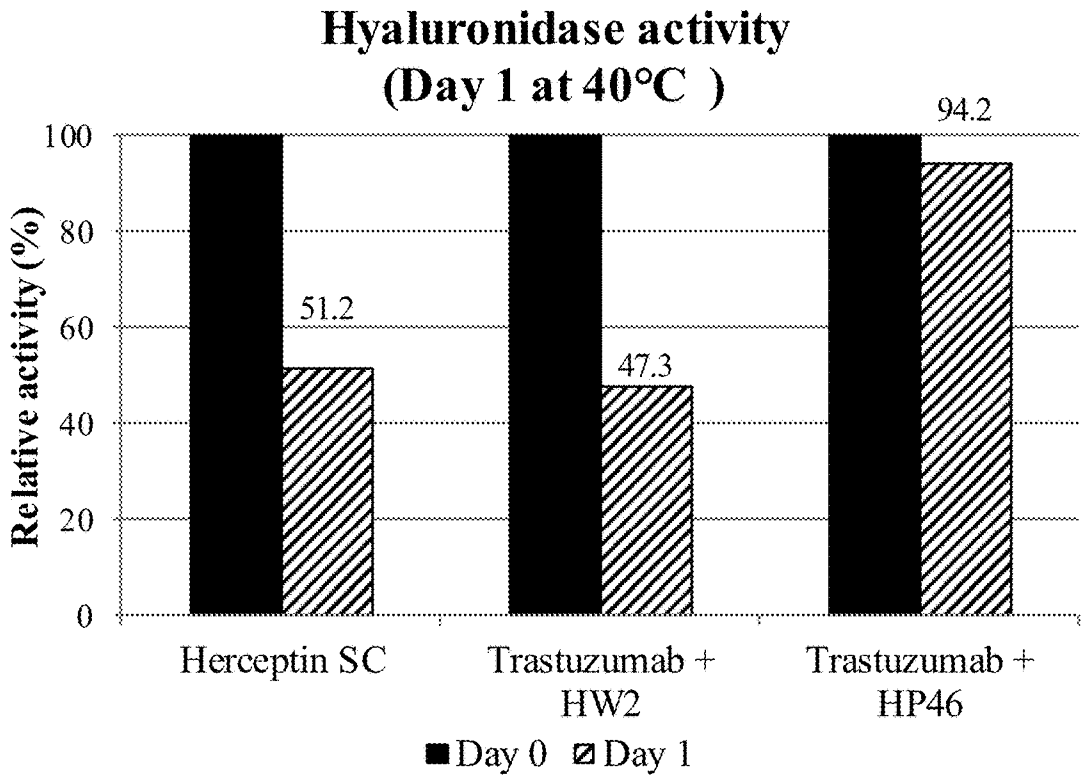
FIG. 6A illustrates the results of measuring the residual enzymatic activity of a Herceptin subcutaneous injection formulation (Herceptin SC), trastuzumab+wild-type PH20 (HW2), and trastuzumab+PH20 variant HP46 on day 0 and day 1 in a stability test under harsh conditions at 40° C.
Figure 6B:
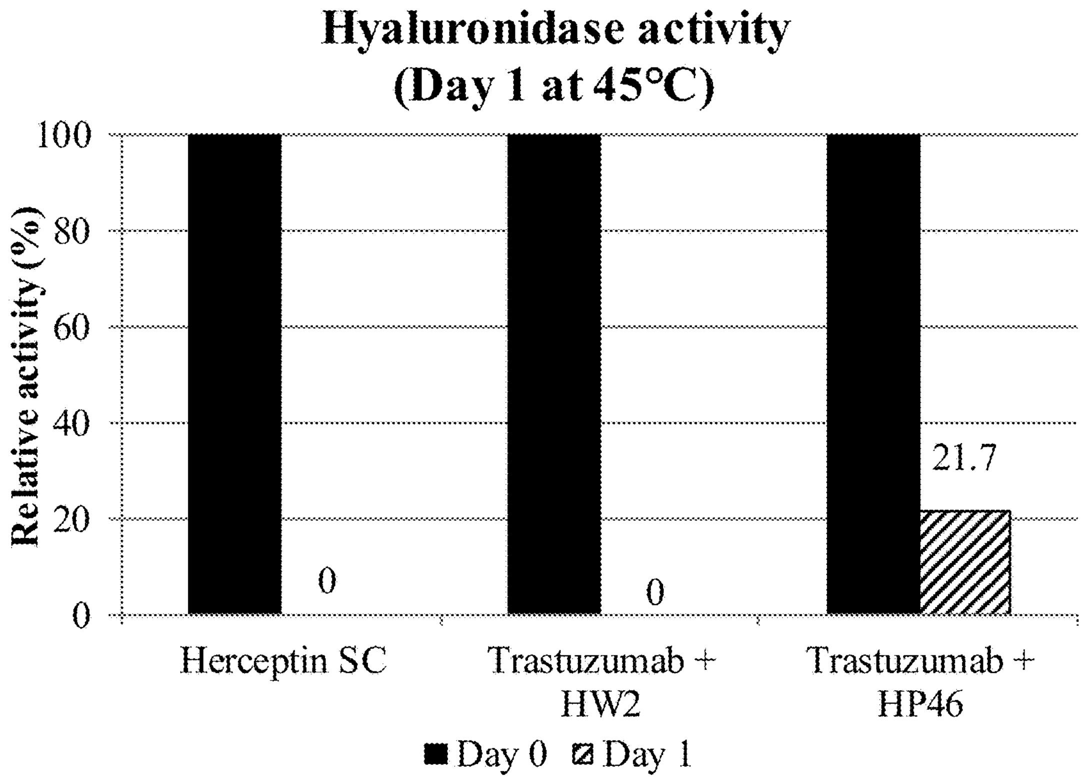
FIG. 6B illustrates the results of measuring the residual enzymatic activity of the Herceptin subcutaneous injection formulation, trastuzumab+wild-type PH20 (HW2), and trastuzumab+PH20 variant HP46 on day 0 and day 1 in a stability test under harsh conditions at 45° C.

Formulations 1 to 4 were left alone for 14 days at 45° C., and changes in protein concentration were analyzed using a spectrophotometer manufactured by Beckman. Each sample was diluted with distilled water so that the concentration of the sample was 0.4 mg/mL, and then absorbance at 280 nm of the protein was measured using a spectrophotometer. In a stability test under harsh conditions at 45° C. for 14 days, there was no significant change in protein concentration of formulations 1 to 4. However, the activity of hyaluronidase was rapidly reduced at 45° C., and thus, in the present working example, enzymatic activity was not measured (see FIGS. 6A and 6B).

Working Example 3. Investigation of Monomer Ratio of Trastuzumab Size-Exclusion in Each Formulation Using Chromatography For size-exclusion chromatography analysis, an HPLC system available from Shimadzu Prominence and a TSK-gel G3000SWXL (7.8×300 mm, 5 μm) and a TSK guard column (6.0×4.0 mm, 7 μm) were used. As a mobile phase, 0.2 M potassium phosphate (pH 6.2) containing 0.25 M potassium chloride was used. Analysis was performed for 35 minutes by applying an isocratic separation mode at a flow rate of 0.5 mL/min. The sample was diluted with an analytical solvent so that the final concentration was 10 mg/mL, and after injecting 20 μL into the HPLC column, absorbance at 280 nm of the column eluate was recorded. The monomer ratio of trastuzumab in the HPLC chromatogram was calculated and graphed.

Figure 1B:
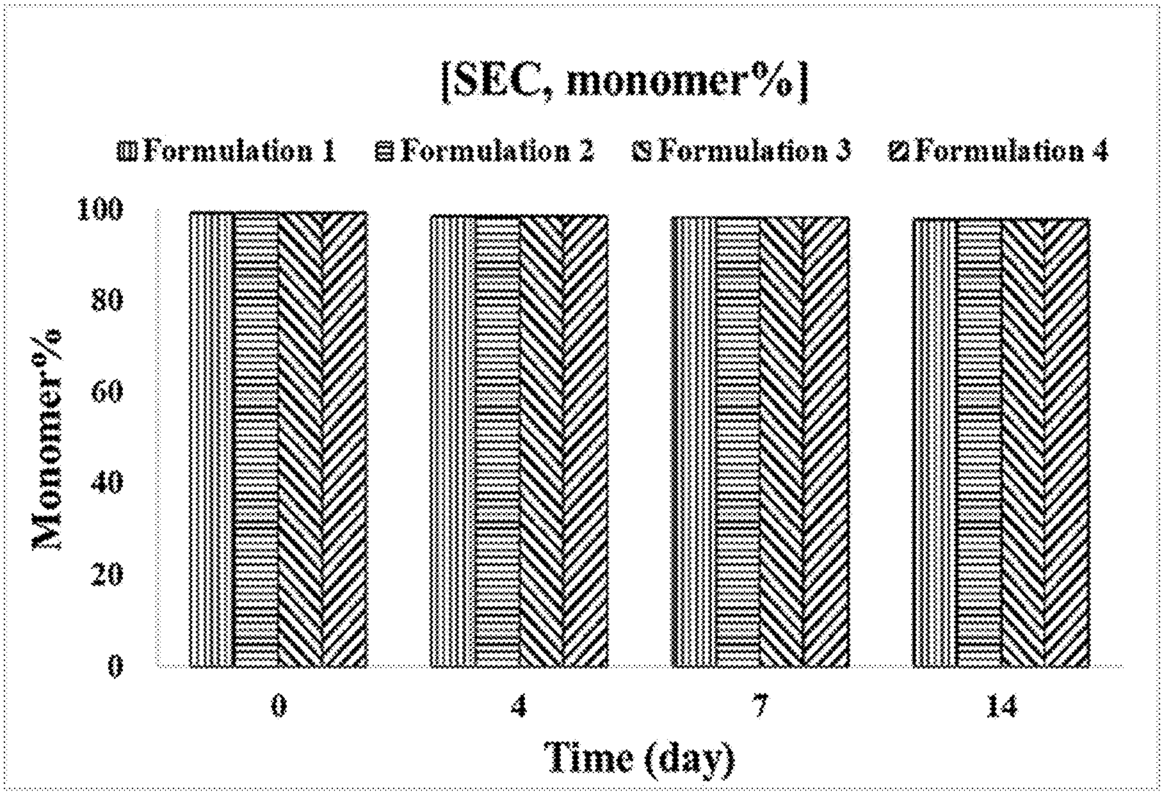
FIG. 1B illustrates a change in the purity of a trastuzumab monomeric protein according to formulation in a stability test under harsh conditions at 45° C.

When size-exclusion chromatography analysis was performed in a stability test under harsh conditions at 45° C. for 14 days, formulations 1 to 4 showed similar change patterns. The major changes were increases in high-molecular-weight (HMW) and low-molecular-weight (LMW) degradation products and a decrease in monomer content (about 1.5%), and there was no significant difference according to formulation. In conclusion, as a result of performing size-exclusion chromatography analysis in a stability test under harsh conditions at 45° C., there was no significant difference in stability profile between the formulations according to the concentration of polysorbate 20 (0 to 0.1% (w/v)) (see FIGS. 1A and 1B).

Working Example 4. Measurement of Protein Aggregation Temperature of Formulations Containing Trastuzumab and HP46

Dynamic light scattering (DLS) is used to analyze the denaturation properties of proteins attributable to heat. In the present experiment, a change in the size of a protein molecule according to the temperature change was measured and used for the purpose of calculating the protein aggregation temperature. For DLS analysis, a Zetasizer-nano-ZS instrument available from Malvern, and a quartz cuvette (ZEN2112) were used. In the analysis process, the temperature was increased from 25° C. to 85° C. at intervals of 1° C., and the sample was diluted to 1 mg/mL using each formulation buffer, and then 150 μL of the sample was added to the cuvette for analysis.

Figures 2A, 2B:
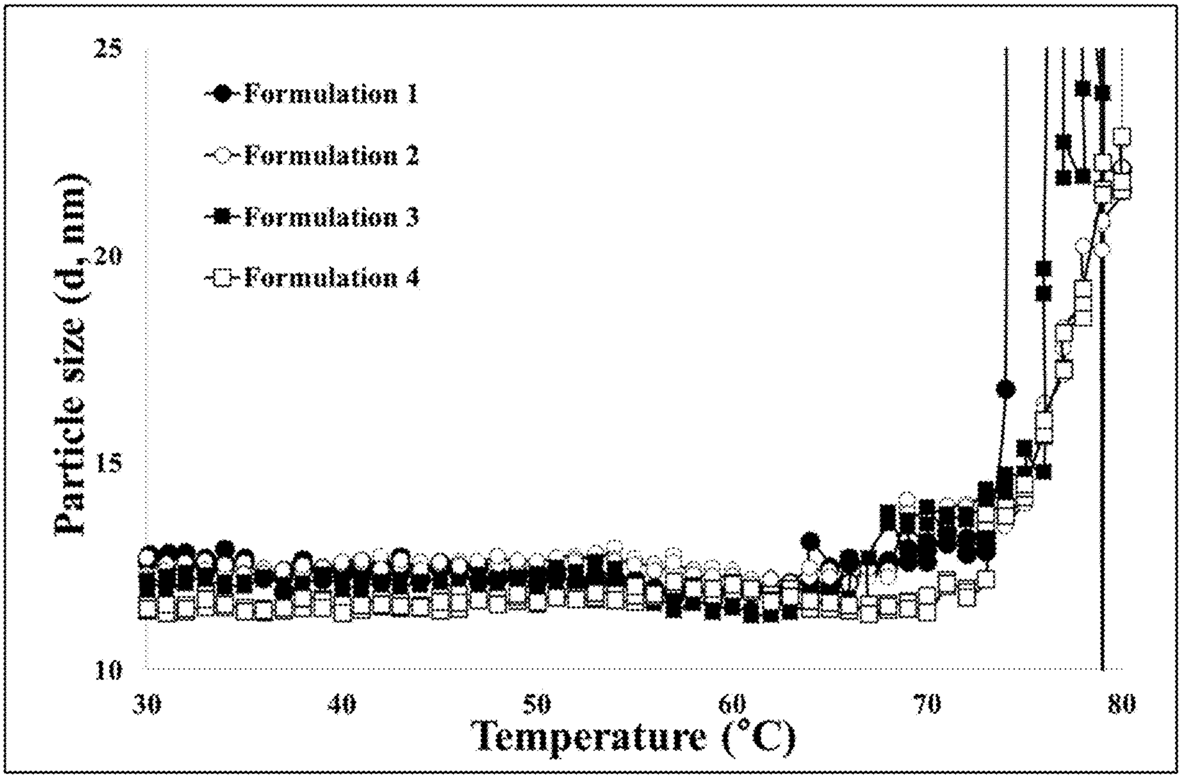
FIGS. 2A and 2B illustrate the results of measuring the protein aggregation temperatures of formulations including trastuzumab and a novel PH20 variant HP46.
Figure 3A:
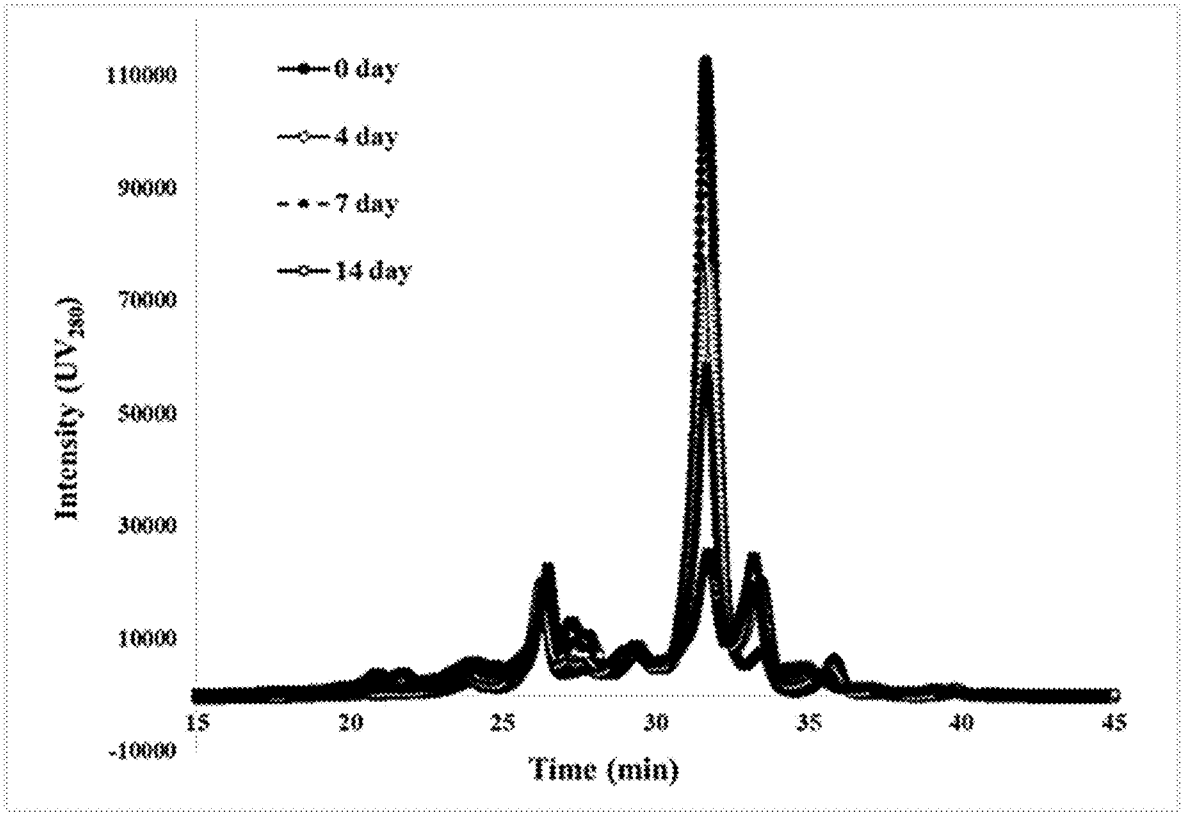
FIG. 3A is a weak cation exchange (WCX) chromatography chromatogram of trastuzumab in a stability test under harsh conditions at 45° C.
Figure 3B:
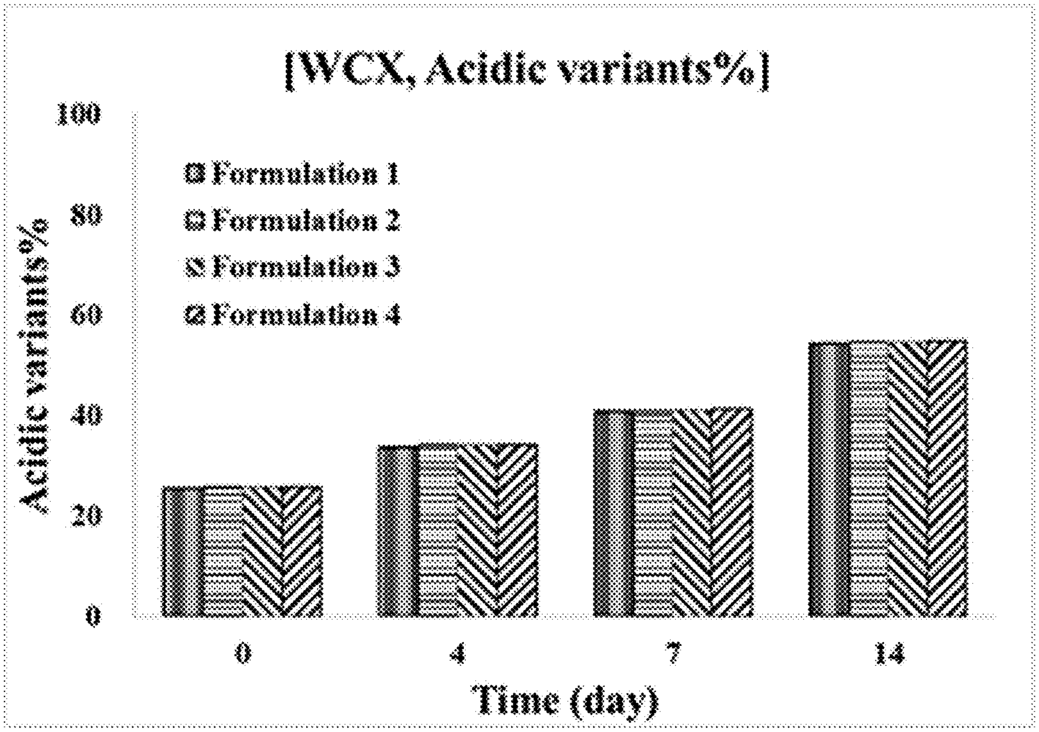
FIG. 3B illustrates changes (%) in relative contents of acidic variants in formulations in a stability test under harsh conditions at 45° C.
Figure 3C:
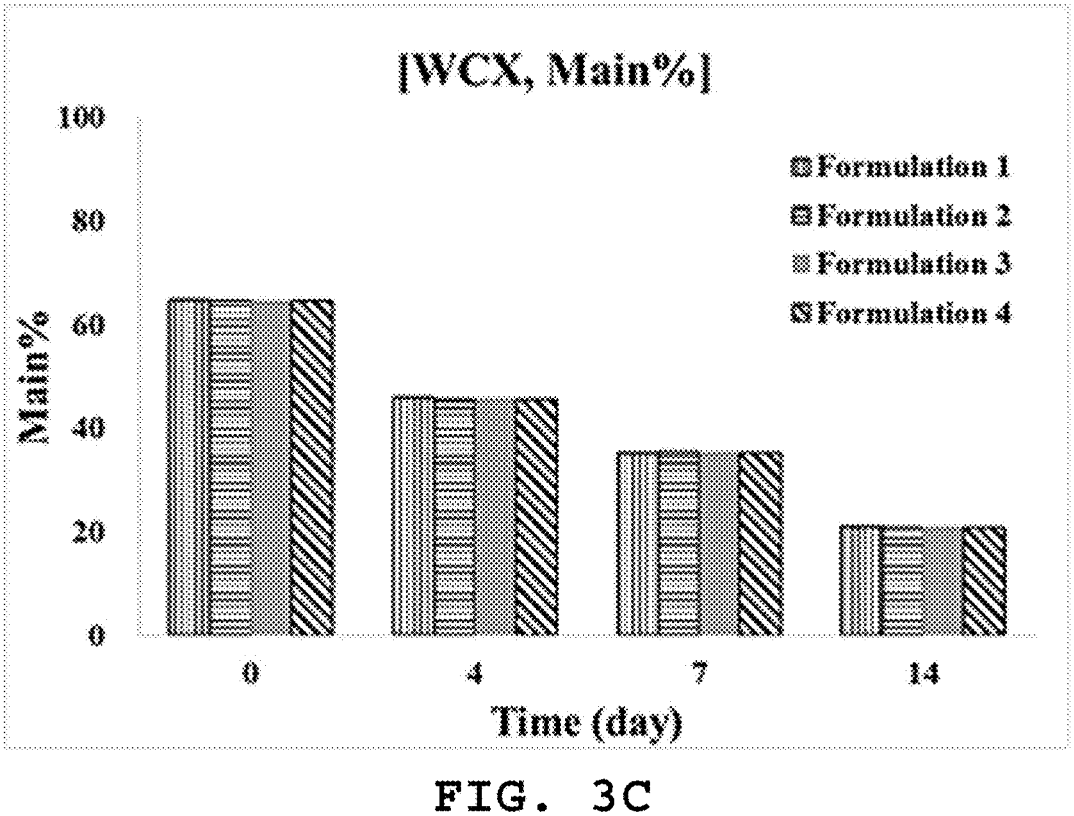
FIG. 3C illustrates changes (%) in relative contents of main peaks for formulations in a stability test under harsh conditions at 45° C.
Figure 3D:
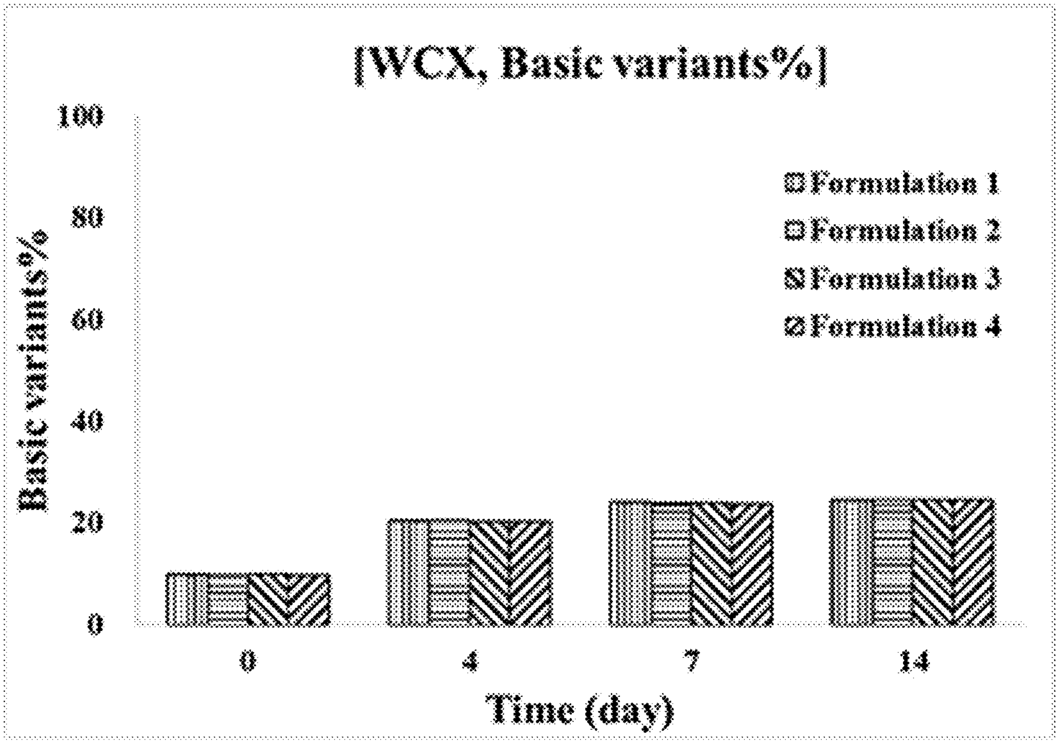
FIG. 3D illustrates changes (%) in relative contents of basic variants in formulations in a stability test under harsh conditions at 45° C.

The aggregation temperature in formulation 1, not containing polysorbate 20, was 74° C., and the aggregation temperature in formulations 2 to 4 was 76° C. (see FIGS. 2A and 2B).

Working Example 5. WCX Chromatography Measurements for Formulations Containing Trastuzumab and HP46

For WCX chromatography analysis, an HPLC system available from Shimadzu Prominence, and as columns, a TSKgel CM-STAT column (4.6×100 mm, 7 μm), a TSKgel guard gel CMSTAT (3.2 mm I. D.×1.5 cm), and the like were used. Mobile phase A is 10 mM sodium phosphate (pH 7.5) and mobile phase B is 10 mM sodium phosphate (pH 7.2) containing 0.1 M NaCl. Analysis was carried out for 55 minutes with a linear concentration gradient of 0 to 30% mobile phase B at a flow rate of 0.8 mL/min. The sample was diluted with mobile phase A so that the final concentration was 1.0 mg/mL, 80 μL of the sample was injected into HPLC, and then absorbance of a column eluate at 280 nm was recorded. The monomer ratio of trastuzumab in the HPLC chromatogram was calculated and graphed.

Formulations 1 to 4 showed similar change patterns when WCX analysis was performed in a stability test under harsh conditions at 45° C. for 14 days. Specific changes include an increase in the relative content of acidic variants (approximately 30% change for 14 days), a decrease in the relative content of main peaks (approximately 44% change for 14 days), and an increase in the relative content of basic variants (approximately 15% change for 14 days), and there was no significant difference according to formulation. In conclusion, in the WCX analysis in a stability test under harsh conditions at 45° C., protein stability according to polysorbate 20 (0 to 0.1%) was similar (see FIGS. 3A-3D).

Working Example 6. Formulation Development

Three types of trastuzumab subcutaneous injection formulations were prepared as described in Table 7. Formulations 5 to 7 commonly include 120 mg/mL of trastuzumab, 20 mM histidine/histidine-HCl (pH 5.5), 210 mM trehalose, 10 mM methionine, and HP46. The difference between formulations 5 to 7 is the ingredient of stabilizer 3, comprising formulation 5:0.04% polysorbate 20, formulation 6:50 mm Lys-Lys, and formulation 3:glycine.

TABLE 7

Composition of formulations

| | Formulation 5 | Formulation 6 | Formulation 7 |
|---|---|---|---|
| Antibody | Trastuzumab (120 mg/mL) | | |
| Buffer | 20 mM histidine/histidine-HCl | | |
| Stabilizer 1 | 210 mM trehalose | | |
| Stabilizer 2 | 10 mM methionine | | |
| Stabilizer 3 | 0.04% polysorbate 20 | 50 mM Lys-Lys | 50 mM glycine |
| Hyaluronidase | HP46 of SEQ ID NO: 44 (2,000 units/mL) | | |

Working Example 7. Measurement Using Spectrophotometer

Formulations 5 to 7 were left alone for 14 days at 45° C., and changes in protein concentration were analyzed using a spectrophotometer manufactured by Beckman. Each sample was diluted with distilled water so that the concentration of the sample was 0.4 mg/mL, and then absorbance of the protein at 280 nm was measured using a spectrophotometer. In a stability test under harsh conditions at 45° C. for 14 days, there was no significant change in protein concentration of formulations 5 to 7. However, the activity of hyaluronidase was rapidly reduced at 45° C., and thus, in the present working example, enzymatic activity was not measured (see FIGS. 6A and 6B).

Working Example 8. Investigation of Monomer Ratio of Trastuzumab in Each Formulation Using Size-Exclusion Chromatography For size-exclusion chromatography analysis, an HPLC system available from Shimadzu Prominence and as columns, a TSK-gel G3000SWXL (7.8×300 mm, 5 μm) and a TSK guard column (6.0×4.0 mm, 7 μm) were used. As a mobile phase, 0.2 M potassium phosphate (pH 6.2) containing 0.25 M potassium chloride was used. An isocratic separation mode was applied at a flow rate of 0.5 mL/min for 35 minutes. The sample was diluted with an analytical solvent so that the final concentration was 10 mg/mL, and after injecting 20 μL of the sample into the HPLC, absorbance at 280 nm was measured. The monomer ratio of trastuzumab in the HPLC chromatogram was calculated and graphed.

Figure 4:
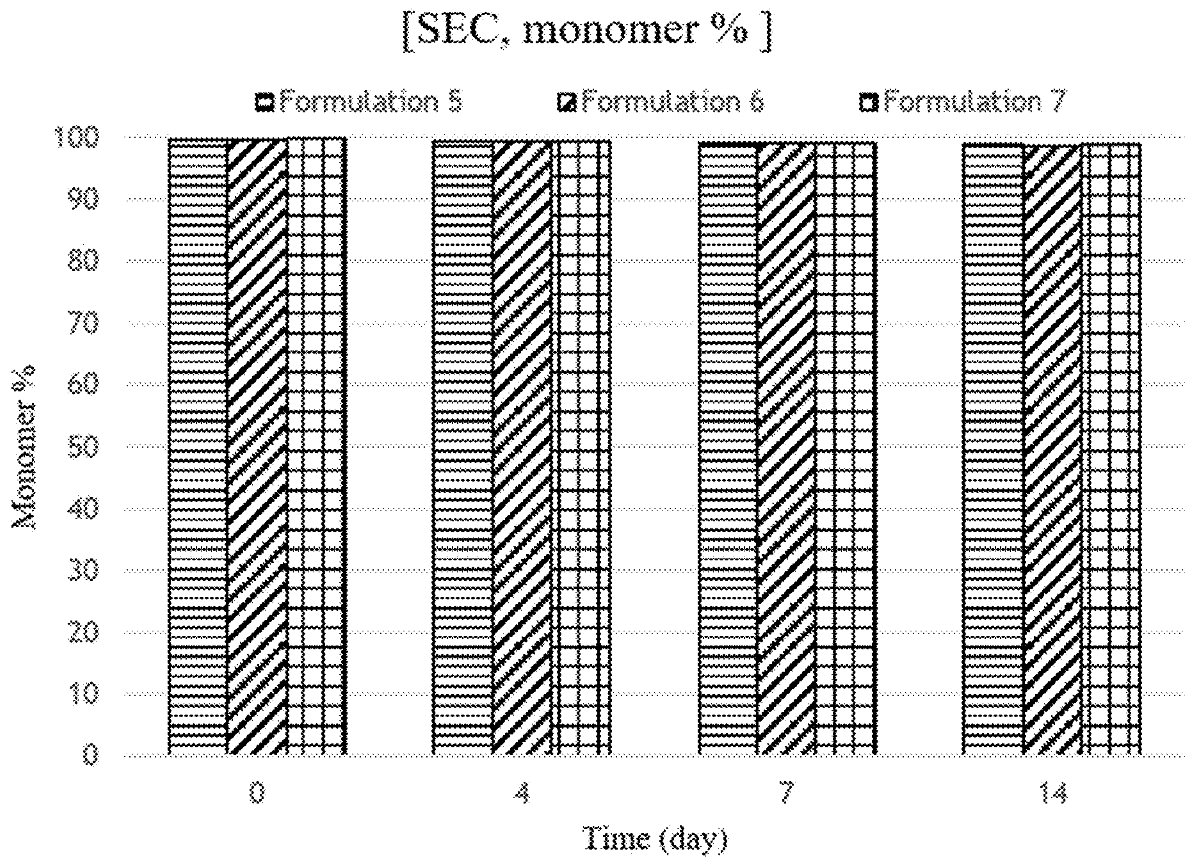
FIG. 4 illustrates changes in the purity of a trastuzumab monomeric protein in Formulations 5 to 7 in a stability test under harsh conditions at 45° C.

When size-exclusion chromatography analysis was performed in a stability test under harsh conditions at 45° C. for 14 days, formulations 5 to 7 showed similar change patterns. The major changes were increases in high-molecular-weight (HMW) and low-molecular-weight (LMW) impurities and a decrease in monomer content (about 1.5%), and there was no significant difference according to formulation. In conclusion, as a result of performing size-exclusion chromatography analysis in a stability test under harsh conditions at 45° C., similar protein stability was shown in 0.04% polysorbate 20, 50 mM Lys-Lys, and 50 mM glycine formulations (see FIG. 4).

Working Example 9. WCX Chromatography Analysis of Formulations Containing Trastuzumab and HP46

For WCX chromatography analysis, an HPLC system available from Shimadzu Prominence, and as columns, a TSKgel CM-STAT (4.6×100 mm, 7 μm), a TSKgel guard gel CMSTAT (3.2 mm I.D.x 1.5 cm were used. Mobile phase A is 10 mM sodium phosphate (pH 7.5) and mobile phase B is 10 mM sodium phosphate (pH 7.2) containing 0.1 M NaCl. Analysis was performed for 55 minutes by applying a separation mode of a linear concentration gradient of 0 to 30% at a flow rate of 0.8 mL/min. The sample was diluted with mobile phase A so that the final concentration was 1.0 mg/mL, 80 μL of the sample was injected into HPLC, and then absorbance at 280 nm was recorded. The monomer ratio of trastuzumab in the HPLC chromatogram was calculated and graphed.

Figure 5A:
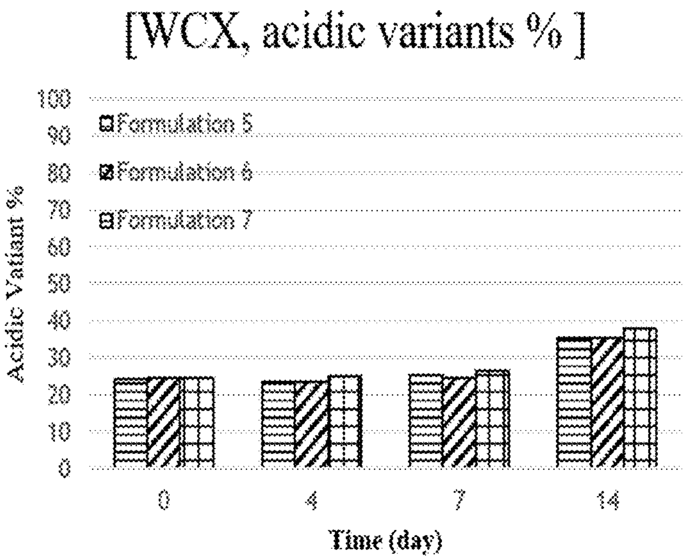
FIG. 5A illustrates changes (%) in relative contents of acidic variants according to formulations 5 to 7 in a stability test under harsh conditions at 45° C.
Figure 5B:
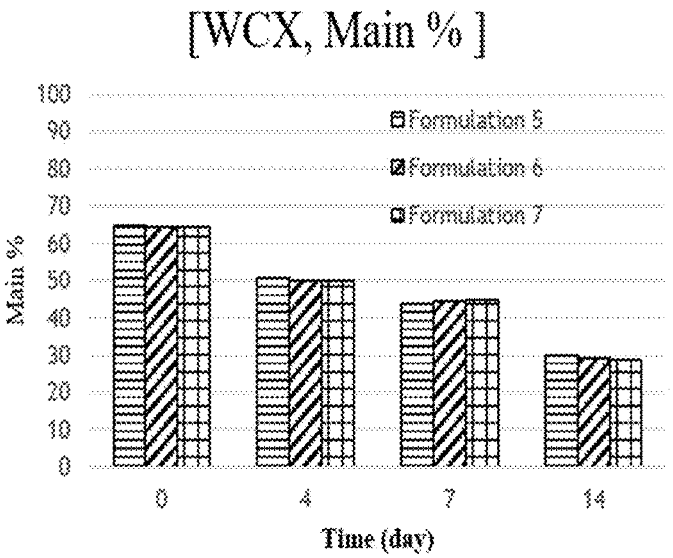
FIG. 5B illustrates changes (%) in relative contents of main peaks according to Formulations 5, 6, and 7 in a stability test under harsh conditions at 45° C.
Figure 5C:
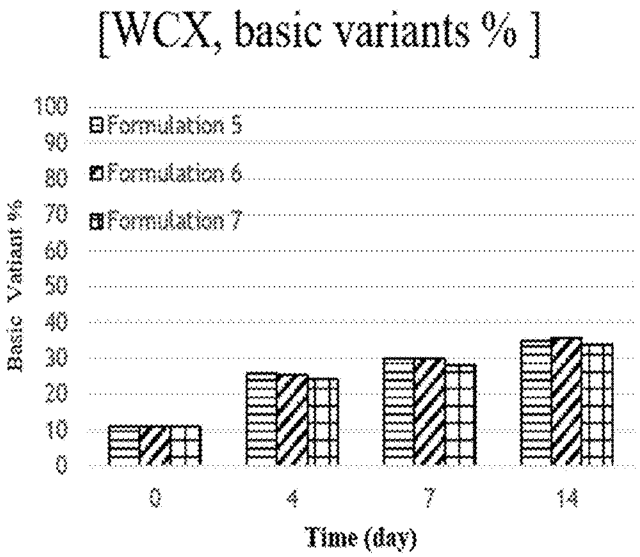
FIG. 5C illustrates changes (%) in relative contents of basic variants according to Formulations 5, 6, and 7 in a stability test under harsh conditions at 45° C.

Formulations 5 to 7 showed similar change patterns when WCX analysis was performed in a stability test under harsh conditions at 45° C. for 14 days. Specific changes include an increase in the relative content of acidic variants (approximately 30% change for 14 days), a decrease in the relative content of main peaks (approximately 44% change for 14 days), and an increase in the relative content of basic variants (approximately 15% change for 14 days), and there was no significant difference according to formulation. In conclusion, as a result of performing WCX analysis in a stability test under harsh conditions at 45° C., similar protein stability was shown in 0.04% polysorbate 20, 50 mM Lys-Lys, and 50 mM glycine formulations (see FIGS. 5A-5C).

Working Example 10. Stability Evaluation of HP46 According to Temperatures of 40° C. And 45° C. In Subcutaneous Injection Formulations of Trastuzumab and HP46

To evaluate the stability of HP46 in subcutaneous injection formulations of trastuzumab, trastuzumab (120 mg/mL) and PH20 (200 units/mL) were mixed. At this time, the buffer used contained 20 mM Histidine (pH 5.5), 210 mM trehalose, 10 mM methionine, and 0.04% polysorbate 20. The enzymatic activity of a control sample was measured on day 0, and the experimental samples were left at 40° C. or 45° C. for one day, and then the enzymatic activity of each sample was measured.

Each of a Herceptin subcutaneous injection formulation, trastuzumab+HW2, and trastuzumab+HP46 was left at 40° C. for one day, and then the activity of hyaluronidase was measured, and as a result, the respective cases exhibited activity of 51%, 47%, and 94%, which indicates that HP46 had a great thermal stability at 40° C. (see FIGS. 6A and 6B). In addition, the Herceptin subcutaneous injection formulation, trastuzumab+HW2, and trastuzumab+HP46 were left at 45° C. for one day, and then the activity of hyaluronidase was measured, and as a result, the enzymatic activity of the Herceptin subcutaneous injection formulation and trastuzumab+HW2 ceased, but the enzymatic activity of trastuzumab+HP46 remained 22% (see FIGS. 6A and 6B).

Working Example 11. Formulation Development

Three types of trastuzumab subcutaneous injection formulations were prepared as shown in Table 8. Formulations 8 to 10 commonly contain 120 mg/mL of trastuzumab, 20 mM histidine/histidine-HCl (pH 5.5), 210 mM trehalose, 10 mM methionine, and a PH20 variant. The difference among formulations 8 to 10 is the concentration of a nonionic surfactant, wherein formulation 8:0% polysorbate 20, formulation 9:0.005% polysorbate 20, and formulation 10:0.04% polysorbate 20.

TABLE 8

| Composition of formulations | | | |
|---|---|---|---|
| | Formulation 8 | Formulation 9 | Formulation 10 |
| Antibody | Trastuzumab (120 mg/mL) | | |
| Polysorbate 20 | 0% | 0.005% | 0.04% |
| Buffer | 20 mM histidine/histidine-HCl | | |
| Stabilizer 1 | 210 mM trehalose | | |
| Stabilizer 2 | 10 mM methionine | | |
| pH | 5.5 | | |
| Hyaluronidase | HP46 of SEQ ID NO: 44 (2,000 units/mL) | | |

Working Example 12. Measurement Using Spectrophotometer

Formulations 8 to 10 were left alone for 14 days at 40° C., and changes in protein concentration were analyzed using a spectrophotometer manufactured by Beckman. Each sample was diluted with distilled water so that the concentration of the sample was 0.4 mg/mL, and then absorbance at 280 nm of the protein was measured using a spectrophotometer. In a stability test under harsh conditions at 40° C. for 14 days, there was no significant difference in protein concentrations of formulations 8 to 10.

Working Example 13. Investigation of Monomer Ratio of Trastuzumab in Each Formulation Using Size-Exclusion Chromatography For size-exclusion chromatography analysis, an HPLC system available from Shimadzu Prominence and as columns, a TSK-gel G3000SWXL (7.8×300 mm, 5 μm) and a TSK guard column (6.0×4.0 mm, 7 μm) were used. As a mobile phase, 0.2 M potassium phosphate (pH 6.2) containing 0.25 M potassium chloride was used. Analysis was performed for 35 minutes by applying an isocratic separation mode at a flow rate of 0.5 mL/min. The sample was diluted with an analytical solvent so that the final concentration was 10 mg/mL, and after injecting 20 μL of the sample into the HPLC column, absorbance at 280 nm was measured. The monomer ratio of trastuzumab in the HPLC chromatogram was calculated and graphed.

Figure 7:
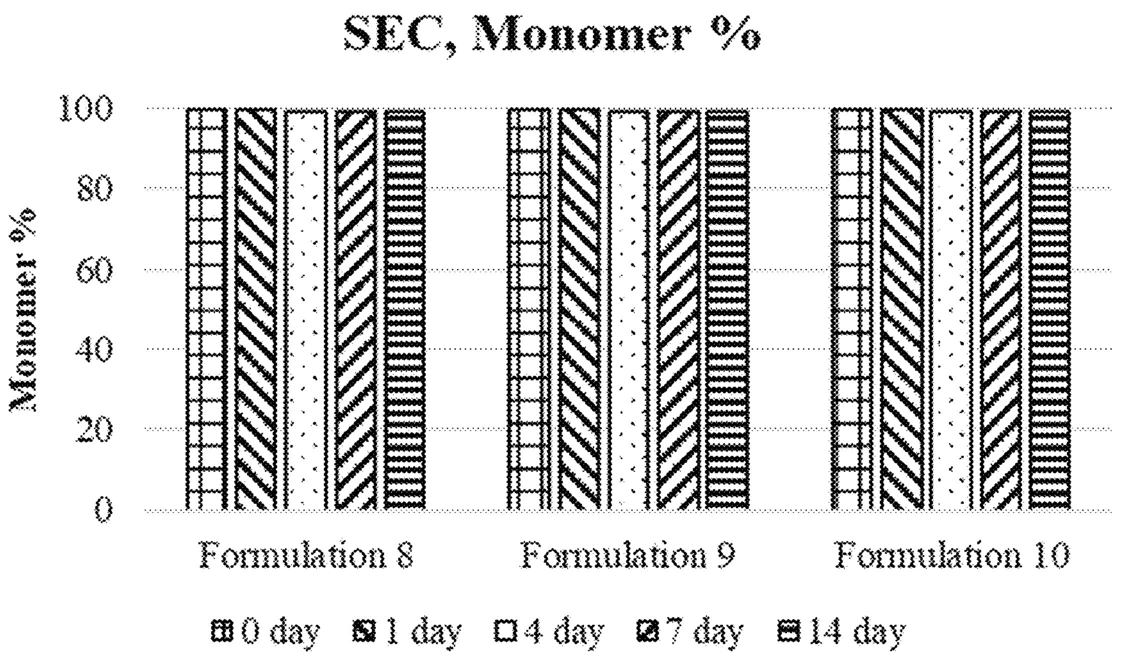
FIG. 7 illustrates size-exclusion chromatography analysis results of Formulations 8, 9, and 10 in a stability test under harsh conditions at 40° C. for 14 days.

When size-exclusion chromatography analysis was performed in a stability test under harsh conditions at 40° C. for 14 days, formulations 8 to 10 showed similar change patterns. The major changes were increases in high-molecular-weight (HMW) and low-molecular-weight (LMW) degradation products and a decrease in monomer content (about less than 1.0%), and there was no significant difference according to formulation. In conclusion, as a result of performing size-exclusion chromatography analysis in a stability test under harsh conditions at 40° C., there was no significant difference in stability profile between the formulations according to the concentration of polysorbate 20 (0 to 0.04%) (see FIG. 7).

Working Example 14. Measurement of Protein Aggregation Temperature for Formulations Containing Trastuzumab and HP46

Dynamic light scattering (DLS) is used to analyze the denaturation properties of proteins attributable to heat in the protein drug field. In the present experiment, a change in the size of a protein molecule according to the temperature change was measured and used for the purpose of calculating the protein aggregation temperature. For DLS analysis, a Zetasizer-nano-ZS instrument available from Malvern, and a quartz cuvette (ZEN2112) were used. In the analysis process, the temperature was increased from 25° C. to 85° C. at intervals of 1° C., and the sample was diluted to 1 mg/mL using each formulation buffer, and then 150 μL of the sample was added to the cuvette for analysis.

Figure 8A:
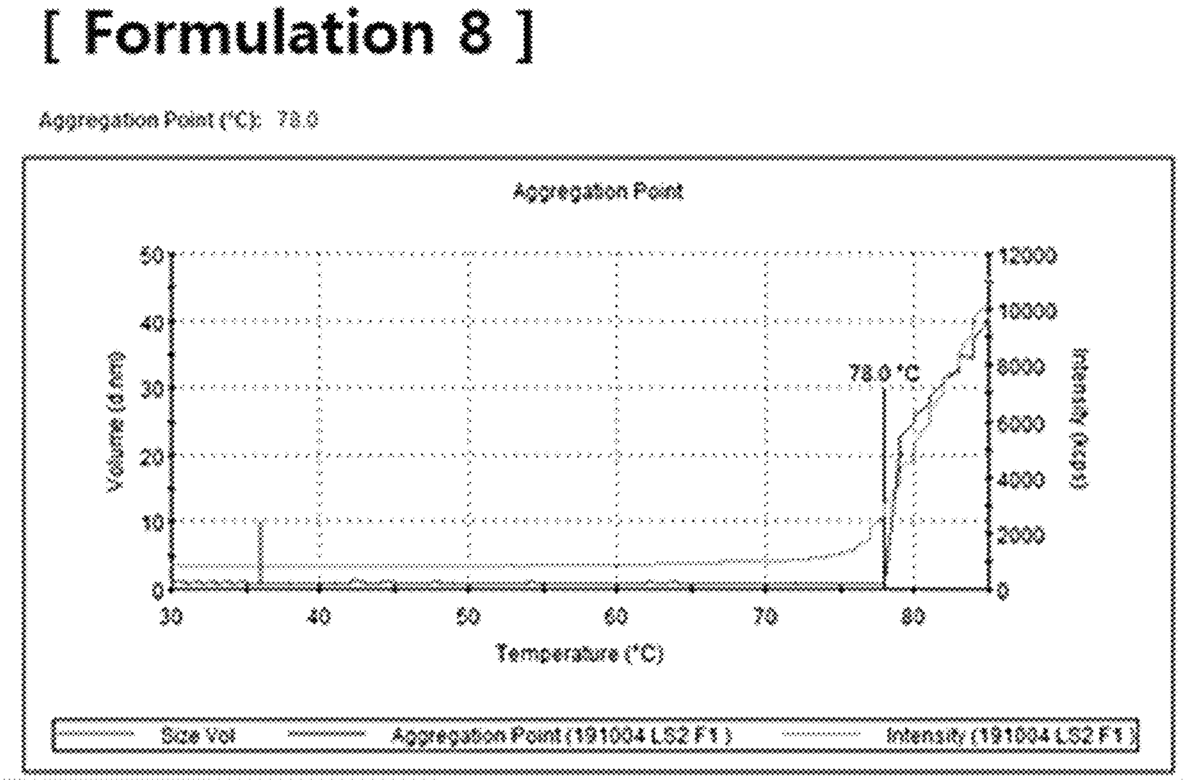
FIG. 8A illustrates the results of measuring changes in protein particle size of Formulations 8,9, and 10, respectively, using DLS equipment.
Figure 8A:
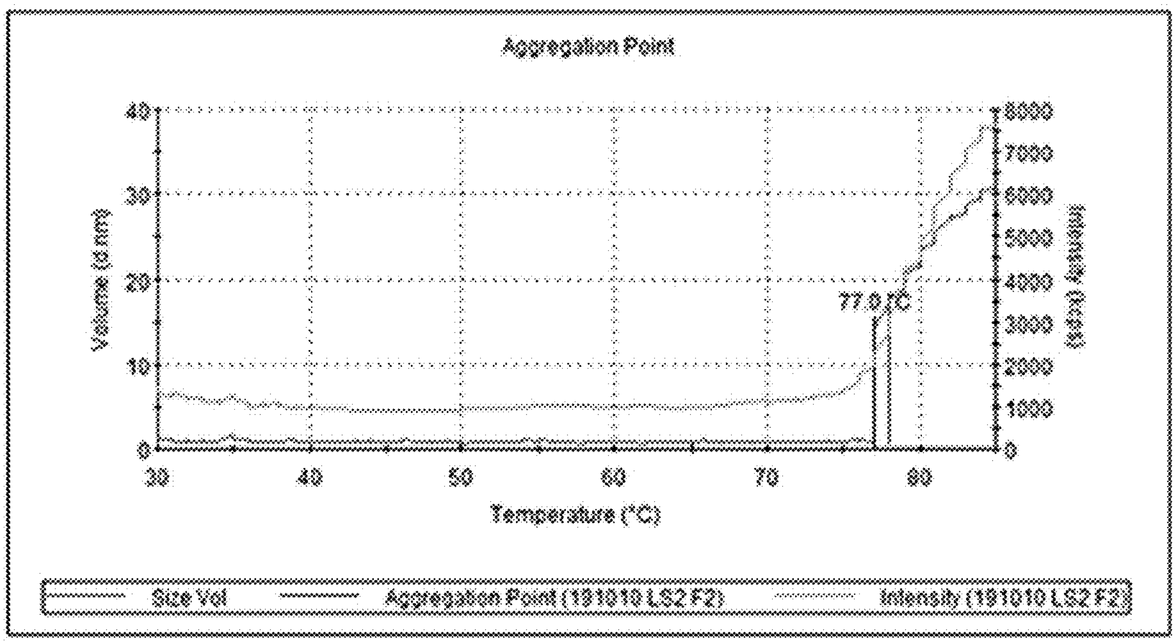
Figure 8A:
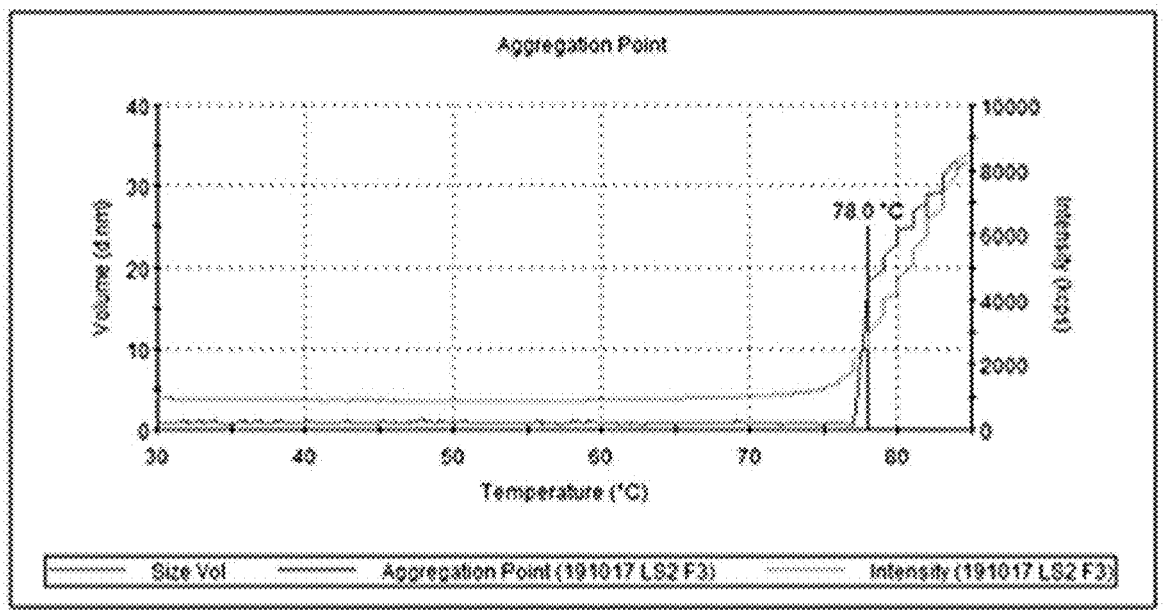
Figure 9A:
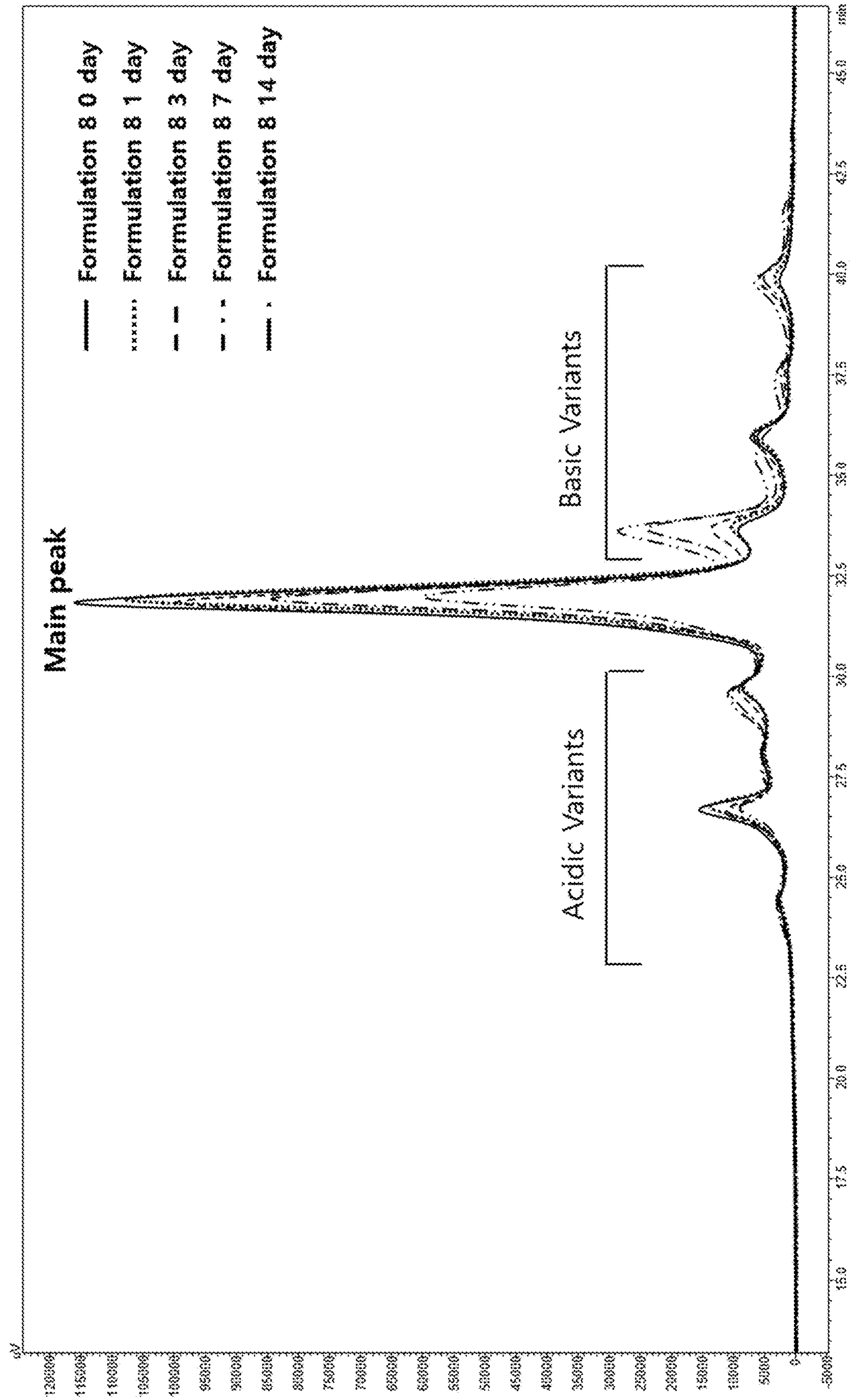
FIG. 9A illustrates a weak cation exchange (WCX) chromatography chromatogram of Formulation 8 in a stability test under harsh conditions at 40° C.
Figure 9B:
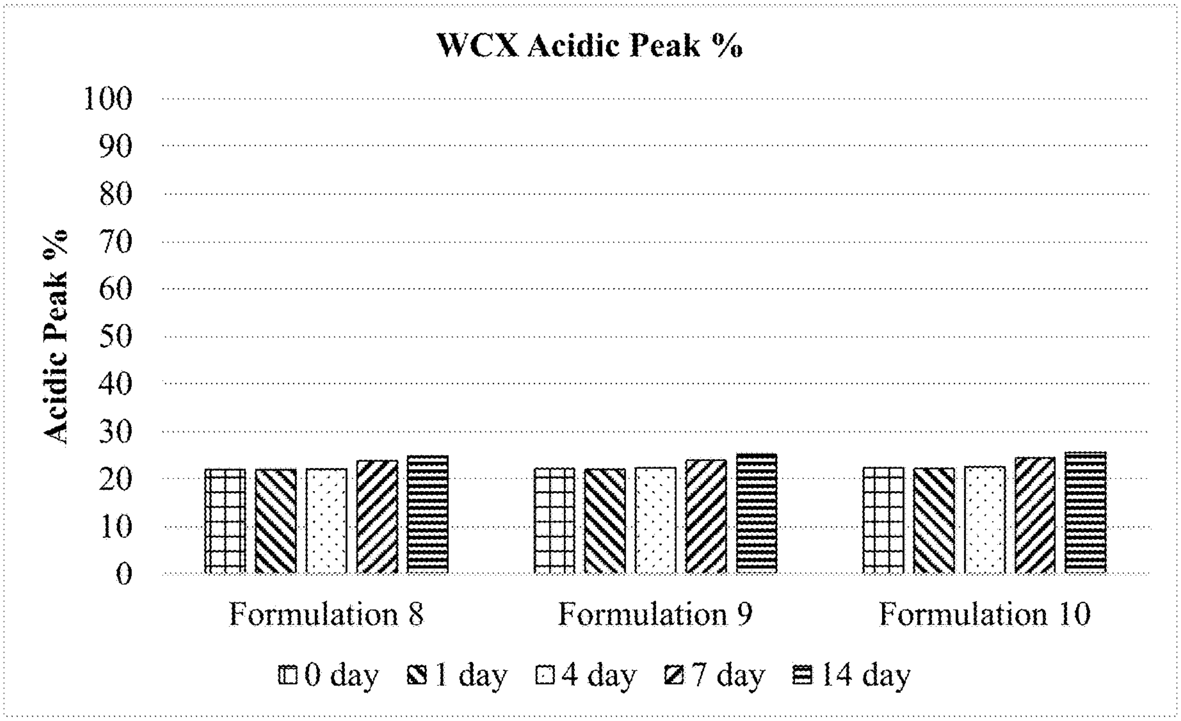
FIG. 9B illustrates changes (%) in relative contents of acidic variants in Formulations 8 to 10 in a stability test under harsh conditions at 40° C.
Figure 9C:
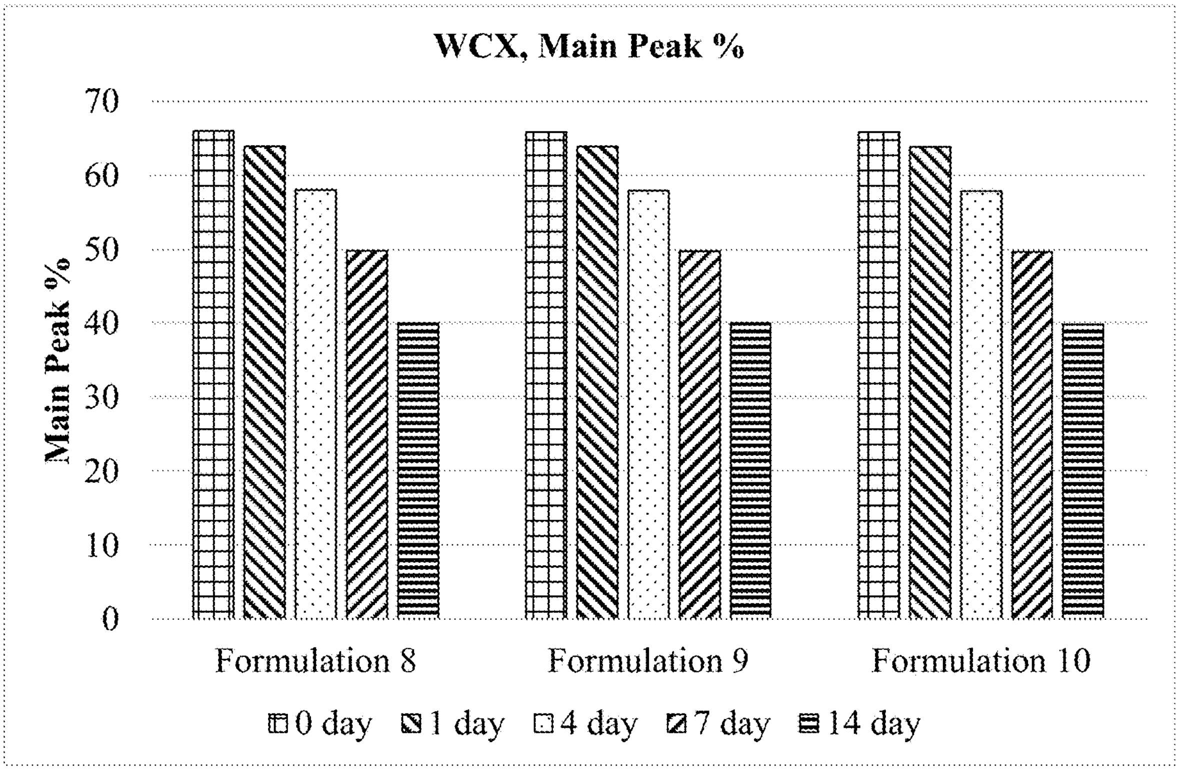
FIG. 9C illustrates changes (%) in relative contents of main peaks for Formulations 8 to 10 in a stability test under harsh conditions at 40° C.
Figure 9D:
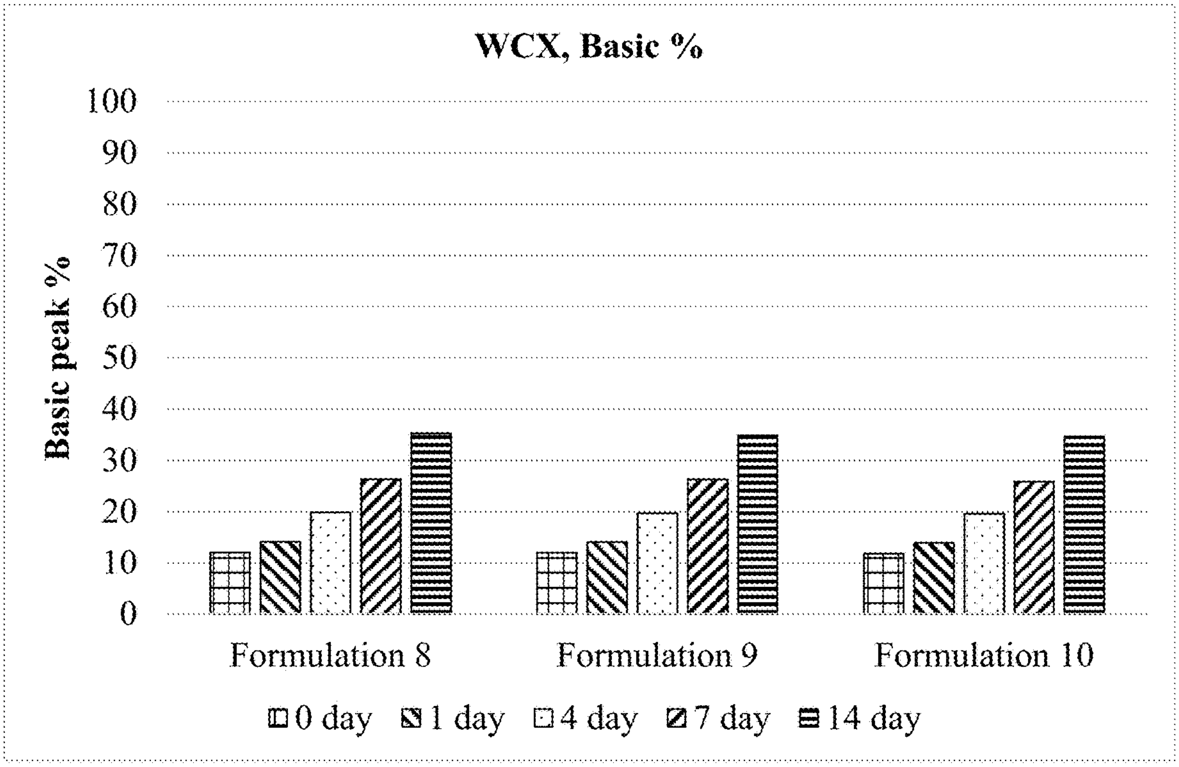
FIG. 9D illustrates changes (%) in relative contents of basic variants in Formulations 8, 9, and 10 in a stability test under harsh conditions at 40° C.

The aggregation temperature in formulation 8, not containing polysorbate 20, was 78.3° C., formulation 9 exhibited an aggregation temperature of 77.3° C., and formulation 10 exhibited an aggregation temperature of 77.7° C. In Working Example 13, no change in monomer ratio of the protein was shown despite not containing polysorbate 20, and as a result of comparing the case of not containing polysorbate 20 with the case of containing polysorbate 20, it was found that there was no difference in aggregation between proteins. These results indicate that a minimum amount of polysorbate 20 is not necessarily required for subcutaneous injection formulations of trastuzumab (see FIGS. 8A and 8B).

Working Example 15. WCX Chromatography Analysis for Formulations Containing Trastuzumab and HP46

For WCX chromatography analysis, an HPLC system available from Shimadzu Prominence, and as columns, a TSKgel CM-STAT column (4.6×100 mm, 7 μm), a TSKgel guard gel CMSTAT (3.2 mm I. D.×1.5 cm), and the like were used. Mobile phase A is 10 mM sodium phosphate (pH 7.5) and mobile phase B is 10 mM sodium phosphate (pH 7.2) containing 0.1 M NaCl. Analysis was carried out for 55 minutes with a linear concentration gradient of 0 to 30% mobile phase B at a flow rate of 0.8 mL/min. The sample was diluted with mobile phase A so that the final concentration was 1.0 mg/mL, 80 μL of the sample was injected into HPLC, and then absorbance of a column eluate at 280 nm was recorded. The monomer ratio of trastuzumab in the HPLC chromatogram was calculated and graphed.

Formulations 8 to 10 showed similar change patterns when WCX analysis was performed in a stability test under harsh conditions at 40° C. for 14 days. Specific changes include an increase in the relative content of acidic variants (approximately 10% change for 14 days), a decrease in the relative content of main peaks (approximately 40% change for 14 days), and an increase in the relative content of basic variants (approximately 300% change for 14 days), and there was no significant difference according to formulation. In conclusion, in the WCX analysis in a stability test under harsh conditions at 40° C., protein stability according to polysorbate 20 (0 to 0.04%) was similar (see FIGS. 9A-9D).

Working Example 16. Measurement of Enzymatic Activity for Formulations Containing Trastuzumab and HP46

The turbidimetric assay method for measuring enzymatic activity is a method of measuring, by absorbance, the degree to which an aggregate is formed by binding of residual hyaluronic acid to acidified albumin (BSA), and when hyaluronic acid is hydrolyzed by PH20, the extent of binding to albumin is reduced, resulting in reduced absorbance. BTH (Sigma) as a standardized product was diluted to 1, 2, 5, 7.5, 10, 15, 20, 30, 50, and 60 units/mL and prepared in each tube. Purified PH20 variant samples were diluted with enzyme diluent buffer (20 mM Tris·HCl, pH 7.0, 77 mM NaCl, 0.01% (w/v) bovine serum albumin) to 100X, 300X, 600X, 1200X, and 2400X and prepared in each tube. In fresh tubes, the hyaluronic acid solution, having a concentration of 3 mg/mL, was diluted 10-fold to a concentration of 0.3 mg/mL so that the volume of each tube became 180 μL. 60 μL of the sample containing hyaluronidase was added to the diluted hyaluronic acid solution and mixed therewith, and allowed to react at 37° C. for 45 minutes. After the reaction was completed, 50 μL of the reacted enzyme and 250 μL of an acidic albumin solution were added to each well of a 96-well plate and shaken for 10 minutes, and then absorbance at 600 nm was measured using a spectrophotometer.

Figure 10:
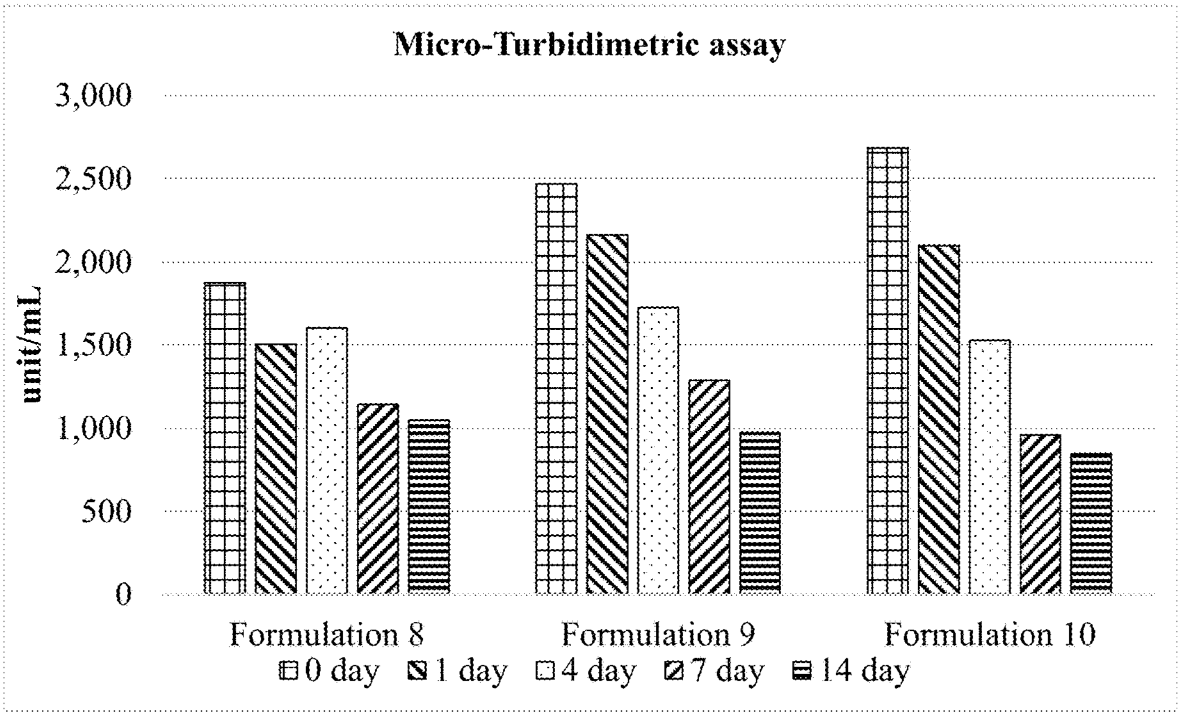
FIG. 10 illustrates changes (%) in relative enzymatic activity of Formulations 8, 9, and 10 in a stability test under harsh conditions at 40° C.

As a result of performing activity analysis in a stability test under harsh conditions at 40° C. for 14 days, it was found that the higher the concentration of polysorbate 20, the greater the reduction in activity over time (see FIG. 10).

Working Example 17. Formulation Development

Three trastuzumab subcutaneous injection formulations were prepared as shown in Table 9. Formulations 11 to 13 commonly contain 120 mg/mL of trastuzumab, 20 mM histidine/histidine-HCl (pH 5.5), 210 mM trehalose, 10 mM methionine, and a PH20 variant. The difference among formulations 11 to 13 is the concentration of a nonionic surfactant, wherein formulation 11:0% polysorbate 80, formulation 12:0.005% polysorbate 80, and formulation 13:0.04% polysorbate 80.

TABLE 9

Composition of formulations

| | Formulation 11 | Formulation 12 | Formulation 13 |
|---|---|---|---|
| Antibody | Trastuzumab (120 mg/mL) | | |
| Polysorbate 80 | 0% | 0.005% | 0.04% |
| Buffer | 20 mM histidine/histidine-HCl | | |
| Stabilizer 1 | 210 mM trehalose | | |
| Stabilizer 2 | 10 mM methionine | | |
| pH | 5.5 | | |
| Hyaluronidase | HP46 of SEQ ID NO: 44 (2,000 units/mL) | | |

Figure 11:
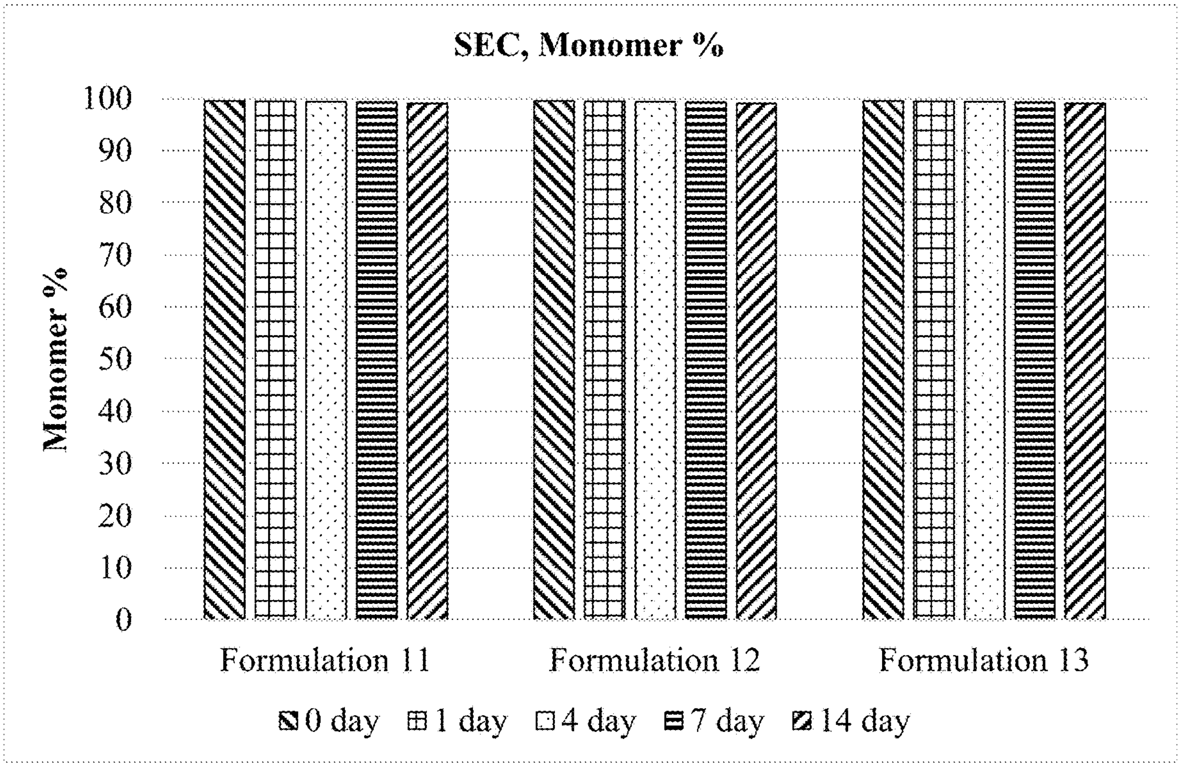
FIG. 11 illustrates changes in the purity of trastuzumab monomers of Formulations 11 to 13 in a stability test under harsh conditions at 40° C.
Figure 12A:
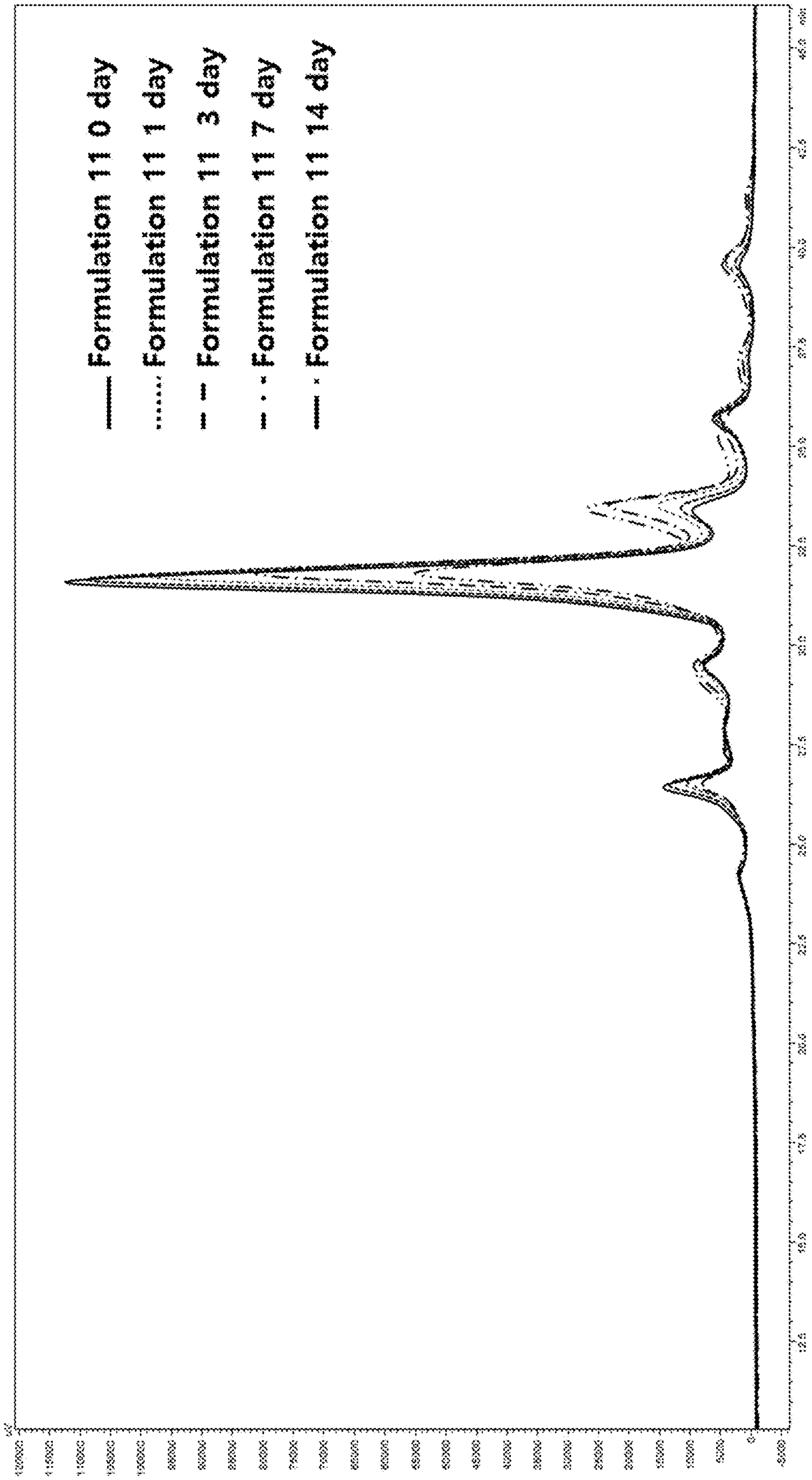
FIG. 12A illustrates a weak cation exchange (WCX) chromatography chromatogram of Formulation 11 in a stability test under harsh conditions at 40° C.
Figure 12B:
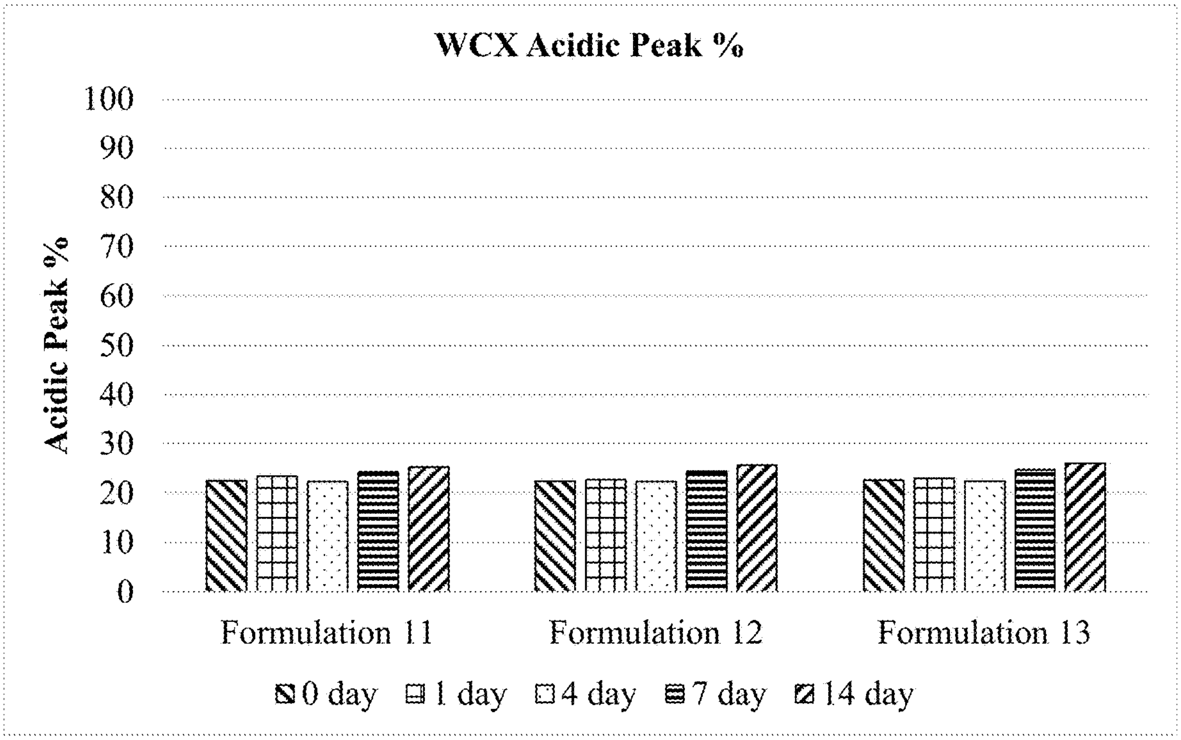
FIG. 12B illustrates changes (%) in relative contents of acidic variants in formulations 11 to 13 in a stability test under harsh conditions at 40° C.
Figure 12C:
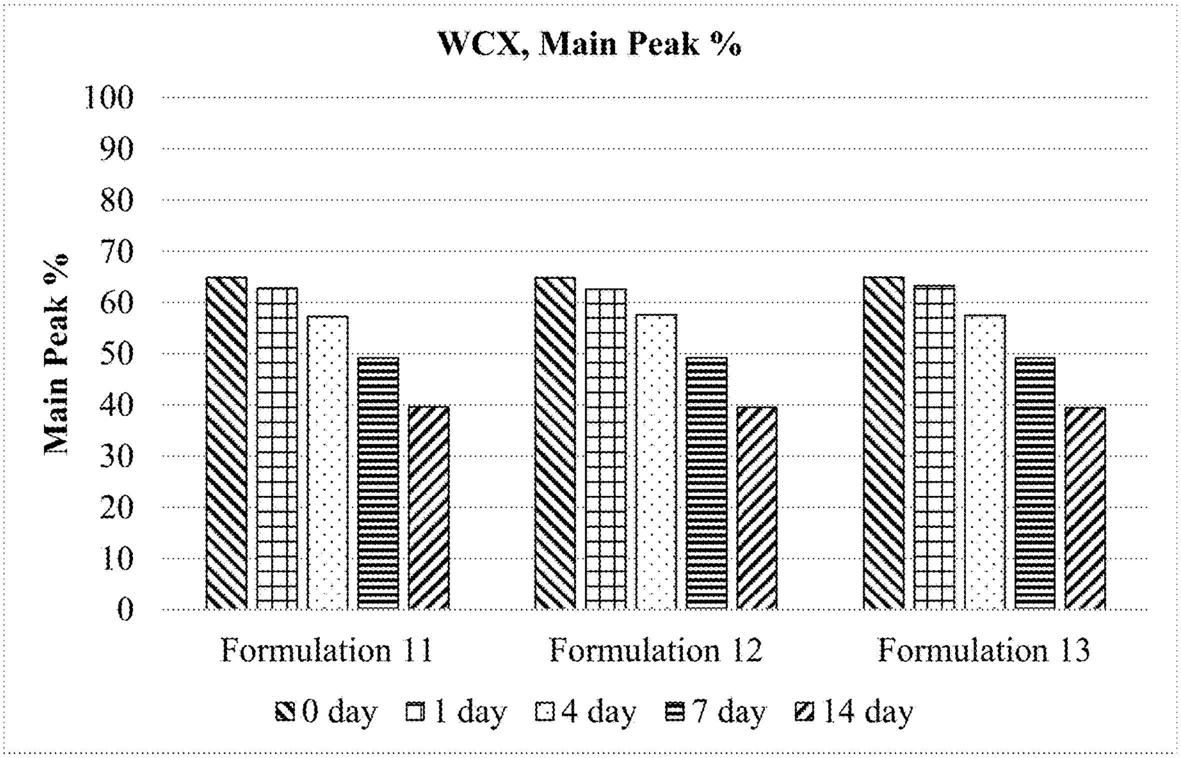
FIG. 12C illustrates changes (%) in relative contents of main peaks for Formulations 11 to 13 in a stability test under harsh conditions at 40° C.
Figure 12D:
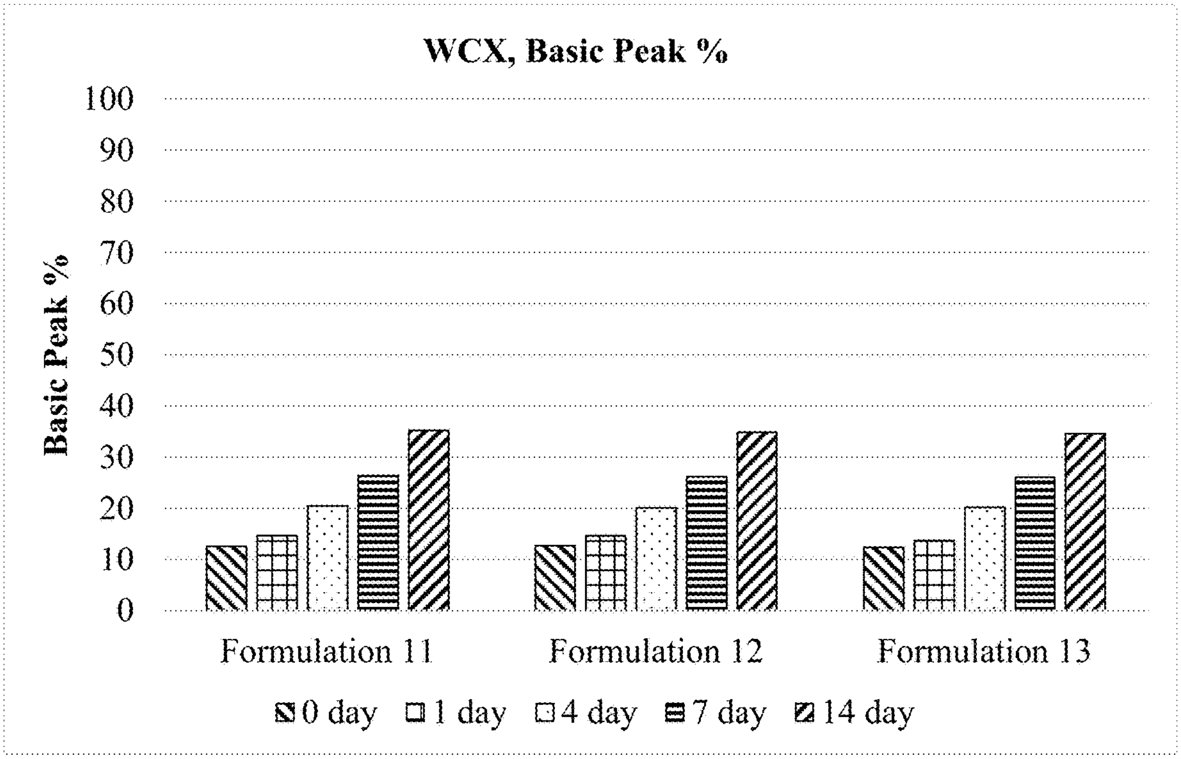
FIG. 12D illustrates changes (%) in relative contents of basic variants in Formulations 11 to 13 in a stability test under harsh conditions at 40° C.

When size-exclusion chromatography analysis was performed in a stability test under harsh conditions at 40° C. for 14 days, formulations 11 to 13 showed similar change patterns. The major changes were increases in high-molecular-weight (HMW) and low-molecular-weight (LMW) degradation products and a decrease in monomer content (about less than 1.0%), and there was no significant difference according to formulation. In conclusion, as a result of performing size-exclusion chromatography analysis in a stability test under harsh conditions at 40° C., there was no significant difference in stability profile between the formulations according to the concentration (0 to 0.04%) of polysorbate 80 (see FIG. 11).

Example 18. WCX Chromatography Analysis for Formulations Containing Trastuzumab and HP46

For WCX chromatography analysis, an HPLC system available from Shimadzu Prominence and as columns, a TSKgel CM-STAT column (4.6×100 mm, 7 μm), a TSKgel guard gel CMSTAT (3.2 mm i.d.×1.5 cm), and the like were used. Mobile phase A is 10 mM sodium phosphate (pH 7.5) and mobile phase B is 10 mM sodium phosphate (pH 7.2) containing 0.1 M NaCl. Analysis was carried out for 55 minutes with a linear concentration gradient of 0 to 30% mobile phase B at a flow rate of 0.8 mL/min. The sample was diluted with mobile phase A so that the final concentration was 1.0 mg/mL, 80 μL of the sample was injected into HPLC, and then absorbance of a column eluate at 280 nm was recorded. The monomer ratio of trastuzumab in the HPLC chromatogram was calculated and graphed.

Formulations 11 to 13 showed similar change patterns when WCX analysis was performed in a stability test under harsh conditions at 40° C. for 14 days. Specific changes include an increase in the relative content of acidic variants (approximately 10% change for 14 days), a decrease in the relative content of main peaks (approximately 40% change for 14 days), and an increase in the relative content of basic variants (approximately 300% change for 14 days), and there was no significant difference according to formulation. In conclusion, in the WCX analysis in a stability test under harsh conditions at 40° C., protein stability according to polysorbate 80 (0 to 0.04%) was similar (see FIGS. 12A-12D).

Example 19. Measurement of Enzymatic Activity for Formulations Containing Trastuzumab and HP46

Turbidimetric assay for measuring enzymatic activity is a method of measuring, by absorbance, the degree to which an aggregate is formed by binding of residual hyaluronic acid to acidified albumin (BSA), and when hyaluronic acid is hydrolyzed by PH20, the extent of binding to albumin is reduced, resulting in reduced absorbance. BTH (Sigma) as a standardized product was diluted to 1, 2, 5, 7.5, 10, 15, 20, 30, 50, and 60 units/mL and prepared in each tube. Purified protein samples were diluted with enzyme diluent buffer (20 mM Tris·HCl, PH 7.0, 77 mM NaCl, 0.01% (w/v) bovine serum albumin) to 100X, 300X, 600X, 1200X, and 2400X and prepared in each tube. In fresh tubes, the hyaluronic acid solution, having a concentration of 3 mg/mL, was diluted 10-fold to a concentration of 0.3 mg/mL so that the volume of each tube became 180 μL. 60 μL of the sample containing hyaluronidase was added to the diluted hyaluronic acid solution, mixed therewith, and allowed to react at 37° C. for 45 minutes. After the reaction was completed, 50 μL of the reacted enzyme and 250 μL of an acidic albumin solution were added to each well of a 96-well plate and shaken for 10 minutes, and then absorbance at 600 nm was measured using a spectrophotometer.

Figure 13:
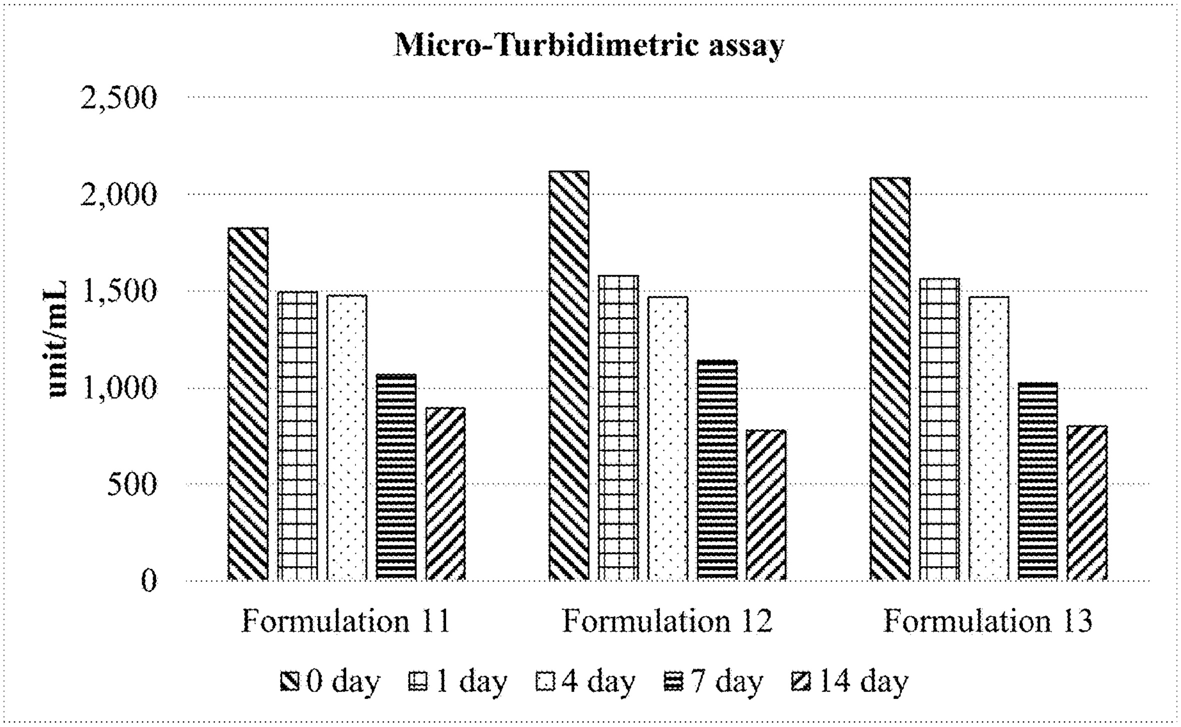
FIG. 13 illustrates changes (%) in relative enzymatic activity of formulations 11 to 13 in a stability test under harsh conditions at 40° C.

As a result of performing activity analysis in a stability test under harsh conditions at 40° C. for 14 days, it was found that the higher the concentration of polysorbate 80, the greater the reduction in activity over time (see FIG. 13).

Working Example 20. Formulation Development

Three types of rituximab formulations were prepared as described in Table 10. Formulations 14 to 16 commonly include 120 mg/mL of rituximab, 20 mM histidine/histidine-HCl (pH 5.5), 210 mM trehalose, 10 mM methionine, and a PH20 variant. The difference among formulations 14 to 16 is the concentration of a non-ionic surfactant, which includes: formulation 1:0% polysorbate 80, formulation 2:0.005% polysorbate 80, and formulation 3:0.06% polysorbate 80.

TABLE 10

| Composition of formulations | | | |
|---|---|---|---|
| | Formulation 14 | Formulation 15 | Formulation 16 |
| Rituximab | 120 mg/mL (±10) | | |
| PS 80 | 0% | 0.005% | 0.06% |
| Buffer | 20 mM histidine/histidine-HCl | | |
| Stabilizer 1 | 210 mM trehalose | | |
| Stabilizer 2 | 10 mM methionine | | |
| pH | 5.5 | | |
| Hyaluronidase | HP46 of SEQ ID NO: 44 (2,000 units/mL) | | |

Figure 14:
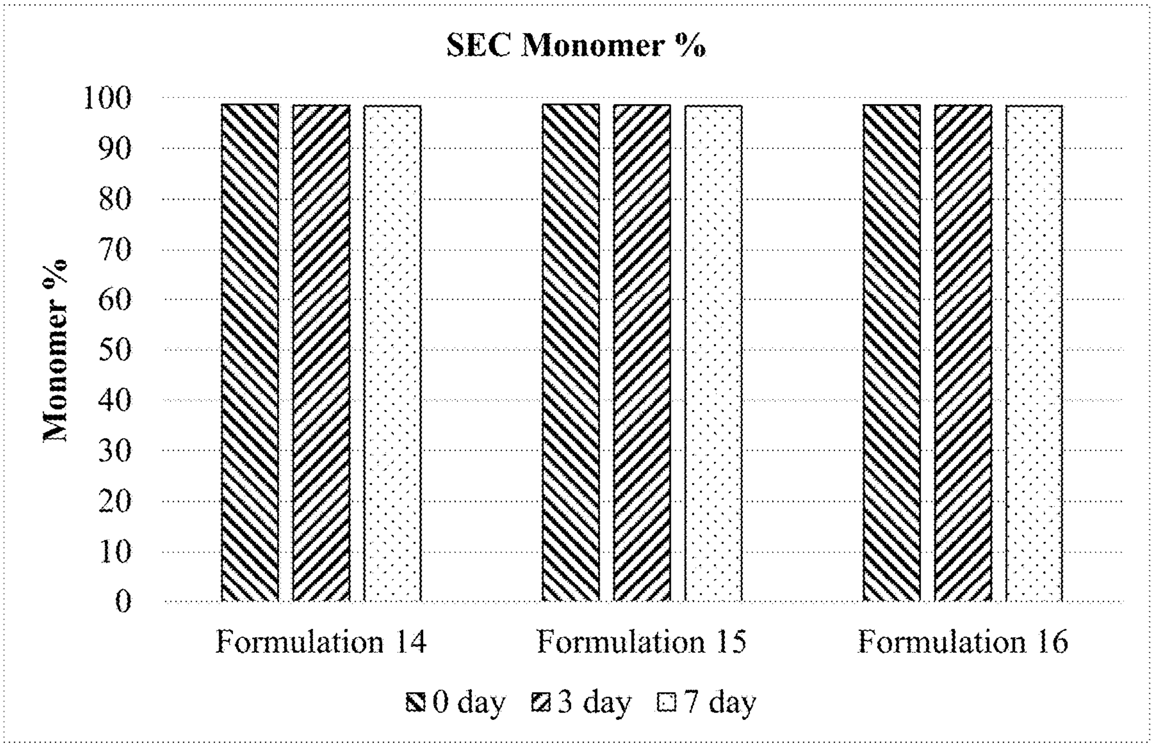
FIG. 14 illustrates changes in the purity of rituximab monomers of Formulations 14 to 16 in a stability test under harsh conditions at 40° C.

When size-exclusion chromatography analysis was performed in a stability test under harsh conditions at 40° C. for 7 days, formulations 14 to 16 showed similar change patterns. The major changes were increases in high-molecular-weight (HMW) and low-molecular-weight (LMW) degradation products and a decrease in monomer content (less than about 1.0%), and there was no significant difference according to formulation. In conclusion, as a result of performing size-exclusion chromatography analysis in a stability test under harsh conditions at 40° C., there was no significant difference in stability profile between the formulations according to the concentration (0 to 0.06%) of polysorbate 80 (see FIG. 14).

Working Example 21. Measurement of Enzymatic Activity for Formulations Containing Rituximab and HP46

Turbidimetric assay for measuring enzymatic activity is a method of measuring, by absorbance, the degree to which an aggregate is formed by binding of residual hyaluronic acid to acidified albumin (BSA), and when hyaluronic acid is hydrolyzed by PH20, the extent of binding to albumin is reduced, resulting in reduced absorbance. BTH (Sigma) as a standardized product was diluted to 1, 2, 5, 7.5, 10, 15, 20, 30, 50, and 60 units/mL and prepared in each tube. Purified protein samples were diluted with enzyme diluent buffer (20 mM Tris·HCl, pH 7.0, 77 mM NaCl, 0.01% (w/v) bovine serum albumin) to 100x, 300X, 600X, 1200X, and 2400X and prepared in each tube. In fresh tubes, the hyaluronic acid solution, having a concentration of 3 mg/ml, was diluted 10-fold to a concentration of 0.3 mg/mL so that the volume of each tube became 180 μL. 60 μL of the sample containing hyaluronidase was added to the diluted hyaluronic acid solution, mixed therewith, and allowed to react at 37° C. for 45 minutes. After the reaction was completed, 50 μL of the reacted enzyme and 250 μL of an acidic albumin solution were added to each well of a 96-well plate and shaken for 10 minutes, and then absorbance at 600 nm was measured using a spectrophotometer.

Figure 15:
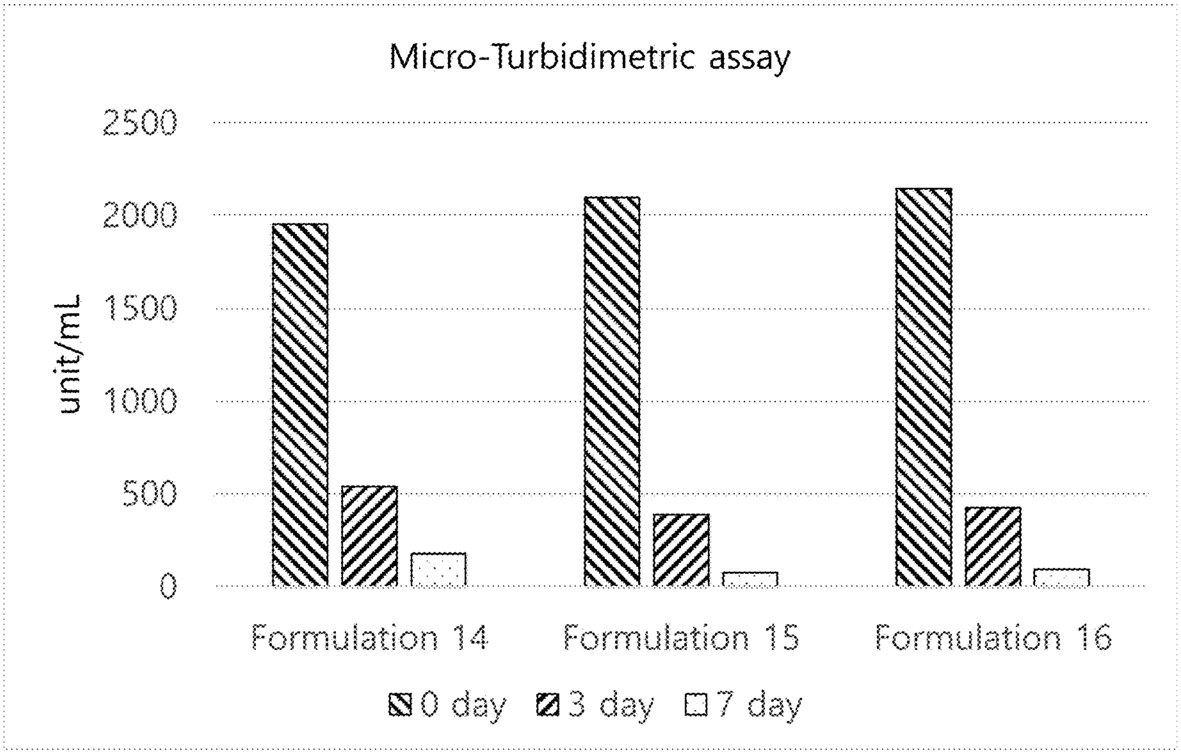
FIG. 15 illustrates changes in relative enzymatic activity of Formulations 14 to 16 in a stability test under harsh conditions at 40° C.

As a result of performing activity analysis in a stability test under harsh conditions at 40° C. for 7 days, it was found that the higher the concentration of polysorbate 80, the greater the reduction in activity over time (see FIG. 15).

Working Example 22. Measurement of Enzymatic Activity in Formulations of Commercially Available Products not Containing Polysorbate Two types of commercially available rituximab formulations were prepared as described in Table 11. Formulation 17 is a commercially available buffer for subcutaneous injection formulations, and formulation 18 is a commercially available buffer for intravenous injection formulations. Formulations 17 and 18 contain a PH20 variant and rituximab at 120 mg/mL and 100 mg/mL, respectively, but do not contain polysorbate 80 unlike formulations of commercially available products.

TABLE 11

| Composition of formulations | | |
|---|---|---|
| | Formulation 17 | Formulation 18 |
| Rituximab | 120 mg/mL | 100 mg/mL |
| Buffer | 20 mM histidine/histidine-HCl | 25 mM Sodium citrate |
| Stabilizer 1 | 210 mM trehalose | 145 mM NaCl |
| Stabilizer 2 | 10 mM methionine | 10 mM methionine |
| pH | 5.5 | 6.5 |
| Hyaluronidase | HP46 of SEQ ID NO: 44 (2,000 units/mL) | |

Turbidimetric assay for measuring enzymatic activity is a method of measuring, by absorbance, the degree to which an aggregate is formed by binding of residual hyaluronic acid to acidified albumin (BSA), and when hyaluronic acid is hydrolyzed by PH20, the extent of binding to albumin is reduced, resulting in reduced absorbance. BTH (Sigma) as a standardized product was diluted to 1, 2, 5, 7.5, 10, 15, 20, 30, 50, and 60 units/mL and prepared in each tube. Purified protein samples were diluted with enzyme diluent buffer (20 mM Tris·HCl, pH 7.0, 77 mM NaCl, 0.01% (w/v) bovine serum albumin) to 100X, 300X, 600X, 1200X, and 2400X and prepared in each tube. In fresh tubes, the hyaluronic acid solution, having a concentration of 3 mg/mL, was diluted 10-fold to a concentration of 0.3 mg/mL so that the volume of each tube became 180 μL. 60 μL of the sample containing hyaluronidase was added to the diluted hyaluronic acid solution, mixed therewith, and allowed to react at 37° C. for 45 minutes. After the reaction was completed, 50 μL of the reacted enzyme and 250 μL of an acidic albumin solution were added to each well of a 96-well plate and shaken for 10 minutes, and then absorbance at 600 nm was measured using a spectrophotometer.

Figure 16:
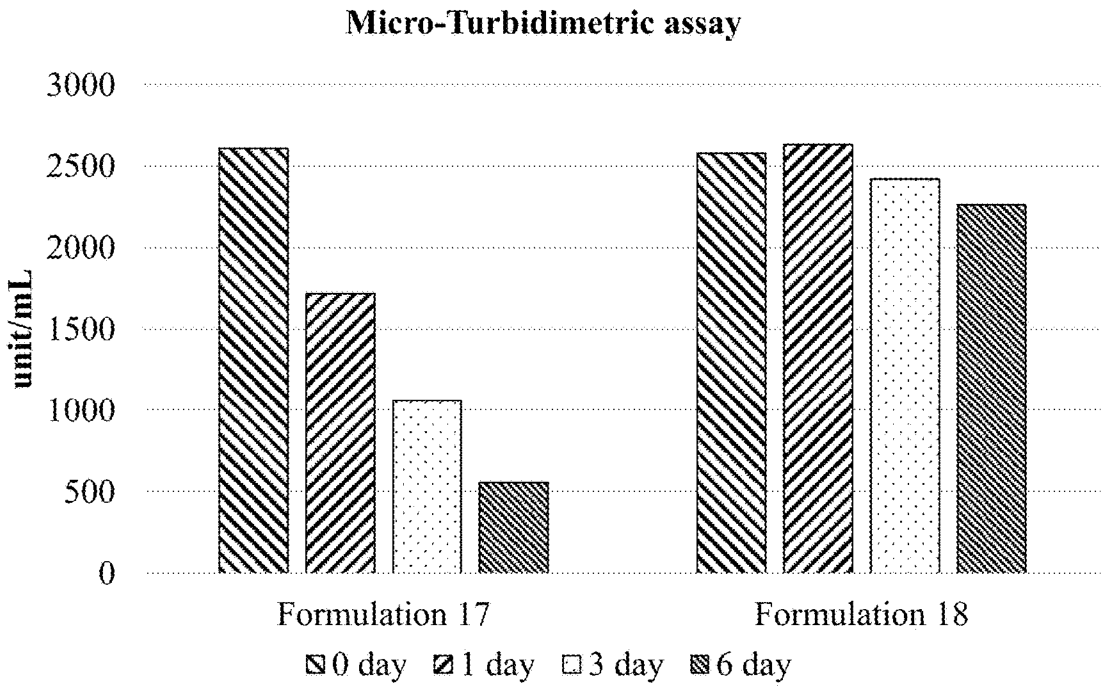
FIG. 16 illustrates changes in relative enzymatic activity of Formulations 17 and 18 in a stability test under harsh conditions at 40° C.

As a result of performing activity analysis in a stability test under harsh conditions at 40° C. for 6 days, it was found that high activity was maintained even in the formulations not containing polysorbate 80, and particularly, formulation 18 maintained high activity (see FIG. 16).

Working Example 23: Formulation Development

Four types of pembrolizumab subcutaneous injection formulations were prepared as described in Table 12. Formulations 19, 20, and 21 commonly include 25 mg/mL of pembrolizumab, 10 mM histidine (pH 5.5), 7% sucrose, 10 mM methionine, and a PH20 variant. The difference among formulations 19 to 21 is the concentration of a non-ionic surfactant: formulation 19:0% polysorbate 80, formulation 20:0.005% polysorbate 80, and formulation 21:0.02% polysorbate 80. Formulation 22 contains 25 mg/mL of pembrolizumab and consists of 10 mM histidine (pH 5.5), 210 mM trehalose, 10 mM methionine, 0.02% polysorbate 80, and a PH20 variant.

TABLE 12

Composition of formulations

| | Formulation 19 | Formulation 20 | Formulation 21 | Formulation 22 |
|---|---|---|---|---|
| Antibody | Pembrolizumab (25 mg/mL) | | | |
| Buffer | 10 mM histidine (pH 5.5) | | | |
| Stabilizer 1 | 7% sucrose | 7% sucrose | 7% sucrose | 210 mM trehalose |
| Stabilizer 2 | 10 mM methionine | 10 mM methionine | 10 mM methionine | 10 mM methionine |
| Polysorbate 80 | 0% | 0.005% | 0.02% | 0.02% |
| Hyaluronidase | HP46 of SEQ ID NO: 44 (2,000 units/mL) | | | |

Working Example 24. Measurement Using Spectrophotometer

Formulations 19, 20, 21, and 22 were left alone for 7 days at 40° C., and changes in protein concentration were analyzed using a spectrophotometer manufactured by Beckman. Each sample was diluted with distilled water so that the concentration of the sample was 0.4 mg/mL, and then absorbance of the protein at 280 nm was measured using a spectrophotometer.

In a stability test under harsh conditions at 40° C. for 7 days, there was no significant difference in protein concentrations of formulations 19 to 22.

Working Example 25. Investigation of Monomer Ratio of Pembrolizumab in Each Formulation Using Size-Exclusion Chromatography For size-exclusion chromatography analysis, an HPLC system available from Shimadzu Prominence and as columns, a TSK-gel G3000SWXL (7.8×300 mm, 5 μm) and a TSK guard column (6.0×4.0 mm, 7 μm) were used. As a mobile phase, 0.2 M potassium phosphate (pH 6.2) containing 0.25 M potassium chloride was used. Analysis was performed for 35 minutes by applying an isocratic separation mode at a flow rate of 0.5 mL/min. The sample was diluted with an analytical solvent so that the final concentration was 10 mg/mL, and after injecting 20 μL of the sample into the HPLC column, absorbance of the column eluate at 280 nm was measured. The monomer ratio of pembrolizumab in the HPLC chromatogram was calculated and graphed.

Figure 17:
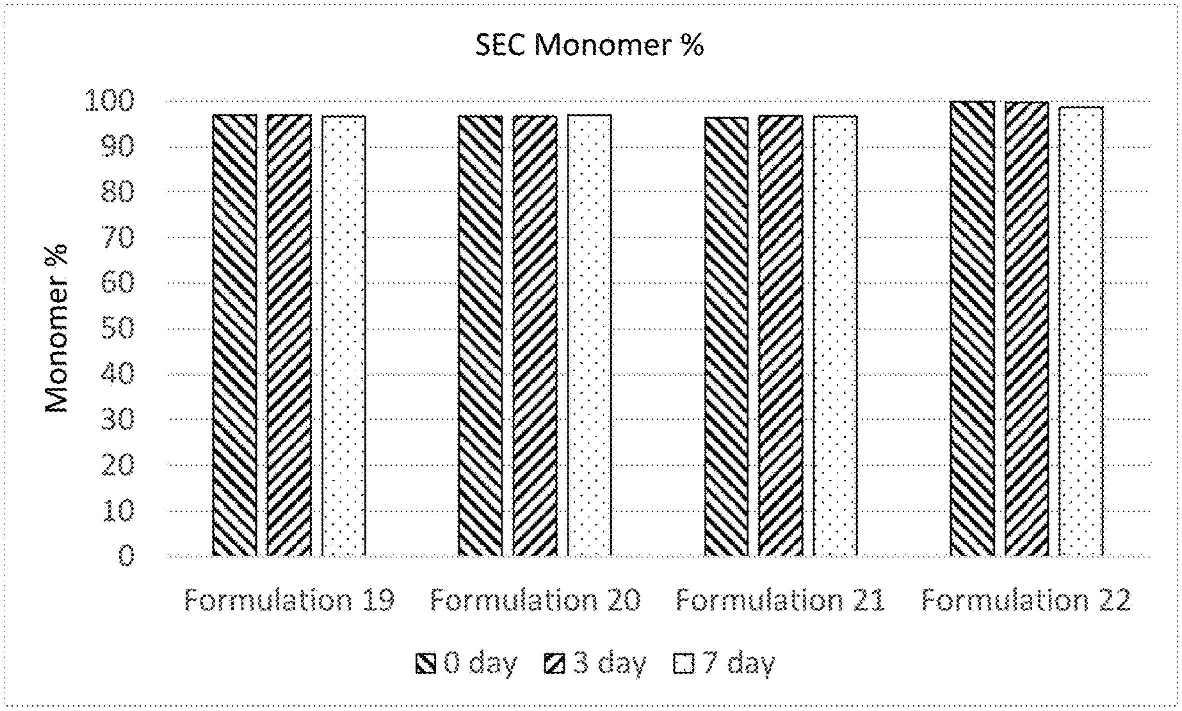
FIG. 17 illustrates size-exclusion chromatography analysis results of Formulations 19 to 22 at 40° C.

When size-exclusion chromatography analysis was performed in a stability test under harsh conditions at 40° C. for 7 days, formulations 19, 20, 21, and 22 showed similar change patterns. There was no significant difference according to formulation in the change patterns of high-molecular-weight (HMW) and low-molecular-weight (LMW) degradation products. In conclusion, as a result of performing size-exclusion chromatography analysis in a stability test under harsh conditions at 40° C., formulations 19, 20, 21, and 22 did not show any significant difference, and there was also no difference according to the type of sugar (see FIG. 17). These results were consistent with those of the cases of trastuzumab and rituximab according to the previous examples.

Working Example 26. Measurement of Enzymatic Activity for Formulations Containing Pembrolizumab and HP46

A turbidimetric assay for measuring enzymatic activity is a method of measuring, by absorbance, the extent to which an aggregate is formed by binding of residual hyaluronic acid to acidified albumin (BSA), and when hyaluronic acid is hydrolyzed by PH20, the extent of binding to albumin is reduced, resulting in reduced absorbance. BTH (Sigma) as a standardized product was diluted to 1 unit/mL, 2, 5, 7.5, 10, 15, 20, 30, 50, and 60 units/mL and prepared in each tube. Purified protein samples were diluted with enzyme diluent buffer (20 mM Tris·HCl, pH 7.0, 77 mM NaCl, 0.01% (w/v) bovine serum albumin) to 100X, 300X, 600X, 1200X, and 2400X and prepared in each tube. In fresh tubes, the hyaluronic acid solution, having a concentration of 3 mg/mL, was diluted 10-fold to a concentration of 0.3 mg/mL so that the volume of each tube became 180 μL. 60 μL of the enzyme was added to the diluted hyaluronic acid solution, mixed therewith, and allowed to react at 37° C. for 45 minutes. After the reaction was completed, 50 μL of the reacted enzyme and 250 μL of an acidic albumin solution were added to each well of a 96-well plate and shaken for 10 minutes, and then absorbance at 600 nm was measured using a spectrophotometer.

Figure 18:
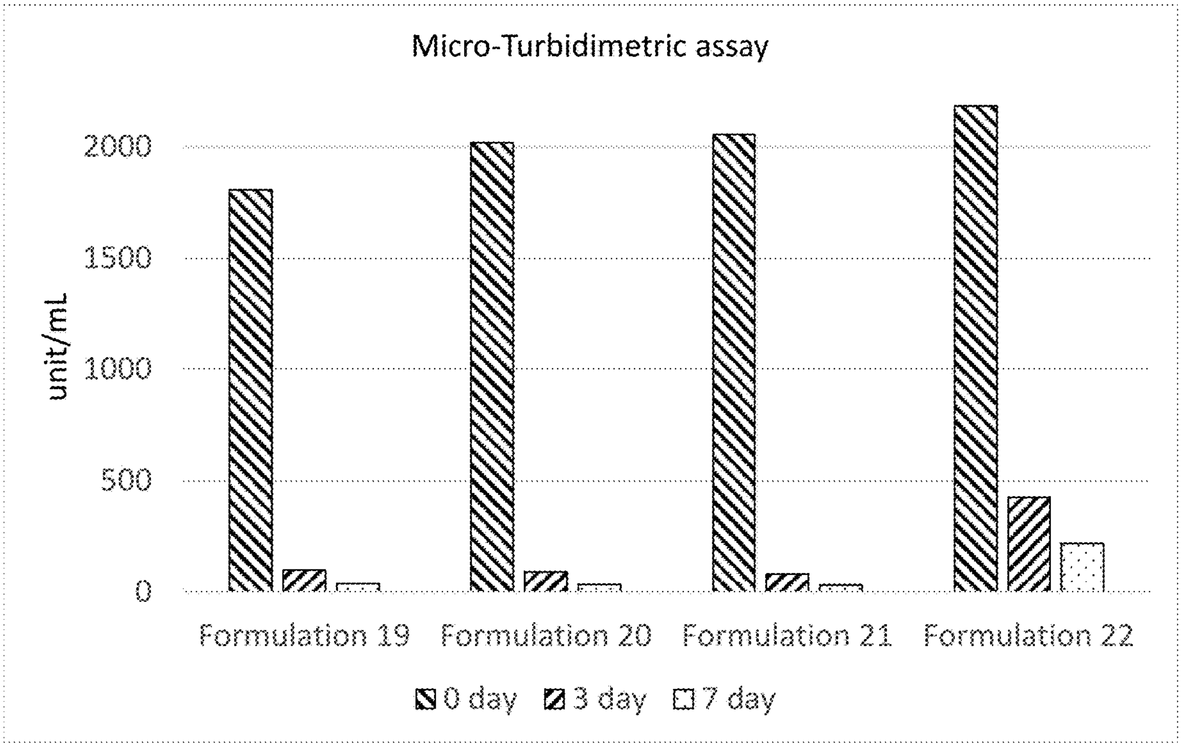
FIG. 18 illustrates changes in relative enzymatic activity of Formulations 19 to 22 in a stability test under harsh conditions at 40° C.

As a result of performing activity analysis in a stability test under harsh conditions at 40° C. for 7 days, it was found that the higher the concentration of polysorbate 80 is, the reduction in activity over time was somewhat large. It was also found that, when the same amount of polysorbate 80 was included, the reduction in activity was smaller in a trehalose-containing formulation than in a sucrose-containing formulation (see FIG. 18).

Working Example 27. pH-Activity Profiles of HP46 and Wild-Type HW2

For an experiment for determining the pH-activity profiles of HP46 and wild-type HW2, a microturbidimetric assay method was used. A hyaluronic acid buffer for dissolving hyaluronic acid as a substrate and an enzyme buffer for diluting the enzyme were prepared for each pH.

A total of three 96-well plates were prepared for a reaction between the enzyme and the substrate and designated as A, B, and C, and an experiment was carried out.

A hyaluronic acid buffer at a pH level of 4.0, 4.5, or 5.0 was prepared using 20 mM acetic acid and 70 mM NaCl, and a hyaluronic acid buffer at a pH level of 5.5, 6.0, 6.5, 7.0, or 8.0 was prepared using 20 mM sodium phosphate and 70 mM NaCl. 20 mg of hyaluronic acid was dissolved in 10 mL of each of the prepared hyaluronic acid buffers to prepare a final hyaluronic acid substrate solution, which was then diluted with each hyaluronic acid buffer prepared according to pH to prepare 500 μL of the resultant solution to a concentration of 0.1 mg/mL, 0.25 mg/mL, 0.45 mg/mL, or 0.7 mg/mL, and 100 μL of each solution was dispensed into each well of the 96-well plate designated as A. The hyaluronic acid buffers, diluted and prepared according to concentration, were used as calibration curves for measuring the concentration of hyaluronic acid.

An enzyme buffer at a pH level of 4.0, 4.5, or 5.0 was prepared using 20 mM acetic acid, 0.01% (w/v) BSA, and 70 mM NaCl, and an enzyme buffer at a pH level of 5.5, 6.0, 6.5, 7.0, or 8.0 was prepared using 20 mM sodium phosphate, 0.01% (w/v) BSA, and 70 mM NaCl.

HP46 and wild-type HW2 enzymes were diluted with the enzyme buffer prepared according to pH to 10 units/mL, and 50 μL of the resultant solution was dispensed into each well of the 96-well plate designated as B.

Figure 19:
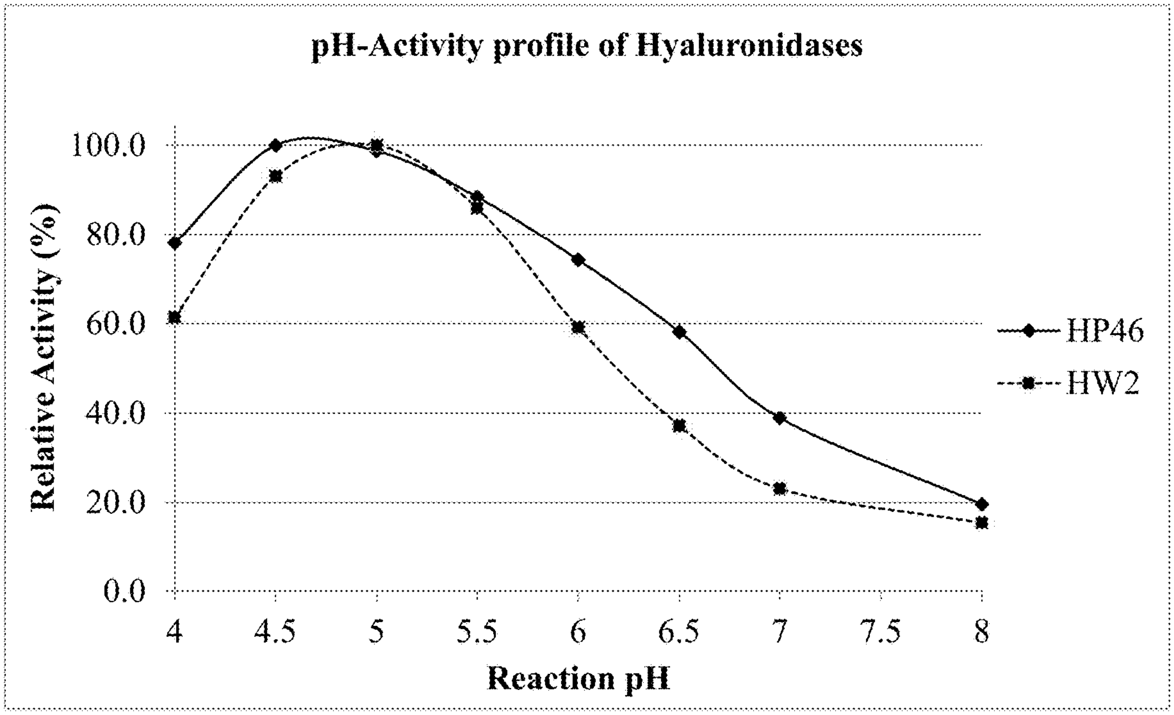
FIG. 19 illustrates changes in enzymatic activity according to changes in pH for recombinant human PH20 and HP46.

50 μL of the sample was transferred from each well of the 96-well plate designated as A to each well of the 96-well plate designated as B, followed by allowing a reaction to occur in a 37° C. shaking incubator for 45 minutes. 15 minutes before the reaction was completed, 200 μL of an acidic albumin solution was dispensed into each well of the 96-well plate designated as C and prepared, and when the enzymatic substrate reaction was completed, 40 μL of the sample was transferred from each well of the 96-well plate designated as B to each well of the 96-well plate designated as C, followed by allowing a reaction to occur for 20 minutes. After 20 minutes, absorbance at 600 nm was measured, and the amount of hyaluronic acid remaining after the enzymatic substrate reaction was calculated, and the activity profiles of the enzymes according to pH were completed (see FIG. 19).

Figure 20:
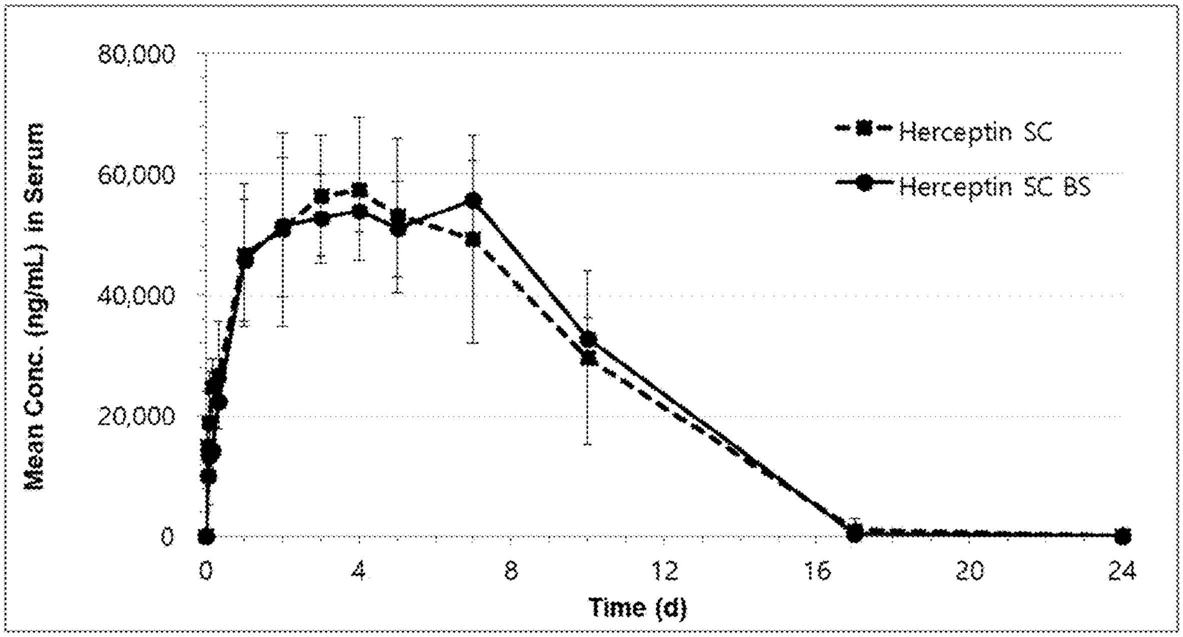
FIG. 20 illustrates experimental results of pharmacokinetics of a Herceptin subcutaneous injection product (Herceptin SC) and a Herceptin subcutaneous injection biosimilar candidate (trastuzumab+HP46; Herceptin SC BS) in 9-week-old Sprague-Dawley rats, wherein Herceptin and the Herceptin biosimilar candidate were injected at 18 mg/kg each, and the subcutaneous injection formulation contained 100 units of rHuPH20 and 100 units of HP46 (at pH 5.3).

Working Example 28. Test for Pharmacokinetics Using Herceptin Subcutaneous Injection Formulation and Trastuzumab and HP46 in Sprague-Dawley Rats To examine whether a subcutaneous injection formulation of trastuzumab and HP46 exhibits the same pharmacokinetic properties as those of a Herceptin subcutaneous injection formulation, an experiment was conducted using 9-week-old Sprague-Dawley rats. The dose of administered Herceptin and trastuzumab was 18 mg/kg of rat body weight, the amount of rHuPH20 included in the Herceptin subcutaneous injection formulation was 100 U, and the amount of HP46 was also 100 U. In the pharmacokinetic test, trastuzumab and HP46 showed the same Area Under the Curve (AUC) as that of the Herceptin subcutaneous injection formulation (see FIG. 20).

INDUSTRIAL APPLICABILITY

A pharmaceutical composition according to the present invention can be used for subcutaneous administration (subcutaneous injection) and is also very stable, and the activity of PH20 variants along with a drug, preferably an antibody drug or the like, can be maintained for a long time. Thus, the pharmaceutical composition can contribute to a reduction not only in the cost of producing subcutaneous injection formulations but also in medical costs, and is very advantageous in terms of convenience of patients.

REFERENCES

Bookbinder, L. H., Hofer, A., Haller, M. F., Zepeda, M. L., Keller, G. A., Lim, J. E., Edgington, T. S., Shepard, H. M., Patton, J. S., and Frost, G. I. (2006). A recombinant human enzyme for enhanced interstitial transport of therapeutics. J Control Release 114, 230-241.

Borders jr., C. L. and Raftery, A. (1968) Purification and Partial Characterization of Testicular Hyaluronidase. J Biol Chem 243, 3756-3762.

Chao, K. L., Muthukumar, L., and Herzberg, O. (2007). Structure of human hyaluronidase-1, a hyaluronan hydrolyzing enzyme involved in tumor growth and angiogenesis. Biochemistry 46, 6911-6920.

Chen, K. J., Sabrina, S., El-Safory, N. S., Lee, G. C., and Lee, C. K. (2016) Constitutive expression of recombinant human hyaluronidase PH20 by Pichia pastoris. J Biosci Bioeng. 122, 673-678.

Frost, G. I. (2007). Recombinant human hyaluronidase (rHuPH20): an enabling platform for subcutaneous drug and fluid administration. Expert Opin Drug Deliv 4, 427-440.

Hofinger, E. S., Bernhardt, G., and Buschauer, A. (2007) Kinetics of Hyal-1 and PH-20 hyaluronidases: comparison of minimal substrates and analysis of the transglycosylation reaction. Glycobiology 17, 963-971.

Kreidieh, F. Y., Moukadem, H. A., and Saghir, N.S.E. (2016) Overview, prevention and management of chemotherapy extravasation. World J Clin Oncol 7, 87-97.

Thomas, J. R., Yocum, R. C., Haller, M. F., and Flament J. (2009) The INFUSE-Morphine IIB Study: Use of Recombinant Human Hyaluronidase (rHuPH20) to Enhance the Absorption of Subcutaneous Morphine in Healthy Volunteers. J Pain Symptom Manag 38, 673-682.

What is claimed is:

1. A pharmaceutical composition comprising:
(a) ustekinumab;
(b) a PH20 variant,
wherein the amino acid sequence of the PH20 variant is SEQ ID NO: 1 with modifications consisting of:
(i) amino acid residue substitutions consisting of T341S, L342W, S343E, 1344N, M345T, S347T, M348K, K349E, L352Q, L353A, L354I, D355K, N356E, E359D, and I361T, relative to SEQ ID NO: 1;
(ii) an N-terminus deletion of amino acid residues M1 to T35, M1 to L36, M1 to N37, M1 to F38, M1 to R39, or M1 to A40 of SEQ ID NO: 1; and
(iii) a C-terminus deletion, wherein the C-terminus of the PH20 variant ends with an amino acid residue selected from any one of amino acid residues I465 to S490 of SEQ ID NO: 1; and
(c) one or more pharmaceutically acceptable additives.

2. The pharmaceutical composition of claim 1, wherein the one or more pharmaceutically acceptable additives is or are a buffer, and optionally a stabilizer and/or a surfactant.

3. The pharmaceutical composition according to claim 2, wherein the buffer is one or more selected from the group consisting of malate, formate, citrate, acetate, propionate, pyridine, piperazine, cacodylate, succinate, 2-(N-morpholino) ethanesulfonic acid (MES), histidine, Tris, bis-Tris, phosphate, ethanolamine, carbonate, piperazine-N,N'-bis(2-ethanesulfonic acid) (PIPES), imidazole, BIS-TRIS propane, N,N-bis(2-hydroxyethyl)-2-aminoethanesulfonic acid (BES), 3-(N-morpholino) propane sulfonic acid (MOPS), hydroxyethyl piperazine ethane sulfonic acid (HEPES), pyrophosphate, and triethanolamine.

4. The pharmaceutical composition according to claim 2, wherein the buffer is at a concentration of 0.001 mM to 200 mM, or the buffer is at pH 4 to 8.0.

5. The pharmaceutical composition according to claim 1, wherein the one or more pharmaceutically acceptable additives are a buffer, a stabilizer, and a surfactant, and wherein the stabilizer is one or more selected from the group consisting of a carbohydrate, a sugar, a sugar alcohol, and an amino acid.

6. The pharmaceutical composition according to claim 5, wherein the stabilizer is one or more of trehalose or hydrates thereof, sucrose, saccharin, glycerol, erythritol, threitol, xylitol, arabitol, ribitol, mannitol, sorbitol, galactitol, fucitol, iditol, inositol, volemitol, isomalt, maltitol, polyglycitol, cyclodextrin, hydroxylpropyl cyclodextrin, glucose, glutamine, glutamic acid, glycine, lysine, lysilysine, leucine, methionine, valine, serine, selenomethionine, citrulline, arginine, asparagine, aspartic acid, ornithine, isoleucine, taurine, theanine, threonine, tryptophan, tyrosine, phenylalanine, proline, pyrrolysine, histidine, or alanine.

7. The pharmaceutical composition according to claim 5, wherein the sugar or sugar alcohol is at a concentration of 0.001 mM to 500 mM, or
the amino acid is at a concentration of 1 mM to 100 mM.

8. The pharmaceutical composition according to claim 1, wherein the one or more pharmaceutically acceptable additives are a buffer, a stabilizer, and a surfactant, and wherein the surfactant is a non-ionic surfactant.

9. The pharmaceutical composition according to claim 8, wherein the non-ionic surfactant is one or more of polyoxyethylene-sorbitan fatty acid ester (polysorbate), polyethylene-polypropylene glycol, polyoxyethylenestearate, polyoxyethylene alkyl ethers, alkylphenyl polyoxyethylene ether, a polyoxyethylene-polyoxypropylene copolymer, or sodium dodecyl sulfate (SDS).

10. The pharmaceutical composition according to claim 8, wherein the surfactant is at a concentration of 0.0000001% (w/v) to 0.5% (w/v).

11. The pharmaceutical composition according to claim 1, wherein the ustekinumab is at a concentration of 50-350 mg/mL.

12. The pharmaceutical composition according to claim 1, wherein the PH20 variant is at a concentration of 100 units/mL to 20,000 units/mL.

13. The pharmaceutical composition according to claim 1, wherein
(a) the ustekinumab is at a concentration of 50-350 mg/mL;
(b) the PH20 variant is at 100 units/mL to 20,000 units/mL; and
(c) the one or more pharmaceutically acceptable additives are a buffer, a stabilizer, and a surfactant, wherein the buffer is at a concentration of 0.001 mM to 200 mM, the stabilizer is at a concentration of 0.001 mM to 500 mM, and the surfactant is at a concentration of 0.0000001% (w/v) to 0.5% (w/v).

14. The pharmaceutical composition according to claim 1, wherein
(a) the ustekinumab is at a concentration of 50-350 mg/mL;

(b) the PH20 variant is at 100 units/mL to 20,000 units/mL; and (c) the one or more pharmaceutically acceptable additives are a histidine buffer, a sugar that is trehalose or sucrose, methionine, and a polysorbate, wherein the histidine buffer is at pH of 5.5±2.0, the trehalose or sucrose is at a concentration of 0.001 mM to 500 mM, the methionine is at a concentration of 1 mM to 100 mM, and the polysorbate is at a concentration of 0.0000001% (w/v) to 0.5% (w/v).

15. The pharmaceutical composition according to claim 1, wherein the N-terminus deletion is a deletion of amino acid residues M1 to T35, M1 to L36, M1 to N37, or M1 to F38 of SEQ ID NO: 1.

16. The pharmaceutical composition according to claim 1, wherein the C-terminus of the PH20 variant ends with amino acid residue 1465, D466, A467, F468, K470, P471, P472, M473, E474, T475, E476, P478, 1480, Y482, A484, P486, T488, or S490 of SEQ ID NO: 1.

17. The pharmaceutical composition according to claim 1, wherein the N-terminus deletion is a deletion of amino acid residues M1 to T35, M1 to L36, M1 to N37, or M1 to F38, and the C-terminus of the PH20 variant ends with amino acid residue I465, F468, or P471 of SEQ ID NO: 1.

18. The pharmaceutical composition according to claim 1, wherein the N-terminus deletion is a deletion of amino acid residues M1 to T35, M1 to L36, M1 to N37, or M1 to F38, and the C-terminus of the PH20 variant ends with amino acid residue F468 of SEQ ID NO: 1.

19. The pharmaceutical composition according to claim 1, which is in a formulation for subcutaneous administration.

20. The pharmaceutical composition according to claim 1, wherein the one or more pharmaceutically acceptable additives are:

(i) a buffer at pH 4 to 8.3, wherein the buffer is one or more of any one of histidine, citrate, succinate, Tris, bis-Tris, or phosphate;

(ii) a stabilizer, wherein the stabilizer comprises one or more of any one of trehalose, sucrose, saccharin, glycerol, xylitol, arabitol, ribitol, mannitol, sorbitol, galactitol, fucitol, iditol, inositol, volemitol, maltitol, polyglycitol, cyclodextrin, hydroxylpropyl cyclodextrin, glucose, glutamine, glutamic acid, glycine, lysine, lysilysine, leucine, methionine, valine, serine, citrulline, arginine, asparagine, aspartic acid, tryptophan, proline, or histidine; and (iii) a surfactant, wherein the surfactant is one or more of any of polyoxyethylene-sorbitan fatty acid ester (polysorbate), polysorbate 20, polysorbate 80, alkylphenyl polyoxyethylene ether, or polyoxyethylene-polyoxypropylene copolymer.

21. The pharmaceutical composition according to claim 1, wherein the one or more pharmaceutically acceptable additives are:

(i) a buffer at pH 4 to 8.3, wherein the buffer is one or more of any one of histidine, citrate, succinate, 2-(N-morpholino) ethanesulfonic acid (MES), Tris, bis-Tris, phosphate, ethanolamine, carbonate, piperazine-N,N'-bis(2-ethanesulfonic acid) (PIPES), imidazole, BIS-TRIS propane, N,N-bis(2-hydroxyethyl)-2-aminoethanesulfonic acid (BES), 3-(N-morpholino) propane sulfonic acid (MOPS), hydroxyethyl piperazine ethane sulfonic acid (HEPES), or pyrophosphate;

(ii) a stabilizer, wherein the stabilizer comprises one or more of any one of trehalose, sucrose, saccharin, glycerol, xylitol, arabitol, ribitol, mannitol, sorbitol, galactitol, fucitol, iditol, inositol, volemitol, maltitol, polyglycitol, cyclodextrin, hydroxylpropyl cyclodextrin, glucose, glutamine, glutamic acid, glycine, lysine, lysilysine, leucine, methionine, valine, serine, citrulline, arginine, asparagine, aspartic acid, tryptophan, proline, or histidine; and (iii) a surfactant, wherein the surfactant is one or more of any of polyoxyethylene-sorbitan fatty acid ester (polysorbate), polysorbate 20, polysorbate 80, alkylphenyl polyoxyethylene ether, or polyoxyethylene-polyoxypropylene copolymer.

22. A method of treating an autoimmune disease in a human patient in need thereof comprising: administering an effective amount of the pharmaceutical composition of claim 1 to the patient.

23. The method of claim 22, wherein the autoimmune disease is rheumatoid arthritis, asthma, psoriasis, multiple sclerosis, allergic rhinitis, Crohn's disease, ulcerative colitis, systemic erythematous lupus, type I diabetes, inflammatory bowel disease (IBD), or atopic dermatitis.

24. The method of claim 22, wherein the pharmaceutical composition is administered by subcutaneous administration.

25. A composition comprising:

(a) ustekinumab; and (b) a PH20 variant, wherein the amino acid sequence of the PH20 variant is SEQ ID NO: 1 with modifications consisting of:

(i) amino acid residue substitutions consisting of T341S, L342W, S343E, 1344N, M345T, S347T, M348K, K349E, L352Q, L353A, L354I, D355K, N356E, E359D, and I361T, relative to SEQ ID NO: 1;

(ii) an N-terminus deletion of amino acid residues M1 to T35, M1 to L36, M1 to N37, M1 to F38, M1 to R39, or M1 to A40 of SEQ ID NO: 1; and (iii) a C-terminus deletion, wherein the C-terminus of the PH20 variant ends with an amino acid residue selected from any one of amino acid residues 1465 to S490 of SEQ ID NO: 1.

26. A pharmaceutical composition comprising:

(a) ustekinumab;

(b) a PH20 variant, wherein the amino acid sequence of the PH20 variant comprises the amino acid sequence of any one of the amino acid sequences of SEQ ID NOs: 5, 8, 9, 10, 11, 12, 13, 14, 16, 17, 18, 19, 22, 23, 24, 25, 27, 32, 33, 34, 35, 36, 37, 38, 39, 40, 41, 42, 43, 44, 45, 46, 47, 48, 49, or 50; and (c) one or more pharmaceutically acceptable additives.

27. The pharmaceutical composition according to claim 26, wherein the amino acid sequence of the PH20 variant comprises the amino acid sequence of SEQ ID NO: 44.

28. A pharmaceutical composition comprising:

(a) ustekinumab;

(b) a PH20 variant, wherein the amino acid sequence of the PH20 variant consists of the amino acid sequence of any one of the amino acid sequences of SEQ ID NOs: 5, 8, 9, 10, 11, 12, 13, 14, 16, 17, 18, 19, 22, 23, 24, 25, 27, 32, 33, 34, 35, 36, 37, 38, 39, 40, 41, 42, 43, 44, 45, 46, 47, 48, 49, or 50.

29. The pharmaceutical composition according to claim 28, wherein the amino acid sequence of the PH20 variant consists of the amino acid sequence of SEQ ID NO: 44.

30. A composition comprising:
(a) ustekinumab; and
(b) a PH20 variant, wherein the amino acid sequence of the PH20 variant consists of the amino acid sequence of SEQ ID NO: 44.

31. A composition comprising:
(a) ustekinumab; and
(b) a PH20 variant comprising the amino acid sequence of SEQ ID NO: 44.

* * * * *

SEQUENCE LISTING

```
<160> NUMBER OF SEQ ID NOS: 53

<210> SEQ ID NO 1
<211> LENGTH: 509
<212> TYPE: PRT
<213> ORGANISM: Artificial Sequence
<220> FEATURE:
<223> OTHER INFORMATION: Synthetic Construct

<400> SEQUENCE: 1

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
```

-continued

```
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
    290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
    370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Glu Pro Gln Ile
465                 470                 475                 480

Phe Tyr Asn Ala Ser Pro Ser Thr Leu Ser Ala Thr Met Phe Ile Val
                485                 490                 495
```

```
Ser Ile Leu Phe Leu Ile Ile Ser Ser Val Ala Ser Leu
            500                 505


<210> SEQ ID NO 2
<211> LENGTH: 26
<212> TYPE: PRT
<213> ORGANISM: Artificial Sequence
<220> FEATURE:
<223> OTHER INFORMATION: Synthetic Construct

<400> SEQUENCE: 2

Met Ala Thr Gly Ser Arg Thr Ser Leu Leu Leu Ala Phe Gly Leu Leu
1               5                   10                  15

Cys Leu Pro Trp Leu Gln Glu Gly Ser Ala
            20                  25


<210> SEQ ID NO 3
<211> LENGTH: 18
<212> TYPE: PRT
<213> ORGANISM: Artificial Sequence
<220> FEATURE:
<223> OTHER INFORMATION: Synthetic Construct

<400> SEQUENCE: 3

Met Lys Trp Val Thr Phe Ile Ser Leu Leu Phe Leu Phe Ser Ser Ala
1               5                   10                  15

Tyr Ser


<210> SEQ ID NO 4
<211> LENGTH: 21
<212> TYPE: PRT
<213> ORGANISM: Artificial Sequence
<220> FEATURE:
<223> OTHER INFORMATION: Synthetic Construct

<400> SEQUENCE: 4

Met Ala Ala His Leu Leu Pro Ile Cys Ala Leu Phe Leu Thr Leu Leu
1               5                   10                  15

Asp Met Ala Gln Gly
            20


<210> SEQ ID NO 5
<211> LENGTH: 455
<212> TYPE: PRT
<213> ORGANISM: Artificial Sequence
<220> FEATURE:
<223> OTHER INFORMATION: Synthetic Construct

<400> SEQUENCE: 5

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95
```

```
Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Thr Arg Thr Lys Glu Ser Cys Gln Ala Ile Lys
305                 310                 315                 320

Glu Tyr Met Asp Thr Thr Leu Gly Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

Ala Ser Pro Ser Thr Leu Ser
    450                 455
```

<210> SEQ ID NO 6
<211> LENGTH: 455
<212> TYPE: PRT
<213> ORGANISM: Artificial Sequence
<220> FEATURE:
<223> OTHER INFORMATION: Synthetic Construct

<400> SEQUENCE: 6

```
Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Thr Arg Thr Lys Glu Ser Cys Gln Ala Ile Lys
305                 310                 315                 320

Glu Tyr Met Asp Thr Thr Leu Asn Pro Phe Ile Leu Asn Val Thr Ser
                325                 330                 335

Gly Ala Leu Leu Cys Ser Gln Ala Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
```

```
            420                 425                 430

Phe Leu Lys Pro Pro Met Glu Thr Glu Glu Pro Gln Ile Phe Tyr Asn
        435                 440                 445

Ala Ser Pro Ser Thr Leu Ser
    450                 455


<210> SEQ ID NO 7
<211> LENGTH: 455
<212> TYPE: PRT
<213> ORGANISM: Artificial Sequence
<220> FEATURE:
<223> OTHER INFORMATION: Synthetic Construct

<400> SEQUENCE: 7

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Thr Arg Thr Lys Glu Ser Cys Gln Ala Ile Lys
305                 310                 315                 320

Glu Tyr Met Asp Thr Thr Leu Gly Pro Phe Ile Leu Asn Val Thr Ser
```

```
                325                 330                 335

Gly Ala Leu Leu Cys Ser Gln Ala Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

Ala Ser Pro Ser Thr Leu Ser
    450                 455


<210> SEQ ID NO 8
<211> LENGTH: 455
<212> TYPE: PRT
<213> ORGANISM: Artificial Sequence
<220> FEATURE:
<223> OTHER INFORMATION: Synthetic Construct

<400> SEQUENCE: 8

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
```

```
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Val Ser Trp Glu Asn Thr Arg Thr Lys Glu Ser Cys Gln Ala Ile Lys
305                 310                 315                 320

Glu Tyr Met Asp Thr Thr Leu Gly Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

Ala Ser Pro Ser Thr Leu Ser
    450                 455


<210> SEQ ID NO 9
<211> LENGTH: 455
<212> TYPE: PRT
<213> ORGANISM: Artificial Sequence
<220> FEATURE:
<223> OTHER INFORMATION: Synthetic Construct

<400> SEQUENCE: 9

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
```

```
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

Ala Ser Pro Ser Thr Leu Ser
    450                 455


<210> SEQ ID NO 10
<211> LENGTH: 455
<212> TYPE: PRT
<213> ORGANISM: Artificial Sequence
<220> FEATURE:
<223> OTHER INFORMATION: Synthetic Construct

<400> SEQUENCE: 10

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
```

```
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Val Ser Trp Glu Asn Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

Ala Ser Pro Ser Thr Leu Ser
    450                 455
```

<210> SEQ ID NO 11
<211> LENGTH: 455
<212> TYPE: PRT
<213> ORGANISM: Artificial Sequence
<220> FEATURE:
<223> OTHER INFORMATION: Synthetic Construct

<400> SEQUENCE: 11

```
Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Asn Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365
```

```
Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

Ala Ser Pro Ser Thr Leu Ser
    450                 455


<210> SEQ ID NO 12
<211> LENGTH: 455
<212> TYPE: PRT
<213> ORGANISM: Artificial Sequence
<220> FEATURE:
<223> OTHER INFORMATION: Synthetic Construct

<400> SEQUENCE: 12

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270
```

```
Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Glu Asn Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

Ala Ser Pro Ser Thr Leu Ser
    450                 455


<210> SEQ ID NO 13
<211> LENGTH: 455
<212> TYPE: PRT
<213> ORGANISM: Artificial Sequence
<220> FEATURE:
<223> OTHER INFORMATION: Synthetic Construct

<400> SEQUENCE: 13

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175
```

```
Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Trp Glu Asn Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

Ala Ser Pro Ser Thr Leu Ser
    450                 455


<210> SEQ ID NO 14
<211> LENGTH: 455
<212> TYPE: PRT
<213> ORGANISM: Artificial Sequence
<220> FEATURE:
<223> OTHER INFORMATION: Synthetic Construct

<400> SEQUENCE: 14

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80
```

```
Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Thr Arg Thr Lys Glu Ser Cys Gln Ala Ile Lys
305                 310                 315                 320

Glu Tyr Met Asp Thr Thr Leu Asn Pro Phe Ile Leu Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

Ala Ser Pro Ser Thr Leu Ser
    450                 455
```

<210> SEQ ID NO 15
<211> LENGTH: 455
<212> TYPE: PRT
<213> ORGANISM: Artificial Sequence
<220> FEATURE:

<223> OTHER INFORMATION: Synthetic Construct

<400> SEQUENCE: 15

Leu Asn Phe Arg Ala Pro Pro Val Ile Pro Asn Val Pro Phe Leu Trp
1 5 10 15

Ala Trp Asn Ala Pro Ser Glu Phe Cys Leu Gly Lys Phe Asp Glu Pro
20 25 30

Leu Asp Met Ser Leu Phe Ser Phe Ile Gly Ser Pro Arg Ile Asn Ala
35 40 45

Thr Gly Gln Gly Val Thr Ile Phe Tyr Val Asp Arg Leu Gly Tyr Tyr
50 55 60

Pro Tyr Ile Asp Ser Ile Thr Gly Val Thr Val Asn Gly Gly Ile Pro
65 70 75 80

Gln Lys Ile Ser Leu Gln Asp His Leu Asp Lys Ala Lys Lys Asp Ile
85 90 95

Thr Phe Tyr Met Pro Val Asp Asn Leu Gly Met Ala Val Ile Asp Trp
100 105 110

Glu Glu Trp Arg Pro Thr Trp Ala Arg Asn Trp Lys Pro Lys Asp Val
115 120 125

Tyr Lys Asn Arg Ser Ile Glu Leu Val Gln Gln Gln Asn Val Gln Leu
130 135 140

Ser Leu Thr Glu Ala Thr Glu Lys Ala Lys Gln Glu Phe Glu Lys Ala
145 150 155 160

Gly Lys Asp Phe Leu Val Glu Thr Ile Lys Leu Gly Lys Leu Leu Arg
165 170 175

Pro Asn His Leu Trp Gly Tyr Tyr Leu Phe Pro Asp Cys Tyr Asn His
180 185 190

His Tyr Lys Lys Pro Gly Tyr Asn Gly Ser Cys Phe Asn Val Glu Ile
195 200 205

Lys Arg Asn Asp Asp Leu Ser Trp Leu Trp Asn Glu Ser Thr Ala Leu
210 215 220

Tyr Pro Ser Ile Tyr Leu Asn Thr Gln Gln Ser Pro Val Ala Ala Thr
225 230 235 240

Leu Tyr Val Arg Asn Arg Val Arg Glu Ala Ile Arg Val Ser Lys Ile
245 250 255

Pro Asp Ala Lys Ser Pro Leu Pro Val Phe Ala Tyr Thr Arg Ile Val
260 265 270

Phe Thr Asp Gln Val Leu Lys Phe Leu Ser Gln Asp Glu Leu Val Tyr
275 280 285

Thr Phe Gly Glu Thr Val Ala Leu Gly Ala Ser Gly Ile Val Ile Trp
290 295 300

Gly Thr Leu Ser Ile Thr Arg Thr Lys Glu Ser Cys Gln Ala Ile Lys
305 310 315 320

Glu Tyr Met Asp Thr Thr Leu Asn Pro Phe Ile Leu Asn Val Thr Ser
325 330 335

Gly Ala Lys Met Cys Ser Gln Val Leu Cys Gln Glu Gln Gly Val Cys
340 345 350

Ile Arg Lys Asn Trp Asn Ser Ser Asp Tyr Leu His Leu Asn Pro Asp
355 360 365

Asn Phe Ala Ile Gln Leu Glu Lys Gly Gly Lys Phe Thr Val Arg Gly
370 375 380

Lys Pro Thr Leu Glu Asp Leu Glu Gln Phe Ser Glu Lys Phe Tyr Cys
385 390 395 400

```
Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

Ala Ser Pro Ser Thr Leu Ser
    450                 455


<210> SEQ ID NO 16
<211> LENGTH: 453
<212> TYPE: PRT
<213> ORGANISM: Artificial Sequence
<220> FEATURE:
<223> OTHER INFORMATION: Synthetic Construct

<400> SEQUENCE: 16

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Thr
    290                 295                 300
```

```
Leu Ser Ile Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe Leu
            420                 425                 430

Lys Pro Pro Met Glu Thr Glu Glu Pro Gln Ile Phe Tyr Asn Ala Ser
        435                 440                 445

Pro Ser Thr Leu Ser
    450


<210> SEQ ID NO 17
<211> LENGTH: 430
<212> TYPE: PRT
<213> ORGANISM: Artificial Sequence
<220> FEATURE:
<223> OTHER INFORMATION: Synthetic Construct

<400> SEQUENCE: 17

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205
```

```
Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile
            420                 425                 430


<210> SEQ ID NO 18
<211> LENGTH: 433
<212> TYPE: PRT
<213> ORGANISM: Artificial Sequence
<220> FEATURE:
<223> OTHER INFORMATION: Synthetic Construct

<400> SEQUENCE: 18

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140
```

```
Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe


<210> SEQ ID NO 19
<211> LENGTH: 436
<212> TYPE: PRT
<213> ORGANISM: Artificial Sequence
<220> FEATURE:
<223> OTHER INFORMATION: Synthetic Construct

<400> SEQUENCE: 19

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
```

```
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro
        435
```

<210> SEQ ID NO 20
<211> LENGTH: 452
<212> TYPE: PRT
<213> ORGANISM: Artificial Sequence
<220> FEATURE:
<223> OTHER INFORMATION: Synthetic Construct

<400> SEQUENCE: 20

```
Phe Arg Gly Pro Leu Leu Pro Asn Arg Pro Phe Leu Trp Ala Trp Asn
1               5                   10                  15

Ala Pro Ser Glu Phe Cys Leu Gly Lys Phe Asp Glu Pro Leu Asp Met
            20                  25                  30

Ser Leu Phe Ser Phe Ile Gly Ser Pro Arg Ile Asn Ala Thr Gly Gln
        35                  40                  45

Gly Val Thr Ile Phe Tyr Val Asp Arg Leu Gly Tyr Tyr Pro Tyr Ile
    50                  55                  60

Asp Ser Ile Thr Gly Val Thr Val Asn Gly Gly Ile Pro Gln Lys Ile
65                  70                  75                  80

Ser Leu Gln Asp His Leu Asp Lys Ala Lys Lys Asp Ile Thr Phe Tyr
                85                  90                  95

Met Pro Val Asp Asn Leu Gly Met Ala Val Ile Asp Trp Glu Glu Trp
            100                 105                 110

Arg Pro Thr Trp Ala Arg Asn Trp Lys Pro Lys Asp Val Tyr Lys Asn
        115                 120                 125

Arg Ser Ile Glu Leu Val Gln Gln Gln Asn Val Gln Leu Ser Leu Thr
    130                 135                 140

Glu Ala Thr Glu Lys Ala Lys Gln Glu Phe Glu Lys Ala Gly Lys Asp
145                 150                 155                 160

Phe Leu Val Glu Thr Ile Lys Leu Gly Lys Leu Leu Arg Pro Asn His
                165                 170                 175

Leu Trp Gly Tyr Tyr Leu Phe Pro Asp Cys Tyr Asn His His Tyr Lys
            180                 185                 190

Lys Pro Gly Tyr Asn Gly Ser Cys Phe Asn Val Glu Ile Lys Arg Asn
        195                 200                 205

Asp Asp Leu Ser Trp Leu Trp Asn Glu Ser Thr Ala Leu Tyr Pro Ser
    210                 215                 220

Ile Tyr Leu Asn Thr Gln Gln Ser Pro Val Ala Ala Thr Leu Tyr Val
225                 230                 235                 240

Arg Asn Arg Val Arg Glu Ala Ile Arg Val Ser Lys Ile Pro Asp Ala
                245                 250                 255

Lys Ser Pro Leu Pro Val Phe Ala Tyr Thr Arg Ile Val Phe Thr Asp
            260                 265                 270

Gln Val Leu Lys Phe Leu Ser Gln Asp Glu Leu Val Tyr Thr Phe Gly
        275                 280                 285

Glu Thr Val Ala Leu Gly Ala Ser Gly Ile Val Ile Trp Gly Thr Leu
    290                 295                 300

Ser Ile Thr Arg Thr Lys Glu Ser Cys Gln Ala Ile Lys Glu Tyr Met
305                 310                 315                 320

Asp Thr Thr Leu Asn Pro Tyr Ile Ile Asn Val Thr Leu Ala Ala Lys
                325                 330                 335

Met Cys Ser Gln Val Leu Cys Gln Glu Gln Gly Val Cys Ile Arg Lys
            340                 345                 350

Asn Trp Asn Ser Ser Asp Tyr Leu His Leu Asn Pro Asp Asn Phe Ala
        355                 360                 365

Ile Gln Leu Glu Lys Gly Gly Lys Phe Thr Val Arg Gly Lys Pro Thr
    370                 375                 380

Leu Glu Asp Leu Glu Gln Phe Ser Glu Lys Phe Tyr Cys Ser Cys Tyr
385                 390                 395                 400

Ser Thr Leu Ser Cys Lys Glu Lys Ala Asp Val Lys Asp Thr Asp Ala
                405                 410                 415
```

```
Val Asp Val Cys Ile Ala Asp Gly Val Cys Ile Asp Ala Phe Leu Lys
            420                 425                 430

Pro Pro Met Glu Thr Glu Glu Pro Gln Ile Phe Tyr Asn Ala Ser Pro
        435                 440                 445

Ser Thr Leu Ser
    450


<210> SEQ ID NO 21
<211> LENGTH: 452
<212> TYPE: PRT
<213> ORGANISM: Artificial Sequence
<220> FEATURE:
<223> OTHER INFORMATION: Synthetic Construct

<400> SEQUENCE: 21

Phe Arg Gly Pro Leu Leu Pro Asn Arg Pro Phe Thr Thr Val Trp Asn
1               5                   10                  15

Ala Pro Ser Glu Phe Cys Leu Gly Lys Phe Asp Glu Pro Leu Asp Met
            20                  25                  30

Ser Leu Phe Ser Phe Ile Gly Ser Pro Arg Ile Asn Ala Thr Gly Gln
        35                  40                  45

Gly Val Thr Ile Phe Tyr Val Asp Arg Leu Gly Tyr Tyr Pro Tyr Ile
    50                  55                  60

Asp Ser Ile Thr Gly Val Thr Val Asn Gly Gly Ile Pro Gln Lys Ile
65                  70                  75                  80

Ser Leu Gln Asp His Leu Asp Lys Ala Lys Lys Asp Ile Thr Phe Tyr
                85                  90                  95

Met Pro Val Asp Asn Leu Gly Met Ala Val Ile Asp Trp Glu Glu Trp
            100                 105                 110

Arg Pro Thr Trp Ala Arg Asn Trp Lys Pro Lys Asp Val Tyr Lys Asn
        115                 120                 125

Arg Ser Ile Glu Leu Val Gln Gln Gln Asn Val Gln Leu Ser Leu Thr
    130                 135                 140

Glu Ala Thr Glu Lys Ala Lys Gln Glu Phe Glu Lys Ala Gly Lys Asp
145                 150                 155                 160

Phe Leu Val Glu Thr Ile Lys Leu Gly Lys Leu Leu Arg Pro Asn His
                165                 170                 175

Leu Trp Gly Tyr Tyr Leu Phe Pro Asp Cys Tyr Asn His His Tyr Lys
            180                 185                 190

Lys Pro Gly Tyr Asn Gly Ser Cys Phe Asn Val Glu Ile Lys Arg Asn
        195                 200                 205

Asp Asp Leu Ser Trp Leu Trp Asn Glu Ser Thr Ala Leu Tyr Pro Ser
    210                 215                 220

Ile Tyr Leu Asn Thr Gln Gln Ser Pro Val Ala Ala Thr Leu Tyr Val
225                 230                 235                 240

Arg Asn Arg Val Arg Glu Ala Ile Arg Val Ser Lys Ile Pro Asp Ala
                245                 250                 255

Lys Ser Pro Leu Pro Val Phe Ala Tyr Thr Arg Ile Val Phe Thr Asp
            260                 265                 270

Gln Val Leu Lys Phe Leu Ser Gln Asp Glu Leu Val Tyr Thr Phe Gly
        275                 280                 285

Glu Thr Val Ala Leu Gly Ala Ser Gly Ile Val Ile Trp Gly Thr Leu
    290                 295                 300

Ser Ile Thr Arg Thr Lys Glu Ser Cys Gln Ala Ile Lys Glu Tyr Met
305                 310                 315                 320
```

Asp Thr Thr Leu Asn Pro Tyr Ile Ile Asn Val Thr Leu Ala Ala Lys
325 330 335

Met Cys Ser Gln Val Leu Cys Gln Glu Gln Gly Val Cys Ile Arg Lys
340 345 350

Asn Trp Asn Ser Ser Asp Tyr Leu His Leu Asn Pro Asp Asn Phe Ala
355 360 365

Ile Gln Leu Glu Lys Gly Gly Lys Phe Thr Val Arg Gly Lys Pro Thr
370 375 380

Leu Glu Asp Leu Glu Gln Phe Ser Glu Lys Phe Tyr Cys Ser Cys Tyr
385 390 395 400

Ser Thr Leu Ser Cys Lys Glu Lys Ala Asp Val Lys Asp Thr Asp Ala
405 410 415

Val Asp Val Cys Ile Ala Asp Gly Val Cys Ile Asp Ala Phe Leu Lys
420 425 430

Pro Pro Met Glu Thr Glu Glu Pro Gln Ile Phe Tyr Asn Ala Ser Pro
435 440 445

Ser Thr Leu Ser
450

<210> SEQ ID NO 22
<211> LENGTH: 433
<212> TYPE: PRT
<213> ORGANISM: Artificial Sequence
<220> FEATURE:
<223> OTHER INFORMATION: Synthetic Construct

<400> SEQUENCE: 22

Phe Arg Ala Pro Pro Val Ile Pro Asn Val Pro Phe Leu Trp Ala Trp
1 5 10 15

Asn Ala Pro Ser Glu Phe Cys Leu Gly Lys Phe Asp Glu Pro Leu Asp
20 25 30

Met Ser Leu Phe Ser Phe Ile Gly Ser Pro Arg Ile Asn Ala Thr Gly
35 40 45

Gln Gly Val Thr Ile Phe Tyr Val Asp Arg Leu Gly Tyr Tyr Pro Tyr
50 55 60

Ile Asp Ser Ile Thr Gly Val Thr Val Asn Gly Gly Ile Pro Gln Lys
65 70 75 80

Ile Ser Leu Gln Asp His Leu Asp Lys Ala Lys Lys Asp Ile Thr Phe
85 90 95

Tyr Met Pro Val Asp Asn Leu Gly Met Ala Val Ile Asp Trp Glu Glu
100 105 110

Trp Arg Pro Thr Trp Ala Arg Asn Trp Lys Pro Lys Asp Val Tyr Lys
115 120 125

Asn Arg Ser Ile Glu Leu Val Gln Gln Gln Asn Val Gln Leu Ser Leu
130 135 140

Thr Glu Ala Thr Glu Lys Ala Lys Gln Glu Phe Glu Lys Ala Gly Lys
145 150 155 160

Asp Phe Leu Val Glu Thr Ile Lys Leu Gly Lys Leu Leu Arg Pro Asn
165 170 175

His Leu Trp Gly Tyr Tyr Leu Phe Pro Asp Cys Tyr Asn His His Tyr
180 185 190

Lys Lys Pro Gly Tyr Asn Gly Ser Cys Phe Asn Val Glu Ile Lys Arg
195 200 205

Asn Asp Asp Leu Ser Trp Leu Trp Asn Glu Ser Thr Ala Leu Tyr Pro
210 215 220

```
Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Thr
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe Leu
            420                 425                 430

Lys
```

<210> SEQ ID NO 23
<211> LENGTH: 431
<212> TYPE: PRT
<213> ORGANISM: Artificial Sequence
<220> FEATURE:
<223> OTHER INFORMATION: Synthetic Construct

<400> SEQUENCE: 23

```
Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140
```

```
Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Thr
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe
            420                 425                 430
```

<210> SEQ ID NO 24
<211> LENGTH: 455
<212> TYPE: PRT
<213> ORGANISM: Artificial Sequence
<220> FEATURE:
<223> OTHER INFORMATION: Synthetic Construct

<400> SEQUENCE: 24

```
Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80
```

```
Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Ser Trp Glu Asn Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

Ala Ser Pro Ser Thr Leu Ser
    450                 455
```

<210> SEQ ID NO 25
<211> LENGTH: 451
<212> TYPE: PRT
<213> ORGANISM: Artificial Sequence
<220> FEATURE:
<223> OTHER INFORMATION: Synthetic Construct

<400> SEQUENCE: 25

```
Ala Pro Pro Val Ile Pro Asn Val Pro Phe Leu Trp Ala Trp Asn Ala
1               5                   10                  15

Pro Ser Glu Phe Cys Leu Gly Lys Phe Asp Glu Pro Leu Asp Met Ser
            20                  25                  30

Leu Phe Ser Phe Ile Gly Ser Pro Arg Ile Asn Ala Thr Gly Gln Gly
        35                  40                  45

Val Thr Ile Phe Tyr Val Asp Arg Leu Gly Tyr Tyr Pro Tyr Ile Asp
    50                  55                  60

Ser Ile Thr Gly Val Thr Val Asn Gly Gly Ile Pro Gln Lys Ile Ser
65                  70                  75                  80

Leu Gln Asp His Leu Asp Lys Ala Lys Lys Asp Ile Thr Phe Tyr Met
                85                  90                  95

Pro Val Asp Asn Leu Gly Met Ala Val Ile Asp Trp Glu Glu Trp Arg
            100                 105                 110

Pro Thr Trp Ala Arg Asn Trp Lys Pro Lys Asp Val Tyr Lys Asn Arg
        115                 120                 125

Ser Ile Glu Leu Val Gln Gln Gln Asn Val Gln Leu Ser Leu Thr Glu
    130                 135                 140

Ala Thr Glu Lys Ala Lys Gln Glu Phe Glu Lys Ala Gly Lys Asp Phe
145                 150                 155                 160

Leu Val Glu Thr Ile Lys Leu Gly Lys Leu Leu Arg Pro Asn His Leu
                165                 170                 175

Trp Gly Tyr Tyr Leu Phe Pro Asp Cys Tyr Asn His His Tyr Lys Lys
            180                 185                 190

Pro Gly Tyr Asn Gly Ser Cys Phe Asn Val Glu Ile Lys Arg Asn Asp
        195                 200                 205

Asp Leu Ser Trp Leu Trp Asn Glu Ser Thr Ala Leu Tyr Pro Ser Ile
    210                 215                 220

Tyr Leu Asn Thr Gln Gln Ser Pro Val Ala Ala Thr Leu Tyr Val Arg
225                 230                 235                 240

Asn Arg Val Arg Glu Ala Ile Arg Val Ser Lys Ile Pro Asp Ala Lys
                245                 250                 255

Ser Pro Leu Pro Val Phe Ala Tyr Thr Arg Ile Val Phe Thr Asp Gln
            260                 265                 270

Val Leu Lys Phe Leu Ser Gln Asp Glu Leu Val Tyr Thr Phe Gly Glu
        275                 280                 285

Thr Val Ala Leu Gly Ala Ser Gly Ile Val Ile Trp Gly Thr Leu Ser
    290                 295                 300

Ile Thr Arg Thr Lys Glu Ser Cys Gln Ala Ile Lys Glu Tyr Met Asp
305                 310                 315                 320

Thr Thr Leu Asn Pro Tyr Ile Ile Asn Val Thr Leu Ala Ala Lys Met
                325                 330                 335

Cys Ser Gln Val Leu Cys Gln Glu Gln Gly Val Cys Ile Arg Lys Asn
            340                 345                 350

Trp Asn Ser Ser Asp Tyr Leu His Leu Asn Pro Asp Asn Phe Ala Ile
        355                 360                 365

Gln Leu Glu Lys Gly Gly Lys Phe Thr Val Arg Gly Lys Pro Thr Leu
    370                 375                 380

Glu Asp Leu Glu Gln Phe Ser Glu Lys Phe Tyr Cys Ser Cys Tyr Ser
385                 390                 395                 400

Thr Leu Ser Cys Lys Glu Lys Ala Asp Val Lys Asp Thr Asp Ala Val
```

```
                405                 410                 415

Asp Val Cys Ile Ala Asp Gly Val Cys Ile Asp Ala Phe Leu Lys Pro
            420                 425                 430

Pro Met Glu Thr Glu Glu Pro Gln Ile Phe Tyr Asn Ala Ser Pro Ser
        435                 440                 445

Thr Leu Ser
    450


<210> SEQ ID NO 26
<211> LENGTH: 449
<212> TYPE: PRT
<213> ORGANISM: Artificial Sequence
<220> FEATURE:
<223> OTHER INFORMATION: Synthetic Construct

<400> SEQUENCE: 26

Pro Val Ile Pro Asn Val Pro Phe Leu Trp Ala Trp Asn Ala Pro Ser
1               5                   10                  15

Glu Phe Cys Leu Gly Lys Phe Asp Glu Pro Leu Asp Met Ser Leu Phe
            20                  25                  30

Ser Phe Ile Gly Ser Pro Arg Ile Asn Ala Thr Gly Gln Gly Val Thr
        35                  40                  45

Ile Phe Tyr Val Asp Arg Leu Gly Tyr Tyr Pro Tyr Ile Asp Ser Ile
    50                  55                  60

Thr Gly Val Thr Val Asn Gly Gly Ile Pro Gln Lys Ile Ser Leu Gln
65                  70                  75                  80

Asp His Leu Asp Lys Ala Lys Lys Asp Ile Thr Phe Tyr Met Pro Val
                85                  90                  95

Asp Asn Leu Gly Met Ala Val Ile Asp Trp Glu Glu Trp Arg Pro Thr
            100                 105                 110

Trp Ala Arg Asn Trp Lys Pro Lys Asp Val Tyr Lys Asn Arg Ser Ile
        115                 120                 125

Glu Leu Val Gln Gln Gln Asn Val Gln Leu Ser Leu Thr Glu Ala Thr
    130                 135                 140

Glu Lys Ala Lys Gln Glu Phe Glu Lys Ala Gly Lys Asp Phe Leu Val
145                 150                 155                 160

Glu Thr Ile Lys Leu Gly Lys Leu Leu Arg Pro Asn His Leu Trp Gly
                165                 170                 175

Tyr Tyr Leu Phe Pro Asp Cys Tyr Asn His His Tyr Lys Lys Pro Gly
            180                 185                 190

Tyr Asn Gly Ser Cys Phe Asn Val Glu Ile Lys Arg Asn Asp Asp Leu
        195                 200                 205

Ser Trp Leu Trp Asn Glu Ser Thr Ala Leu Tyr Pro Ser Ile Tyr Leu
    210                 215                 220

Asn Thr Gln Gln Ser Pro Val Ala Ala Thr Leu Tyr Val Arg Asn Arg
225                 230                 235                 240

Val Arg Glu Ala Ile Arg Val Ser Lys Ile Pro Asp Ala Lys Ser Pro
                245                 250                 255

Leu Pro Val Phe Ala Tyr Thr Arg Ile Val Phe Thr Asp Gln Val Leu
            260                 265                 270

Lys Phe Leu Ser Gln Asp Glu Leu Val Tyr Thr Phe Gly Glu Thr Val
        275                 280                 285

Ala Leu Gly Ala Ser Gly Ile Val Ile Trp Gly Thr Leu Ser Ile Thr
    290                 295                 300

Arg Thr Lys Glu Ser Cys Gln Ala Ile Lys Glu Tyr Met Asp Thr Thr
```

305 310 315 320

Leu Asn Pro Tyr Ile Ile Asn Val Thr Leu Ala Ala Lys Met Cys Ser
325 330 335

Gln Val Leu Cys Gln Glu Gln Gly Val Cys Ile Arg Lys Asn Trp Asn
340 345 350

Ser Ser Asp Tyr Leu His Leu Asn Pro Asp Asn Phe Ala Ile Gln Leu
355 360 365

Glu Lys Gly Gly Lys Phe Thr Val Arg Gly Lys Pro Thr Leu Glu Asp
370 375 380

Leu Glu Gln Phe Ser Glu Lys Phe Tyr Cys Ser Cys Tyr Ser Thr Leu
385 390 395 400

Ser Cys Lys Glu Lys Ala Asp Val Lys Asp Thr Asp Ala Val Asp Val
405 410 415

Cys Ile Ala Asp Gly Val Cys Ile Asp Ala Phe Leu Lys Pro Pro Met
420 425 430

Glu Thr Glu Glu Pro Gln Ile Phe Tyr Asn Ala Ser Pro Ser Thr Leu
435 440 445

Ser

<210> SEQ ID NO 27
<211> LENGTH: 432
<212> TYPE: PRT
<213> ORGANISM: Artificial Sequence
<220> FEATURE:
<223> OTHER INFORMATION: Synthetic Construct

<400> SEQUENCE: 27

Leu Asn Phe Arg Ala Pro Pro Val Ile Pro Asn Val Pro Phe Leu Trp
1 5 10 15

Ala Trp Asn Ala Pro Ser Glu Phe Cys Leu Gly Lys Phe Asp Glu Pro
20 25 30

Leu Asp Met Ser Leu Phe Ser Phe Ile Gly Ser Pro Arg Ile Asn Ala
35 40 45

Thr Gly Gln Gly Val Thr Ile Phe Tyr Val Asp Arg Leu Gly Tyr Tyr
50 55 60

Pro Tyr Ile Asp Ser Ile Thr Gly Val Thr Val Asn Gly Gly Ile Pro
65 70 75 80

Gln Lys Ile Ser Leu Gln Asp His Leu Asp Lys Ala Lys Lys Asp Ile
85 90 95

Thr Phe Tyr Met Pro Val Asp Asn Leu Gly Met Ala Val Ile Asp Trp
100 105 110

Glu Glu Trp Arg Pro Thr Trp Ala Arg Asn Trp Lys Pro Lys Asp Val
115 120 125

Tyr Lys Asn Arg Ser Ile Glu Leu Val Gln Gln Gln Asn Val Gln Leu
130 135 140

Ser Leu Thr Glu Ala Thr Glu Lys Ala Lys Gln Glu Phe Glu Lys Ala
145 150 155 160

Gly Lys Asp Phe Leu Val Glu Thr Ile Lys Leu Gly Lys Leu Leu Arg
165 170 175

Pro Asn His Leu Trp Gly Tyr Tyr Leu Phe Pro Asp Cys Tyr Asn His
180 185 190

His Tyr Lys Lys Pro Gly Tyr Asn Gly Ser Cys Phe Asn Val Glu Ile
195 200 205

Lys Arg Asn Asp Asp Leu Ser Trp Leu Trp Asn Glu Ser Thr Ala Leu
210 215 220

Tyr Pro Ser Ile Tyr Leu Asn Thr Gln Gln Ser Pro Val Ala Ala Thr
225 230 235 240

Leu Tyr Val Arg Asn Arg Val Arg Glu Ala Ile Arg Val Ser Lys Ile
245 250 255

Pro Asp Ala Lys Ser Pro Leu Pro Val Phe Ala Tyr Thr Arg Ile Val
260 265 270

Phe Thr Asp Gln Val Leu Lys Phe Leu Ser Gln Asp Glu Leu Val Tyr
275 280 285

Thr Phe Gly Glu Thr Val Ala Leu Gly Ala Ser Gly Ile Val Ile Trp
290 295 300

Gly Thr Trp Glu Asn Thr Arg Thr Lys Glu Ser Cys Gln Ala Ile Lys
305 310 315 320

Glu Tyr Met Asp Thr Thr Leu Asn Pro Tyr Ile Ile Asn Val Thr Leu
325 330 335

Ala Ala Lys Met Cys Ser Gln Val Leu Cys Gln Glu Gln Gly Val Cys
340 345 350

Ile Arg Lys Asn Trp Asn Ser Ser Asp Tyr Leu His Leu Asn Pro Asp
355 360 365

Asn Phe Ala Ile Gln Leu Glu Lys Gly Gly Lys Phe Thr Val Arg Gly
370 375 380

Lys Pro Thr Leu Glu Asp Leu Glu Gln Phe Ser Glu Lys Phe Tyr Cys
385 390 395 400

Ser Cys Tyr Ser Thr Leu Ser Cys Lys Glu Lys Ala Asp Val Lys Asp
405 410 415

Thr Asp Ala Val Asp Val Cys Ile Ala Asp Gly Val Cys Ile Asp Ala
420 425 430

<210> SEQ ID NO 28
<211> LENGTH: 429
<212> TYPE: PRT
<213> ORGANISM: Artificial Sequence
<220> FEATURE:
<223> OTHER INFORMATION: Synthetic Construct

<400> SEQUENCE: 28

Leu Asn Phe Arg Ala Pro Pro Val Ile Pro Asn Val Pro Phe Leu Trp
1 5 10 15

Ala Trp Asn Ala Pro Ser Glu Phe Cys Leu Gly Lys Phe Asp Glu Pro
20 25 30

Leu Asp Met Ser Leu Phe Ser Phe Ile Gly Ser Pro Arg Ile Asn Ala
35 40 45

Thr Gly Gln Gly Val Thr Ile Phe Tyr Val Asp Arg Leu Gly Tyr Tyr
50 55 60

Pro Tyr Ile Asp Ser Ile Thr Gly Val Thr Val Asn Gly Gly Ile Pro
65 70 75 80

Gln Lys Ile Ser Leu Gln Asp His Leu Asp Lys Ala Lys Lys Asp Ile
85 90 95

Thr Phe Tyr Met Pro Val Asp Asn Leu Gly Met Ala Val Ile Asp Trp
100 105 110

Glu Glu Trp Arg Pro Thr Trp Ala Arg Asn Trp Lys Pro Lys Asp Val
115 120 125

Tyr Lys Asn Arg Ser Ile Glu Leu Val Gln Gln Gln Asn Val Gln Leu
130 135 140

Ser Leu Thr Glu Ala Thr Glu Lys Ala Lys Gln Glu Phe Glu Lys Ala
145 150 155 160

```
Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Trp Glu Asn Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys
            420                 425


<210> SEQ ID NO 29
<211> LENGTH: 426
<212> TYPE: PRT
<213> ORGANISM: Artificial Sequence
<220> FEATURE:
<223> OTHER INFORMATION: Synthetic Construct

<400> SEQUENCE: 29

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95
```

```
Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Trp Glu Asn Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp
            420                 425
```

<210> SEQ ID NO 30
<211> LENGTH: 423
<212> TYPE: PRT
<213> ORGANISM: Artificial Sequence
<220> FEATURE:
<223> OTHER INFORMATION: Synthetic Construct

<400> SEQUENCE: 30

```
Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30
```

```
Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Trp Glu Asn Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys
            420
```

<210> SEQ ID NO 31
<211> LENGTH: 420

```
<212> TYPE: PRT
<213> ORGANISM: Artificial Sequence
<220> FEATURE:
<223> OTHER INFORMATION: Synthetic Construct

<400> SEQUENCE: 31

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Trp Glu Asn Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380
```

```
Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val
            420


<210> SEQ ID NO 32
<211> LENGTH: 433
<212> TYPE: PRT
<213> ORGANISM: Artificial Sequence
<220> FEATURE:
<223> OTHER INFORMATION: Synthetic Construct

<400> SEQUENCE: 32

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Ser
    290                 295                 300

Trp Glu Asn Thr Arg Thr Lys Glu Ser Cys Gln Ala Ile Lys Glu Tyr
305                 310                 315                 320
```

Met Asp Thr Thr Leu Asn Pro Tyr Ile Ile Asn Val Thr Leu Ala Ala
325 330 335

Lys Met Cys Ser Gln Val Leu Cys Gln Glu Gln Gly Val Cys Ile Arg
340 345 350

Lys Asn Trp Asn Ser Ser Asp Tyr Leu His Leu Asn Pro Asp Asn Phe
355 360 365

Ala Ile Gln Leu Glu Lys Gly Gly Lys Phe Thr Val Arg Gly Lys Pro
370 375 380

Thr Leu Glu Asp Leu Glu Gln Phe Ser Glu Lys Phe Tyr Cys Ser Cys
385 390 395 400

Tyr Ser Thr Leu Ser Cys Lys Glu Lys Ala Asp Val Lys Asp Thr Asp
405 410 415

Ala Val Asp Val Cys Ile Ala Asp Gly Val Cys Ile Asp Ala Phe Leu
420 425 430

Lys

<210> SEQ ID NO 33
<211> LENGTH: 435
<212> TYPE: PRT
<213> ORGANISM: Artificial Sequence
<220> FEATURE:
<223> OTHER INFORMATION: Synthetic Construct

<400> SEQUENCE: 33

Phe Arg Ala Pro Pro Val Ile Pro Asn Val Pro Phe Leu Trp Ala Trp
1 5 10 15

Asn Ala Pro Ser Glu Phe Cys Leu Gly Lys Phe Asp Glu Pro Leu Asp
20 25 30

Met Ser Leu Phe Ser Phe Ile Gly Ser Pro Arg Ile Asn Ala Thr Gly
35 40 45

Gln Gly Val Thr Ile Phe Tyr Val Asp Arg Leu Gly Tyr Tyr Pro Tyr
50 55 60

Ile Asp Ser Ile Thr Gly Val Thr Val Asn Gly Gly Ile Pro Gln Lys
65 70 75 80

Ile Ser Leu Gln Asp His Leu Asp Lys Ala Lys Lys Asp Ile Thr Phe
85 90 95

Tyr Met Pro Val Asp Asn Leu Gly Met Ala Val Ile Asp Trp Glu Glu
100 105 110

Trp Arg Pro Thr Trp Ala Arg Asn Trp Lys Pro Lys Asp Val Tyr Lys
115 120 125

Asn Arg Ser Ile Glu Leu Val Gln Gln Gln Asn Val Gln Leu Ser Leu
130 135 140

Thr Glu Ala Thr Glu Lys Ala Lys Gln Glu Phe Glu Lys Ala Gly Lys
145 150 155 160

Asp Phe Leu Val Glu Thr Ile Lys Leu Gly Lys Leu Leu Arg Pro Asn
165 170 175

His Leu Trp Gly Tyr Tyr Leu Phe Pro Asp Cys Tyr Asn His His Tyr
180 185 190

Lys Lys Pro Gly Tyr Asn Gly Ser Cys Phe Asn Val Glu Ile Lys Arg
195 200 205

Asn Asp Asp Leu Ser Trp Leu Trp Asn Glu Ser Thr Ala Leu Tyr Pro
210 215 220

Ser Ile Tyr Leu Asn Thr Gln Gln Ser Pro Val Ala Ala Thr Leu Tyr
225 230 235 240

Val Arg Asn Arg Val Arg Glu Ala Ile Arg Val Ser Lys Ile Pro Asp

```
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Thr
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe Leu
            420                 425                 430

Lys Pro Pro
        435


<210> SEQ ID NO 34
<211> LENGTH: 436
<212> TYPE: PRT
<213> ORGANISM: Artificial Sequence
<220> FEATURE:
<223> OTHER INFORMATION: Synthetic Construct

<400> SEQUENCE: 34

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
```

```
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Thr
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe Leu
            420                 425                 430

Lys Pro Pro Met
        435


<210> SEQ ID NO 35
<211> LENGTH: 437
<212> TYPE: PRT
<213> ORGANISM: Artificial Sequence
<220> FEATURE:
<223> OTHER INFORMATION: Synthetic Construct

<400> SEQUENCE: 35

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
```

```
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Thr
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe Leu
            420                 425                 430

Lys Pro Pro Met Glu
        435
```

<210> SEQ ID NO 36
<211> LENGTH: 438
<212> TYPE: PRT
<213> ORGANISM: Artificial Sequence
<220> FEATURE:
<223> OTHER INFORMATION: Synthetic Construct

<400> SEQUENCE: 36

```
Phe Arg Ala Pro Pro Val Ile Pro Asn Val Pro Phe Leu Trp Ala Trp
```

-continued

```
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Thr
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe Leu
            420                 425                 430
```

```
Lys Pro Pro Met Glu Thr
        435


<210> SEQ ID NO 37
<211> LENGTH: 439
<212> TYPE: PRT
<213> ORGANISM: Artificial Sequence
<220> FEATURE:
<223> OTHER INFORMATION: Synthetic Construct

<400> SEQUENCE: 37

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Thr
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350
```

```
Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe Leu
            420                 425                 430

Lys Pro Pro Met Glu Thr Glu
        435


<210> SEQ ID NO 38
<211> LENGTH: 454
<212> TYPE: PRT
<213> ORGANISM: Artificial Sequence
<220> FEATURE:
<223> OTHER INFORMATION: Synthetic Construct

<400> SEQUENCE: 38

Asn Phe Arg Ala Pro Pro Val Ile Pro Asn Val Pro Phe Leu Trp Ala
1               5                   10                  15

Trp Asn Ala Pro Ser Glu Phe Cys Leu Gly Lys Phe Asp Glu Pro Leu
            20                  25                  30

Asp Met Ser Leu Phe Ser Phe Ile Gly Ser Pro Arg Ile Asn Ala Thr
        35                  40                  45

Gly Gln Gly Val Thr Ile Phe Tyr Val Asp Arg Leu Gly Tyr Tyr Pro
    50                  55                  60

Tyr Ile Asp Ser Ile Thr Gly Val Thr Val Asn Gly Gly Ile Pro Gln
65                  70                  75                  80

Lys Ile Ser Leu Gln Asp His Leu Asp Lys Ala Lys Lys Asp Ile Thr
                85                  90                  95

Phe Tyr Met Pro Val Asp Asn Leu Gly Met Ala Val Ile Asp Trp Glu
            100                 105                 110

Glu Trp Arg Pro Thr Trp Ala Arg Asn Trp Lys Pro Lys Asp Val Tyr
        115                 120                 125

Lys Asn Arg Ser Ile Glu Leu Val Gln Gln Gln Asn Val Gln Leu Ser
    130                 135                 140

Leu Thr Glu Ala Thr Glu Lys Ala Lys Gln Glu Phe Glu Lys Ala Gly
145                 150                 155                 160

Lys Asp Phe Leu Val Glu Thr Ile Lys Leu Gly Lys Leu Leu Arg Pro
                165                 170                 175

Asn His Leu Trp Gly Tyr Tyr Leu Phe Pro Asp Cys Tyr Asn His His
            180                 185                 190

Tyr Lys Lys Pro Gly Tyr Asn Gly Ser Cys Phe Asn Val Glu Ile Lys
        195                 200                 205

Arg Asn Asp Asp Leu Ser Trp Leu Trp Asn Glu Ser Thr Ala Leu Tyr
    210                 215                 220

Pro Ser Ile Tyr Leu Asn Thr Gln Gln Ser Pro Val Ala Ala Thr Leu
225                 230                 235                 240

Tyr Val Arg Asn Arg Val Arg Glu Ala Ile Arg Val Ser Lys Ile Pro
                245                 250                 255

Asp Ala Lys Ser Pro Leu Pro Val Phe Ala Tyr Thr Arg Ile Val Phe
            260                 265                 270
```

```
Thr Asp Gln Val Leu Lys Phe Leu Ser Gln Asp Glu Leu Val Tyr Thr
        275                 280                 285

Phe Gly Glu Thr Val Ala Leu Gly Ala Ser Gly Ile Val Ile Trp Gly
    290                 295                 300

Thr Leu Ser Ile Thr Arg Thr Lys Glu Ser Cys Gln Ala Ile Lys Glu
305                 310                 315                 320

Tyr Met Asp Thr Thr Leu Asn Pro Tyr Ile Ile Asn Val Thr Leu Ala
                325                 330                 335

Ala Lys Met Cys Ser Gln Val Leu Cys Gln Glu Gln Gly Val Cys Ile
            340                 345                 350

Arg Lys Asn Trp Asn Ser Ser Asp Tyr Leu His Leu Asn Pro Asp Asn
        355                 360                 365

Phe Ala Ile Gln Leu Glu Lys Gly Gly Lys Phe Thr Val Arg Gly Lys
    370                 375                 380

Pro Thr Leu Glu Asp Leu Glu Gln Phe Ser Glu Lys Phe Tyr Cys Ser
385                 390                 395                 400

Cys Tyr Ser Thr Leu Ser Cys Lys Glu Lys Ala Asp Val Lys Asp Thr
                405                 410                 415

Asp Ala Val Asp Val Cys Ile Ala Asp Gly Val Cys Ile Asp Ala Phe
            420                 425                 430

Leu Lys Pro Pro Met Glu Thr Glu Glu Pro Gln Ile Phe Tyr Asn Ala
        435                 440                 445

Ser Pro Ser Thr Leu Ser
    450


<210> SEQ ID NO 39
<211> LENGTH: 452
<212> TYPE: PRT
<213> ORGANISM: Artificial Sequence
<220> FEATURE:
<223> OTHER INFORMATION: Synthetic Construct

<400> SEQUENCE: 39

Arg Ala Pro Pro Val Ile Pro Asn Val Pro Phe Leu Trp Ala Trp Asn
1               5                   10                  15

Ala Pro Ser Glu Phe Cys Leu Gly Lys Phe Asp Glu Pro Leu Asp Met
            20                  25                  30

Ser Leu Phe Ser Phe Ile Gly Ser Pro Arg Ile Asn Ala Thr Gly Gln
        35                  40                  45

Gly Val Thr Ile Phe Tyr Val Asp Arg Leu Gly Tyr Tyr Pro Tyr Ile
    50                  55                  60

Asp Ser Ile Thr Gly Val Thr Val Asn Gly Gly Ile Pro Gln Lys Ile
65                  70                  75                  80

Ser Leu Gln Asp His Leu Asp Lys Ala Lys Lys Asp Ile Thr Phe Tyr
                85                  90                  95

Met Pro Val Asp Asn Leu Gly Met Ala Val Ile Asp Trp Glu Glu Trp
            100                 105                 110

Arg Pro Thr Trp Ala Arg Asn Trp Lys Pro Lys Asp Val Tyr Lys Asn
        115                 120                 125

Arg Ser Ile Glu Leu Val Gln Gln Gln Asn Val Gln Leu Ser Leu Thr
    130                 135                 140

Glu Ala Thr Glu Lys Ala Lys Gln Glu Phe Glu Lys Ala Gly Lys Asp
145                 150                 155                 160

Phe Leu Val Glu Thr Ile Lys Leu Gly Lys Leu Leu Arg Pro Asn His
                165                 170                 175
```

```
Leu Trp Gly Tyr Tyr Leu Phe Pro Asp Cys Tyr Asn His His Tyr Lys
            180                 185                 190

Lys Pro Gly Tyr Asn Gly Ser Cys Phe Asn Val Glu Ile Lys Arg Asn
        195                 200                 205

Asp Asp Leu Ser Trp Leu Trp Asn Glu Ser Thr Ala Leu Tyr Pro Ser
    210                 215                 220

Ile Tyr Leu Asn Thr Gln Gln Ser Pro Val Ala Ala Thr Leu Tyr Val
225                 230                 235                 240

Arg Asn Arg Val Arg Glu Ala Ile Arg Val Ser Lys Ile Pro Asp Ala
                245                 250                 255

Lys Ser Pro Leu Pro Val Phe Ala Tyr Thr Arg Ile Val Phe Thr Asp
            260                 265                 270

Gln Val Leu Lys Phe Leu Ser Gln Asp Glu Leu Val Tyr Thr Phe Gly
        275                 280                 285

Glu Thr Val Ala Leu Gly Ala Ser Gly Ile Val Ile Trp Gly Thr Leu
    290                 295                 300

Ser Ile Thr Arg Thr Lys Glu Ser Cys Gln Ala Ile Lys Glu Tyr Met
305                 310                 315                 320

Asp Thr Thr Leu Asn Pro Tyr Ile Ile Asn Val Thr Leu Ala Ala Lys
                325                 330                 335

Met Cys Ser Gln Val Leu Cys Gln Glu Gln Gly Val Cys Ile Arg Lys
            340                 345                 350

Asn Trp Asn Ser Ser Asp Tyr Leu His Leu Asn Pro Asp Asn Phe Ala
        355                 360                 365

Ile Gln Leu Glu Lys Gly Gly Lys Phe Thr Val Arg Gly Lys Pro Thr
    370                 375                 380

Leu Glu Asp Leu Glu Gln Phe Ser Glu Lys Phe Tyr Cys Ser Cys Tyr
385                 390                 395                 400

Ser Thr Leu Ser Cys Lys Glu Lys Ala Asp Val Lys Asp Thr Asp Ala
                405                 410                 415

Val Asp Val Cys Ile Ala Asp Gly Val Cys Ile Asp Ala Phe Leu Lys
            420                 425                 430

Pro Pro Met Glu Thr Glu Glu Pro Gln Ile Phe Tyr Asn Ala Ser Pro
        435                 440                 445

Ser Thr Leu Ser
    450


<210> SEQ ID NO 40
<211> LENGTH: 450
<212> TYPE: PRT
<213> ORGANISM: Artificial Sequence
<220> FEATURE:
<223> OTHER INFORMATION: Synthetic Construct

<400> SEQUENCE: 40

Pro Pro Val Ile Pro Asn Val Pro Phe Leu Trp Ala Trp Asn Ala Pro
1               5                   10                  15

Ser Glu Phe Cys Leu Gly Lys Phe Asp Glu Pro Leu Asp Met Ser Leu
            20                  25                  30

Phe Ser Phe Ile Gly Ser Pro Arg Ile Asn Ala Thr Gly Gln Gly Val
        35                  40                  45

Thr Ile Phe Tyr Val Asp Arg Leu Gly Tyr Tyr Pro Tyr Ile Asp Ser
    50                  55                  60

Ile Thr Gly Val Thr Val Asn Gly Gly Ile Pro Gln Lys Ile Ser Leu
65                  70                  75                  80
```

```
Gln Asp His Leu Asp Lys Ala Lys Lys Asp Ile Thr Phe Tyr Met Pro
                85                  90                  95

Val Asp Asn Leu Gly Met Ala Val Ile Asp Trp Glu Glu Trp Arg Pro
            100                 105                 110

Thr Trp Ala Arg Asn Trp Lys Pro Lys Asp Val Tyr Lys Asn Arg Ser
        115                 120                 125

Ile Glu Leu Val Gln Gln Gln Asn Val Gln Leu Ser Leu Thr Glu Ala
    130                 135                 140

Thr Glu Lys Ala Lys Gln Glu Phe Glu Lys Ala Gly Lys Asp Phe Leu
145                 150                 155                 160

Val Glu Thr Ile Lys Leu Gly Lys Leu Leu Arg Pro Asn His Leu Trp
                165                 170                 175

Gly Tyr Tyr Leu Phe Pro Asp Cys Tyr Asn His His Tyr Lys Lys Pro
            180                 185                 190

Gly Tyr Asn Gly Ser Cys Phe Asn Val Glu Ile Lys Arg Asn Asp Asp
        195                 200                 205

Leu Ser Trp Leu Trp Asn Glu Ser Thr Ala Leu Tyr Pro Ser Ile Tyr
    210                 215                 220

Leu Asn Thr Gln Gln Ser Pro Val Ala Ala Thr Leu Tyr Val Arg Asn
225                 230                 235                 240

Arg Val Arg Glu Ala Ile Arg Val Ser Lys Ile Pro Asp Ala Lys Ser
                245                 250                 255

Pro Leu Pro Val Phe Ala Tyr Thr Arg Ile Val Phe Thr Asp Gln Val
            260                 265                 270

Leu Lys Phe Leu Ser Gln Asp Glu Leu Val Tyr Thr Phe Gly Glu Thr
        275                 280                 285

Val Ala Leu Gly Ala Ser Gly Ile Val Ile Trp Gly Thr Leu Ser Ile
    290                 295                 300

Thr Arg Thr Lys Glu Ser Cys Gln Ala Ile Lys Glu Tyr Met Asp Thr
305                 310                 315                 320

Thr Leu Asn Pro Tyr Ile Ile Asn Val Thr Leu Ala Ala Lys Met Cys
                325                 330                 335

Ser Gln Val Leu Cys Gln Glu Gln Gly Val Cys Ile Arg Lys Asn Trp
            340                 345                 350

Asn Ser Ser Asp Tyr Leu His Leu Asn Pro Asp Asn Phe Ala Ile Gln
        355                 360                 365

Leu Glu Lys Gly Gly Lys Phe Thr Val Arg Gly Lys Pro Thr Leu Glu
    370                 375                 380

Asp Leu Glu Gln Phe Ser Glu Lys Phe Tyr Cys Ser Cys Tyr Ser Thr
385                 390                 395                 400

Leu Ser Cys Lys Glu Lys Ala Asp Val Lys Asp Thr Asp Ala Val Asp
                405                 410                 415

Val Cys Ile Ala Asp Gly Val Cys Ile Asp Ala Phe Leu Lys Pro Pro
            420                 425                 430

Met Glu Thr Glu Glu Pro Gln Ile Phe Tyr Asn Ala Ser Pro Ser Thr
        435                 440                 445

Leu Ser
    450
```

<210> SEQ ID NO 41
<211> LENGTH: 428
<212> TYPE: PRT
<213> ORGANISM: Artificial Sequence
<220> FEATURE:

<223> OTHER INFORMATION: Synthetic Construct

<400> SEQUENCE: 41

```
Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Ser
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400
```

```
Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile
            420                 425


<210> SEQ ID NO 42
<211> LENGTH: 429
<212> TYPE: PRT
<213> ORGANISM: Artificial Sequence
<220> FEATURE:
<223> OTHER INFORMATION: Synthetic Construct

<400> SEQUENCE: 42

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Ser
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335
```

```
Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp
            420                 425


<210> SEQ ID NO 43
<211> LENGTH: 430
<212> TYPE: PRT
<213> ORGANISM: Artificial Sequence
<220> FEATURE:
<223> OTHER INFORMATION: Synthetic Construct

<400> SEQUENCE: 43

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270
```

```
Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Ser
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala
            420                 425                 430


<210> SEQ ID NO 44
<211> LENGTH: 431
<212> TYPE: PRT
<213> ORGANISM: Artificial Sequence
<220> FEATURE:
<223> OTHER INFORMATION: Synthetic Construct

<400> SEQUENCE: 44

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205
```

```
Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Ser
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe
            420                 425                 430


<210> SEQ ID NO 45
<211> LENGTH: 441
<212> TYPE: PRT
<213> ORGANISM: Artificial Sequence
<220> FEATURE:
<223> OTHER INFORMATION: Synthetic Construct

<400> SEQUENCE: 45

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140
```

```
Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Thr
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe Leu
            420                 425                 430

Lys Pro Pro Met Glu Thr Glu Glu Pro
        435                 440
```

```
<210> SEQ ID NO 46
<211> LENGTH: 443
<212> TYPE: PRT
<213> ORGANISM: Artificial Sequence
<220> FEATURE:
<223> OTHER INFORMATION: Synthetic Construct

<400> SEQUENCE: 46

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60
```

```
Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Thr
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe Leu
            420                 425                 430

Lys Pro Pro Met Glu Thr Glu Glu Pro Gln Ile
        435                 440
```

<210> SEQ ID NO 47
<211> LENGTH: 445
<212> TYPE: PRT
<213> ORGANISM: Artificial Sequence
<220> FEATURE:
<223> OTHER INFORMATION: Synthetic Construct

<400> SEQUENCE: 47

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Thr
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp

```
                405                 410                 415

Ala Val Asp Val Cys Ile Ala Asp Gly Val Cys Ile Asp Ala Phe Leu
            420                 425                 430

Lys Pro Pro Met Glu Thr Glu Glu Pro Gln Ile Phe Tyr
        435                 440                 445


<210> SEQ ID NO 48
<211> LENGTH: 447
<212> TYPE: PRT
<213> ORGANISM: Artificial Sequence
<220> FEATURE:
<223> OTHER INFORMATION: Synthetic Construct

<400> SEQUENCE: 48

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Thr
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
```

```
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe Leu
            420                 425                 430

Lys Pro Pro Met Glu Thr Glu Glu Pro Gln Ile Phe Tyr Asn Ala
        435                 440                 445


<210> SEQ ID NO 49
<211> LENGTH: 449
<212> TYPE: PRT
<213> ORGANISM: Artificial Sequence
<220> FEATURE:
<223> OTHER INFORMATION: Synthetic Construct

<400> SEQUENCE: 49

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
```

```
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Thr
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe Leu
            420                 425                 430

Lys Pro Pro Met Glu Thr Glu Glu Pro Gln Ile Phe Tyr Asn Ala Ser
        435                 440                 445

Pro
```

<210> SEQ ID NO 50
<211> LENGTH: 451
<212> TYPE: PRT
<213> ORGANISM: Artificial Sequence
<220> FEATURE:
<223> OTHER INFORMATION: Synthetic Construct

<400> SEQUENCE: 50

```
Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160
```

```
Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Thr
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe Leu
            420                 425                 430

Lys Pro Pro Met Glu Thr Glu Glu Pro Gln Ile Phe Tyr Asn Ala Ser
        435                 440                 445

Pro Ser Thr
    450
```

<210> SEQ ID NO 51
<211> LENGTH: 435
<212> TYPE: PRT
<213> ORGANISM: Artificial Sequence
<220> FEATURE:
<223> OTHER INFORMATION: Synthetic Construct

<400> SEQUENCE: 51

```
Met Ala Ala His Leu Leu Pro Ile Cys Ala Leu Phe Leu Thr Leu Leu
1               5                   10                  15

Asp Met Ala Gln Gly Phe Arg Gly Pro Leu Leu Pro Asn Arg Pro Phe
            20                  25                  30

Thr Thr Val Trp Asn Ala Asn Thr Gln Trp Cys Leu Glu Arg His Gly
        35                  40                  45

Val Asp Val Asp Val Ser Val Phe Asp Val Val Ala Asn Pro Gly Gln
    50                  55                  60
```

```
Thr Phe Arg Gly Pro Asp Met Thr Ile Phe Tyr Ser Ser Gln Leu Gly
65                  70                  75                  80

Thr Tyr Pro Tyr Tyr Thr Pro Thr Gly Glu Pro Val Phe Gly Gly Leu
                85                  90                  95

Pro Gln Asn Ala Ser Leu Ile Ala His Leu Ala Arg Thr Phe Gln Asp
            100                 105                 110

Ile Leu Ala Ala Ile Pro Ala Pro Asp Phe Ser Gly Leu Ala Val Ile
        115                 120                 125

Asp Trp Glu Ala Trp Arg Pro Arg Trp Ala Phe Asn Trp Asp Thr Lys
    130                 135                 140

Asp Ile Tyr Arg Gln Arg Ser Arg Ala Leu Val Gln Ala Gln His Pro
145                 150                 155                 160

Asp Trp Pro Ala Pro Gln Val Glu Ala Val Ala Gln Asp Gln Phe Gln
                165                 170                 175

Gly Ala Ala Arg Ala Trp Met Ala Gly Thr Leu Gln Leu Gly Arg Ala
            180                 185                 190

Leu Arg Pro Arg Gly Leu Trp Gly Phe Tyr Gly Phe Pro Asp Cys Tyr
        195                 200                 205

Asn Tyr Asp Phe Leu Ser Pro Asn Tyr Thr Gly Gln Cys Pro Ser Gly
    210                 215                 220

Ile Arg Ala Gln Asn Asp Gln Leu Gly Trp Leu Trp Gly Gln Ser Arg
225                 230                 235                 240

Ala Leu Tyr Pro Ser Ile Tyr Met Pro Ala Val Leu Glu Gly Thr Gly
                245                 250                 255

Lys Ser Gln Met Tyr Val Gln His Arg Val Ala Glu Ala Phe Arg Val
            260                 265                 270

Ala Val Ala Ala Gly Asp Pro Asn Leu Pro Val Leu Pro Tyr Val Gln
        275                 280                 285

Ile Phe Tyr Asp Thr Thr Asn His Phe Leu Pro Leu Asp Glu Leu Glu
    290                 295                 300

His Ser Leu Gly Glu Ser Ala Ala Gln Gly Ala Ala Gly Val Val Leu
305                 310                 315                 320

Trp Val Ser Trp Glu Asn Thr Arg Thr Lys Glu Ser Cys Gln Ala Ile
                325                 330                 335

Lys Glu Tyr Met Asp Thr Thr Leu Gly Pro Phe Ile Leu Asn Val Thr
            340                 345                 350

Ser Gly Ala Leu Leu Cys Ser Gln Ala Leu Cys Ser Gly His Gly Arg
        355                 360                 365

Cys Val Arg Arg Thr Ser His Pro Lys Ala Leu Leu Leu Leu Asn Pro
    370                 375                 380

Ala Ser Phe Ser Ile Gln Leu Thr Pro Gly Gly Gly Pro Leu Ser Leu
385                 390                 395                 400

Arg Gly Ala Leu Ser Leu Glu Asp Gln Ala Gln Met Ala Val Glu Phe
                405                 410                 415

Lys Cys Arg Cys Tyr Pro Gly Trp Gln Ala Pro Trp Cys Glu Arg Lys
            420                 425                 430

Ser Met Trp
        435
```

<210> SEQ ID NO 52
<211> LENGTH: 9
<212> TYPE: PRT
<213> ORGANISM: Artificial Sequence
<220> FEATURE:

```
<223> OTHER INFORMATION: Synthetic Construct

<400> SEQUENCE: 52

Phe Arg Gly Pro Leu Leu Pro Asn Arg
1               5


<210> SEQ ID NO 53
<211> LENGTH: 14
<212> TYPE: PRT
<213> ORGANISM: Artificial Sequence
<220> FEATURE:
<223> OTHER INFORMATION: Synthetic Construct

<400> SEQUENCE: 53

Phe Arg Gly Pro Leu Leu Pro Asn Arg Pro Phe Thr Thr Val
1               5                   10
```